United States Patent [19]

Onoue et al.

[11] Patent Number: 5,134,138
[45] Date of Patent: Jul. 28, 1992

[54] PHENACYLPYRIDINIOTHIOCEPHALOS-PORINS

[75] Inventors: Hiroshi Onoue; Kyoji Minami; Koji Ishikura, all of Nara, Japan

[73] Assignee: Shionogi & Co., Ltd., Osaka, Japan

[21] Appl. No.: 550,091

[22] Filed: Jul. 9, 1990

[30] Foreign Application Priority Data

Jul. 18, 1989 [JP] Japan .................. 1-186330

[51] Int. Cl.$^5$ .................. C07D 501/36; A61K 31/545
[52] U.S. Cl. .................. 514/206; 540/221; 540/227; 540/301; 514/201
[58] Field of Search .............. 540/226, 227, 225, 221; 514/201, 206

[56] References Cited

U.S. PATENT DOCUMENTS

| 4,691,014 | 9/1987 | Naito et al. | 540/226 |
| 4,880,797 | 11/1989 | Nakagawa et al. | 540/226 |

FOREIGN PATENT DOCUMENTS

| 0153709 | 9/1985 | European Pat. Off. |
| 0176369 | 4/1986 | European Pat. Off. |
| 0190900 | 8/1986 | European Pat. Off. |
| 0238060 | 9/1987 | European Pat. Off. |
| 0238061 | 9/1987 | European Pat. Off. |
| 0272827 | 6/1988 | European Pat. Off. |
| 62-209082 | 9/1989 | Japan. |

Primary Examiner—Nicholas S. Rizzo
Attorney, Agent, or Firm—Birch, Stewart, Kolasch & Birch

[57] ABSTRACT

An antibacterial 3-vic-dihydroxyaroylmethylpyridiniothiomethyl cephalosporin (I) and its salts represented by the following formula:

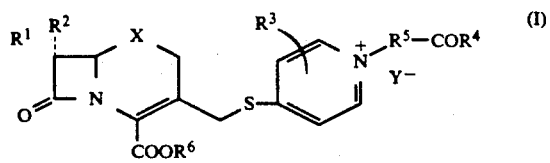

(wherein,
$R^1$ is amino group or acylamino; $R^2$ is hydrogen or methoxy; $R^3$ is hydrogen atom or substituent; $R^4$ is vic-dihydroxyaryl; $R^5$ is straight or branched lower alkylene; $R^6$ is hydrogen, a carboxy-protecting group or combined with Y a negative charge; X is —O—, —S— or sulfinyl; and Y is a counter-ion of pyridinio or combined with $R^6$ a negative charge), a disinfecting and treating method of bacterial infection using it, and synthetic methods thereof are provided.

13 Claims, No Drawings

PHENACYLPYRIDINIOTHIOCEPHALOSPORINS

The known cephalosporins having pyridiniomethyl at position 3 (e.g., cephaloridine) are strong antibacterials against Gram-positive bacteria. Recently, such compounds active against Gram-negative bacteria have been launched and are attractive. However, these are insufficient in clinical antibacterial activity (e.g. against Pseudomonas spp.). The present inventors tested various cephalosporins to find Compounds (I) superior in the objective antibacterial activity. This invention provides said antibacterial compounds, a disinfecting and treating method of bacterial infection using them, and synthesis thereof.

This invention relates to a novel vic-dihydroxyaroyl-methylpyridiniothiomethylcephalosporin (I) and its salts represented by the following formula:

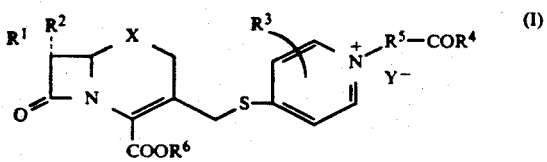

(wherein,
$R^1$ is amino or acylamino;
$R^2$ is hydrogen or methoxy;
$R^3$ hydrogen or substituent;
$R^4$ is vic-dihydroxyaryl;
$R^5$ is straight or branched lower alkylene;
$R^6$ is hydrogen, a carboxy protecting group or combined with Y a negative charge,
X is —O—, —S— or sulfinyl;
Y is a counter-ion of pyridinio or combined with $R^6$ a negative charge)

The groups of compound (I) are explained as follows:

When $R^1$ is acylamino, the acyl can be aliphatic, alicyclic, or aromatic carboxylic acyl including that forming an amide side chain of natural or synthetic penicillins and cephalosporins. Representative acyls are shown by the following formulas:

$R^{10}R^{11}$—CO (wherein, $R^{10}$ is hydrogen, or aliphatic, aromatic, heterocyclic or alicyclic group, or a group forming a carbonic acyl together with $R^{11}CO$;

$R^{11}$ is a single bond, —$R^{14}CH_2$ ($R^{14}$ is a single bond, oxygen, sulfur, or imino), >CH—$R^{12}$, >C=$R^{13}$, or the like divalent group;

$R^{12}$ is optionally protected carboxy, cyano, hydroxy, amino, sulfo, mercapto, or the like; and $R^{13}$ is oxo, thioxo, imino, hydroxyimino, optionally substituted alkoxyimino, aryloxyimino, alkylidene, or the like)

Preferably, $R^{10}$ is C1 to C8 aliphatic group (e.g., optionally substituted alkyl, alkenyl, alkinyl), monocyclic or polycyclic aromatic group (e.g., optionally substituted phenyl, naphthyl), monocyclic or polycyclic heterocyclic group (optionally substituted, five- or six-membered heterocyclyl optionally having up to 4 nitrogen, oxygen, and/or sulfur atom as hetero atom), mono- or poly-cyclic alicyclic group (optionally substituted, optionally having 1 or 2 double bond, 4 to 8 membered cycloalkyl), a group constituting C2 to C9 carbonic acyl (e.g., alkoxy-, alkylthio-, aralkoxy-, aralkylthio-, aryloxy-, arylthio-, or heterocyclooxy-carbonyl) or the like. A part of polycyclic group may be a saturated ring.

When $R^{12}$ is protected, the protective group can be that aiming to avoid adverse change during synthesis (e.g., ester, amide, halide, ether, anhydride) and that aiming to alter its physiological or pharmaceutical characteristics.

Representatives of the former are, when $R^{12}$ is hydroxy, sulfhydryl, amino, or the like, C1 to C8 alkyl (e.g., methyl, ethyl, isopropyl, butyl, t-butyl, cyclopentyl), monocyclic heterocyclyl (e.g., tetrahydropyranyl, tetrahydrofuranyl), C2 to C9 alkenyl (forming enol ether, enamine), C3 to C10 alkyl or alkoxysilyl or stannyl (e.g., trimethylsilyl, triethyl silyl, dimethyl-t-butylsilyl, trimethylstannyl, dimethylmethoxysilyl), C7 to C15 aralkyl (e.g., trityl, substituted diphenylmethyl, phenacyl), C1 to C10 acyl (e.g., alkanoyl, alkenoyl, aroyl, carbonic acid acyl); when $R^{12}$ is carboxy, sulfo, etc., an ester forming group (e.g., C1 to C8 alkyl, C7 to C20 aralkyl, C5 to C12 aryl), amide forming group (e.g., amino, C1 to C8 alkyl amino, C2 to C8 dialkylhydrazinyl), salt forming group (e.g., alkali metal, alkaline earth metal, C2 to C10 amine), and the like removable without adverse effect on other parts of the moleule.

Preferable representatives of the latter are when $R^{12}$ is carboxy or sulfo, a group removable in vivo (e.g., salt, pharmaceutically active ester, amide); when $R^{12}$ is hydroxy, sulfo, carbamoyl, sulfamoyl, C2 to C9 carbalkoxy, C8 to C15 carbaralkoxy, C1 to C8 alkanoyl, C8 to C15 aralkanoyl, C7 to C15 aroyl, monocyclic heterocyclocarbonyl, cyano, or the like; when $R^{12}$ is amino, C1 to C8 alkylsulfonyl, monocyclic arylsulfonyl, C1 to C8 alkyloxoimidazolidinylcarbonyl, dioxopiperazinylcarbonyl, alkylureidocarbonyl, thioureidocarbonyl, and the like.

When $R^{13}$ is alkoxyimino or alkylidene, it can be C1 to C8 saturated or unsaturated straight or cyclic group; or is mono- or poly-cyclic carbo- or hetero-cyclic aryloxyimino. Each can have a substituent (e.g., carboxy, esterified or amidated carboxy, hydroxy, C1 to C8 alkyl, C1 to C8 alkoxy).

$R^{10}$ to $R^{13}$ can further have a substituent. When the acyl remains in the final objective compound, it has preferably up to 20 C atoms.

There is a vic-dihydroxylatedaroylmethylpyridiniothiomethyl at position 3 of this cephalosporin compound. This pyridinio ring may optionally have a substituent $R^3$ (preferably e.g., halogen, cyano, C2 to C9 alkylene, C1 to C8 alkyl, C2 to C6 alkenyl, carboxy, C2 to C9 alkoxycarbonyl, C8 to C15 aralkoxycarbonyl, carbamoyl, nitro or a mono- or bi-cyclic heterocyclyl having optionally nitrogen, oxygen and/or sulfur as 1 to 4 hetero atoms).

The hydroxy of vic-dihydroxylated aryl $R^4$ at position 3 of this cephalosporin may optionally have a protecting group (e.g., alkali metal, alkaline earth metal, C1 to C8 acyl, C3 to C9 silyl, C7 to C15 aralkyl, C2 to C9 alkoxycarbonyl). Its aryl part $R^4$ may optionally have a substituent (preferably e.g., halogen, nitro, cyano, carboxy, carbamoyl, C2 to C9 alkoxycarbonyl, C8 to C15 aralkoxycarbonyl, C1 to C8 alkyl, C2 to C9 alkenyl, monocyclic heterocyclothio).

Representative examples of straight or branched lower alkylene $R^5$ include C1 to C5, preferably C1 to C3 alkylene.

Carboxy protective group $R^6$ is useful for carboxy-protection, or for medically useful derivative formation. The said $R^6$ groups are known in the field of penicillin and cephalosporin chemistry as those capable of being introduced or removed without adverse effect on other part of the molecule and having up to 19 C (for reaction or medical purpose, e.g., that forming medical salt, pharmaceutically active ester forming group). Representative are these for reaction including an ester forming group, C1 to C8 alkyl (e.g., methyl, methoxymethyl, ethyl, ethoxymethyl, iodoethyl, propyl, isopropyl, butyl, isobutyl, ethoxyethyl, methylthioethyl, methane sulfonylethyl, trichloroethyl, t-butyl), C3 to C8 alkenyl (e.g., propenyl, allyl, prenyl, hexenyl, phenylpropenyl, dimethylhexenyl), C7 to C19 aralkyl (e.g., benzyl, methylbenzyl, dimethylbenzyl, methoxybenzyl, ethoxybenzyl, nitrobenzyl, aminobenzyl, diphenylmethyl, phenethyl, trityl, di-t-butylhydroxybenzyl, phthalidyl, phenacyl), C6 to C12 aryl (e.g., phenyl, tolyl, xylyl, diisopropylphenyl, trichlorophenyl, pentachlorophenyl, indanyl), C1 to C12 N-substituted amino (ester group with e.g., acetoneoxime, acetophenoneoxime, acetaldoxime, N-hydroxysuccinimide, N-hydroxyphthalidmide, or the like), C3 to C12 hydrocarbylsilyl (e.g., trimethylsilyl, dimethylmethoxysilyl, t-butyldimethylsilyl), C3 to C12 hydrocarbylstannyl (e.g., trimethylstannyl) or the like protective groups. The protecting group may optionally be substituted with a group as given below. As the carboxy protecting group is removed by the time of forming the objective product, the structure of the protecting group is not important, if protection is effective and a wide range of equivalent groups (e.g., amide, anhydride with a carbonic acid or carboxylic acid) are available.

The said medical $R^6$ include, e.g., a salt-forming group, pharmaceutically active ester-forming group. Preferably, the salt forming $R^6$ can be pharmaceutically available ion-forming light metal of Group I to II, Period 2 to 4 in the Periodical table known in the penicillins and cephalosporins field and ammonio. Representative light metals include lithium, sodium, potassium, magnesium, calcium, aluminum, or the like. Ammonium salts are suitable for synthesis or storage. Representative are C1 to C12 alkylammonium (e.g., trimethylammonium, triethylammonium, methylmorpholinium) salts and C4 to C9 aromatic base (e.g., pyridinium, collidinium, picolinium, quinolinium, dimethylanilinium) salts.

Pharmaceutically active ester-forming $R^6$ is a group forming an ester showing antibacterial activity through enteral or parenteral administration. Representative are C2 to C15 1-oxygen substituted alkyl {alkanoyloxyalkyl (e.g., acetoxymethyl, pivaloyloxymethyl, cyclohexylacetoxyethyl), C3 to C15 alkoxycarbonyloxyalkyl (e.g., ethoxycarbonyloxyethyl, isopropoxycarbonyloxyethyl, cyclohexyloxycarbonyloxyethyl), C2 to C8 alkoxyalkyl (e.g., methoxymethyl), C4 to C8 2-oxacycloalkyl (e.g., tetrahydropyranyl), or the like}, C8 to C12 substituted aralkyl (e.g., phenacyl, phthalydyl), C6 to C12 aryl (e.g., phenyl, indanyl), or C2 to C12 alkenyl (e.g., allyl, (2-oxo-1,3-dioxolyl)methyl) esters.

The hydroxy-protecting group (e.g., for vic-hydroxyaroyl) can be an easily removable ester forming group [carboxylic acid acyl (e.g., C1 to C10 alkanoyl as formyl, acetyl, propionyl, pivaloyl, octyl; e.g., monocyclic aroyl as benzoyl, toluoyl, xyloyl), C2 to C10 carbonic acid acyl (e.g., C2 to C8 alkoxycarbonyl, benzyloxycarbonyl, p-methoxybenzyloxycarbonyl, p-ethoxybenzyloxycarbonyl, nitrobenzyloxycarbonyl, allyloxycarbonyl)], easily removable ether-forming group [C2 to C8 alkyl (e.g., t-butyl, tetrahydropyranyl, tetrahydrofuryl, methoxymethyl, methoxyethoxymethyl), C3 to C18 hydrocarbylsilyl (e.g., trimethylsilyl, triethylsilyl, dimethylphenylsilyl, diphenyl-t-butylsilyl, triphenylsilyl, dimethyl-t-pentylsilyl), or C7 to C19 reactive aralkyl (e.g., benzyl, p-methoxybenzyl, triphenylmethyl).

The counter-ion Y of the pyridinio can be organic or inorganic anion. Representative are anions of hydrochloric acid, hydrobromic acid, hydriodic acid, sulfuric acid, carboxylic acid, and sulfonic acid.

The said groups $R^1$ to $R^6$ may optionally have a substituent as follows. Said carbon numbers include that of substituent.

The phenolic group or enolated phenacyl group of compound (I) can form an alkali metal salt. When the molecule has amino, this can be protected to avoid adverse change during the reaction. This amino-protection is made with a C1 to C20 amino-protective group removable and introducable without adverse change in other part of the molecule. Representative are optionally further substituted C1 to C8 alkyl (e.g., t-butyl, methoxymethyl, methoxyethoxymethyl, trichloroethyl, tetrahydropyranyl), C7 to C20 aralkyl (e.g., benzyl, diphenylmethyl, trityl, methoxybenzyl, nitrobenzyl, methylbenzyl), C6 to C12 arylthio (e.g., nitrophenylthio), C1 to C8 alkylidene, C7 to C14 aralkylidene (optionally substituted benzylidene), acyl [C1 to C8 alkanoyl (e.g., formyl, acetyl, chloroacetyl, trichloroacetyl, trifluoroacetyl), C7 to C15 aroyl (e.g., benzoyl, nitrobenzoyl), C2 to C12 alkoxycarbonyl (alkyl part is e.g., methyl, ethyl, propyl, cyclopropylethyl, isopropyl, butyl, hexyl, isobutyl, trichloroethyl, pyridylmethyl, cyclopentyl cyclohexyl), C8 to C15 aralkoxycarbonyl (e.g., its aralkyl part is benzyl, diphenylmethyl, nitro benzyl), C3 to C10 dibasic acid acyl (e.g., succinyl, phthaloyl), halosulfonyl, C0 to C10 phosphoric acyl (e.g., dialkoxyphosphoryl, dichlorophosphoryl), C3 to C15 trialkylsilyl, C3 to C15 trialkylstannyl, and the like amino-protective groups.

Scope of Groups

The alkyl part of the said groups is straight, branched, or cyclic alkyl. Representative are C1 to C12 alkyl (e.g., methyl, ethyl, propyl, isopropyl, cyclopropyl, butyl, isobutyl, t-butyl, cyclobutyl, cyclopropylmethyl, pentyl, isopentyl, neopentyl, cyclopentyl, cyclopropylethyl, hexyl, cyclohexyl, cyclopentylmethyl, heptyl, cycloheptyl, cyclopentylethyl, cyclohexylmethyl, octyl, cyclooctyl, cyclohexylethyl, nonyl, dodecyl). These may optionally have an unsaturated bond or a substituent as given below.

The aralkyl part is a combination of said alkyl and aryl below. Representative is up to C14 aralkyl (e.g., benzyl, phenethyl, phenylpropyl, phenylisopropyl, diphenylmethyl, methoxydiphenylmethyl, naphthylmethyl, furylmethyl, thienylpropyl, oxazolylmethyl, thiazolylmethyl, imidazolylmethyl, triazolylmethyl, pyridylmethyl, indolylmethyl, benzoimidazolylethyl, benzothiazolylmethyl, quinolylmethyl). These may optionally have a substituent as given below.

The said acyl part has the structure as below. Representative are up to C14 acyl, for example, carboxylic acyl (e.g., straight branched or cyclic alkanoyl, mono- or bi-cyclic aroyl, aralkanoyl, or arylalkenoyl having optionally having a hetero atom), sulfonic acyl (e.g., alkylsulfonyl, arylsulfonyl), carbonic acid acyl (e.g., carbamoyl, carbalkoxy, carbaralkoxy), sulfo, and the like. These may optionally have a substituent as given below.

The said aryl part is monocyclic or dicyclic, five to six-membered carbocyclic or heterocyclic aryl. This heterocyclic group may have oxygen, nitrogen, or sulfur as heteroatoms. Representative are C1 to C10 heteroaryl (e.g., furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyrazinyl, quinolyl, pyridopyridyl) and carbocyclic aryl (e.g., phenyl, naphthyl, indenyl, indanyl, tetralinyl). These may optionally be substituted as given below.

Representative substituents to be attached to said groups include a carbon function (e.g., straight, branched or cyclic alkyl, alkenyl, alkinyl, aralkyl, aryl, heteroring group, carboxylic acid acyl, carbamoyl, carboxy, protected carboxy, cyano); nitrogen function (e.g., amino, acylamino, guanidyl, ureido, alkylamino, dialkylamino, isothiocyano, isocyano, nitro, nitroso); oxygen function (e.g., hydroxy, alkoxy, aryloxy, heterocyclooxy, cyanato, oxo, carboxylic acyloxy, sulfonic acyloxy, phosphoric acyloxy); sulfur function (e.g., mercapto, alkylthio, alkylsulfonyl, arylthio, aryl sulfonyl, heterocyclothio, heterocyclosulfonyl, acylthio, thioxo, sulfo, sulfamoyl); halogen (e.g., fluoro, chloro, bromo, iodo, pseudohalogeno); silyl (e.g., trialkylsilyl, dialkylalkoxysilyl); stannyl (e.g., trialkylstannyl); and the like.

Examples of the Claimed Compound

Representative free compounds (I) include the followings:

(1) Following betain and its sulfoxide:

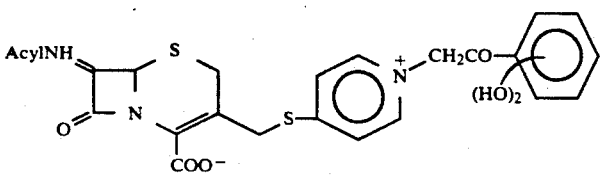

| Acyl group (Acyl) | Position of (OH)₂ |
| --- | --- |
| 1) Aroyl | |
| benzoyl | 2,3 |
| p-methylbenzoyl | 3,4 |
| 2,6-dimethoxybenzoyl | 2,3 |
| 5-phenyl-3-methyl-4-isoxazoylcarbonyl | 3,4 |
| 2) Alkanoyl | |
| formyl | 2,3 |
| acetyl | 2,3 |
| acetyl | 3,4 |
| phenoxyacetyl | 2,3 |
| phenoxyacetyl | 3,4 |
| difluoromethylthioacetyl | 2,3 |
| difluoromethylthioacetyl | 3,4 |
| cyanomethylthioacetyl | 2,3 |
| cyanomethylthioacetyl | 3,4 |
| aminoadipoyl | 2,3 |
| aminoadipoyl | 3,4 |
| 3) Aralkanoyl | |
| phenylacetyl | 2,3 |
| phenylacetyl | 3,4 |
| mandeloyl | 3,4 |
| α-(2-thienyl) acetyl | 3,4 |
| tetrazolylacetyl | 3,4 |
| phenylmalonyl | 2,3 |
| phenylmalonyl | 3,4 |
| α-sulfophenylacetyl | 3,4 |
| cyanoacetyl | 2,3 |
| cyanoacetyl | 3,4 |
| α-aminophenylacetyl | 3,4 |
| α-amino-p-hydroxyphenylacetyl | 3,4 |
| α-carbamoylamino-p-hydroxyphenylacetyl | 3,4 |
| α-(4-ethyl-2,3-dioxopiperazinylcarbonylamino)phenylacetyl | 3,4 |
| 4) thiazolyloximes | |
| 2-(2-amino-4-thiazolyl)-2-hydroxyiminoacetyl | 2,3 |
| 2-(2-amino-4-thiazolyl)-2-hydroxyiminoacetyl | 3,4 |
| 2-(2-amino-4-thiazolyl)-2-methoxyiminoacetyl | 2,3 |
| 2-(2-amino-4-thiazolyl)-2-methoxyiminoacetyl | 3,4 |
| 2-(2-amino-4-thiazolyl)-2-carboxymethoxyiminoacetyl | 2,3 |
| 2-(2-amino-4-thiazolyl)-2-carboxymethoxyiminoacetyl | 3,4 |
| 2-(2-amino-4-thiazolyl)-2-(1-carboxy-1-methylethoxyimino)-acetyl | 2,3 |
| 2-(2-amino-4-thiazolyl)-2-(1-carboxy-1-methylethoxyimino)-acetyl | 3,4 |
| 2-(5-amino-1,2,4-thiadiazol-3-yl)-2-methoxyiminoacetyl | 2,3 |
| 2-(5-amino-1,2,4-thiadiazol-3-yl)-2-methoxyiminoacetyl | 3,4 |
| 2-(5-amino-1,2,4-thiadiazol-3-yl)-2-hydroxyiminoacetyl | 3,4 |
| 2-(5-amino-1,2,4-thiadiazol-3-yl)-(1-carboxy-1-methylethoxyimino)acetyl | 3,4 |
| 5) carboxyacrylamides | |
| 2-(2-amino-4-thiazolyl)-4-carboxy-2-butenoyl | 2,3 |
| 2-(2-amino-4-thiazolyl)-4-carboxy-2-butenoyl | 3,4 |

-continued

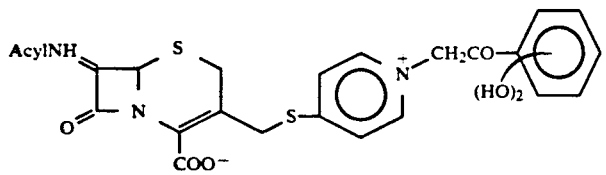

| Acyl group (Acyl) | Position of (OH)$_2$ |
|---|---|
| 2-(2-amino-4-thiazolyl)-5-carboxy-2-pentenoyl | 2,3 |
| 2-(2-amino-4-thiazolyl)-6-carboxy-2-hexenoyl | 3,4 |
| 2-(5-amino-1,2,4-thiadiazol-3-yl)-6-carboxy-2-hexenoyl | 3,4 |
| 6) Carbonic acyls | |
| tert-butoxycarbonyl | 2,3 |
| tert-butoxycarbonyl | 3,4 |
| trichloroethoxycarbonyl | 3,4 |
| benzyloxycarbonyl | 2,3 |
| benzyloxycarbonyl | 3,4 |
| methylbenzyloxycarbonyl | 2,3 |

(2) Following betain and its sulfoxide

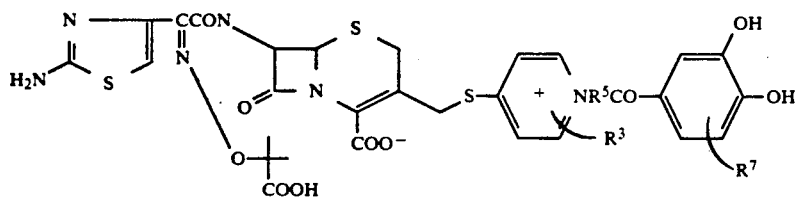

a) In above formula ($R^5$=CH$_2$, $R^7$=H), $R^3$ is methyl, dimethyl, trimethylene, or carbamoyl.

b) In above formula ($R^3$=H, $R^7$=H), and $R^5$ is ethylidene, propylidene, butylidene, isobutylidene, or cyclopropylmethylidene.

c) In above formula ($R^3$=H, $R^5$=CH$_2$), and $R^7$ is fluorine, chlorine, bromine, iodine, methyl, ethyl, isopropyl, hydroxy, methoxy, or acetoxy.

Related Technology

Among known cephalosporins having 3-alkylpyridiniothiomethyl, none has 3-vic-dihydroxyaroylmethylthiomethyl. The vic-dihydroxyaroyl is a specific anti-pseudomonal structure known since Japanese Patent Kokai SHO 52-85187 of this applicant. However, it is unknown as a substituent on 1-alkyl attached to 3-pyridiniothiomethyl.

Compounds (I) of this invention, for example a representative compound of this invention (I) (i.e., 3-[1'-(3,4-dihydroxyphenacyl)pyridinio-4-yl[thiomethyl-7β-[2-(2-aminothiazol-4-yl)-2-(1-carboxy-1-methylethoxy)imino]acetamido-3-cephem-4-carboxylate 1-oxide) is superior to chemically and antibacterially similar cephalosporins in a manner, for example, as follows:

UNOBVIOUSNESS (1): VS. OTHER ANTI-PSEUDOMONAL COMPOUND

The compound (I) of this invention is superior to other anti-pseudomonal cephalosporins as follows:

3-Pyridiniomethyl Compounds

The compound (I) having 3-vic-dihydroxyaroylmethylpyridiniothiomethyl has superior anti-pseudomonal activity to the compounds having 3-pyridiniomethyl. For example, MIC against ofloxacin resistant Pseudomonas aeruginosa SR 5018 of the representative (I) is 0.1 γ/ml, whereas that of the reference compound, ceftazidime is 25 γ/ml to show 250 times activity of the compound of this invention.

Ammoniomethyl Compounds

The compound (I) having 3-vic-dihydroxyaroylmethylpyridiniothiomethyl has superior anti-pseudomonal activity to the compounds having 3-ammoniomethyl. For example, MIC against ofloxacin resistant Pseudomonas aeruginosa SR 5018 of the representative (I) is 0.1 γ/ml, whereas that of the reference compound, E-1040: 3-(4-carbamoylquinuclidinio)methyl-7β-[2-(5-amino-1,2,4-thiadiazol-3-yl)-2-methoxyimino]-acetamido-3-cephem-4-carboxylate (Japanese Patent Kokai SHO 62-30786) is 6.3 γ/ml to show 63 times activity of the compound of this invention.

3-Alkylpyridiniothiomethyl Compounds

The compound (I) having 3-vic-dihydroxyaroylmethylpyridiniothiomethyl has superior anti-pseudomonal activity to the compounds having 3-alkylpyridiniothiomethyl. For example, MIC against ofloxacin resistant Pseudomonas aeruginosa SR 24 of the representative (I) is 0.1 γ/ml, whereas that of the reference compound having 3-methylpyridiniothiomethyl (Japanese Patent Kokai SHO 62-5961) is 25 γ/ml, the reference compound having 3-carbamoylmethylpyridiniothiomethyl (Japanese Patent Publication Kokai SHO 62-228085) is 12.5 γ/ml and the reference compound having 3-(1-carbamoylmethyl-2,3-trimethylenepyridinio-4-ylthiomethyl (Japanese Patent Kokai SHO 61-17589) is 6.3 γ/ml respectively to show 63 to 250 times activity of the compound of this invention.

UNOBVIOUSNESS (2): VS. OTHER CATECOLS

The compound (I) of this invention is superior to structurally closely related cephalosporin in anti-pseudomonal activity as follows:

3-Pyridiniomethyl Compounds

The compound (I) having 3-dihydroxyaroylmethylpyridiniothiomethyl has superior anti-pseudomonal activity to the compound having 3-pyridiniomethyl. For example, MICs against *Escherichia coli* SR 5082 and *Pseudomonas aeruginosa* SR 5018 of the representative (I) are 0.2 γ/ml and 0.1 γ/ml, whereas that of the reference compound, BO-1341: 3-(6,7-dihydroxyisoquinolinio)methyl-7β-(2-(2-aminothiazol-4-yl))-2-(1-carboxy-1-methylethoxyimino)acetamido)-3-cephem-4-carboxylate (Japanese Patent Kokai SHO 63-10793) are 1.6 γ/ml and 0.4 γ/ml to show 4 to 8 times activity of the compound of this invention.

3-Dihydroxybenzyl Compounds

The compound (I) having 3-vic-dihydroxyaroylmethylpyridiniothiomethyl has superior anti-pseudomonal activity to the compound having 3-dihydroxybenzyl. For example, MIC against *Pseudomonas aeruginosa* SR 24 of said representative compound (I) is 0.1 γ/ml and $ED_{50}$ for preventing infection is 1.35 mg/kg whereas MIC of the reference compound having 3-(3,4-dihydroxybenzyl) (Japanese Patent Kokai SHO 62-209082) is 0.2 γ/ml and its $ED_{50}$ is 3.4 mg/kg to show 2 to 2.5 times activity of the compound of this invention.

Thiadiazolylthiomethyl Compounds

The compound (I) having 3-vic-dihydroxyaroylmethylpyridiniothiomethyl has superior anti-Pseudomonal activity to the compound having 3-dihydroxyphenylheterocyclothiomethyl. For example, $ED_{50}$ against *Pseudomonas aeruginosa* SR 24 of said representative compound (I), its 1-sulfide, and its 2,3-trimethylenepyridinio analogue each is 1.35 to 6.27 mg/kg, whereas that of the reference compound having 3-(3,4-dihydroxyphenyl)thiazolythiomethyl (Japanese Patent Kokai SHO 63-185985) is 16.3 mg/kg to show 2.6 to 12 times activity of the compound of this invention.

Dihydroxybenzoylaminomethyl Compounds

The compound (I) having 3-vic-dihydroxyaroylmethylpyridiniothiomethyl is superior to the compound having 3-vic-dihydroxybenzoylaminomethyl in antibacterial activity against Enterobacter bacteria.

UNOBVIOUSNESS (3): VS. STRUCTURALLY RELATED COMPOUNDS

The compound (I) of this invention is superior to structurally closely related novel dihydroxyarylpyridiniothiomethylcephalosporins in anti-pseudomonal activity as follows:

Benzylpyridiniothiomethyl Compounds

The compound (I) having 3-vic-dihydroxyaroylmethylpyridiniothiomethyl is superior in anti-pseudomonal activity to the compound having 3-dihydroxybenzylpyridiniothiomethyl. For example, MIC against *Pseudomonas aeruginosa* SR 24 of said representative compound (I) and its 2,3-trimethylenepyridinio analogue each is 0.05 to 0.2 γ/ml, whereas that of a novel reference compound having 3-(3,4-dihydroxybenzylpyridiniothiomethyl) is 0.4 to 0.78 γ/ml to show 2 to 16 times activity of the compound of this invention. Further, $ED_{50}$ against *Pseudomonas aeruginosa* SR 24 of said representative compound (I) and its 2,3-trimethylenepyridinio analogue each is 2.90 to 6.27 mg/kg, whereas that of a novel reference compound having 3-(3,4-dihydroxybenzylpyridiniothiomethyl) is 9.13 to 16.3 mg/kg to show 2.6 to 3.2 times activity of the compound of this invention.

Use

The compounds (I) show potent antibacterial activity against aerobic and anaerobic Gram-positive (e.g., *Staphylococcus aureus*), and Gram-negative bacteria (e.g., *Escherichia coli*). Especially, the compounds are characteristic in 1) a high antibacterial activity against a wide range of Gram-negative bacteria, for example, *Pseudomonas aeruginosa* (e.g., $ED_{50}$ SR 4967 (mouse)=3.64 mg/kg), *Serratia marsescense* (e.g., $ED_{50}$ A 13880 (mouse)=0.07 mg/kg), clinically isolated *Morgania morganii*, clinically isolated *Enterobacter cloacae*, and clinically isolated *Clostridium freundii*, (2) a high blood level intergral in monkey (AUC=0.0731 mg. min/ml).

3) superior characters, e.g., a long action shown by large $T_{\frac{1}{2}}$, high level of the compound in the exudate percolated into artificial pouch made in muscle, high urinary excretion.

Utilizing said antibacterial activity of compound (I), this invention provides the following uses (1) to (4).

(1) A bactericidal or bacteriostatic method by bringing Compound (I) into contact with a sensitive bacteria.

(2) A method for disinfecting, killing bacteria, preventing bacterial growth, and preventing perishing of a material by applying compound (I) to a portion where sensitive bacteria are growing or supposed to grow.

(3) A method for preventing or treating an infection caused by sensitive bacteria and for promoting growth by administering compound (I) singly or in admixture with other medicals to a human or animal. For example, this invention also provides a method for treating or preventing human or veterinary bacterial infections caused by sensitive bacteria (e.g., respiratory tract infection, nasopharyngitis, rhinitis, empyema, tonsillitis, pharyngitis, bronchitis, pneumonia, pneumonitis, urinary tract infection, pyelonephritis, dermatitis, ulceration, pustulosis, abscess, ear infection, digestive tract infection, osteomyelitis, septicemia, wound and soft tissue infection, post operative infection, gynecological infection) by administering an effective amount of the said compound (I) at an effective daily dose of 0.1 to 6 gram (injection), 0.4 to 4 gram (orally), or 0.01 to 10 mg (topically).

(4) A use of compound (I) as a starting material for producing other antibacterials and a material for sensitivity test of bacteria.

Composition

This invention also provides an antibacterial pharmaceutical formulation containing said compound (I). This is provided in various dosage forms (e.g., solution, dispersion, or suspension) containing 0.01 to 99% of compound (I) solely or in admixture with a conventional carrier for solid or liquid compositions.

The composition of compound (I) as a free acid or light metal salt is available by formulating in a conventional manner if required with a carrier to give injection (e.g., ampoule, vial, solution, or suspension, for intravenous, intramuscular, or subcutaneous injection, drip), external medicine, topical medicine (e.g., ear-, nose-, or eye-lotion, ointment, emulsion, spray, suppository), oral medicine (with a enteral adsorption-promoting agent), or the like. The pharmaceutically active ester of compound (I) is used as, e.g., injection, exteral or topical medicine, enteral medicine. The composition of compound (I) as a free acid or light metal salt may be a solid preparation (e.g., capsule, dry syrup, granule, lyophilized material, pellet, pill, powder, suppository, troche, tablet) or liquid preparation (e.g., dispersion, elixir, emulsion, inhalant, injection, ointment, suspension, syrup, solution). The capsule, granule, and tablet may be coated. They can be in a unit dosage form. The carrier is that available pharmacologically and pharmaceutically inert to the compound (I).

Representative examples of such carrier include, among others, for a solution, a solvent (e.g., alcohol, buffer, methyl oleate, water), buffer, dispersing agent, solubilizing agent, preservative (e.g., methyl or ethyl p-hydroxybenzoate, sorbic acid), absorption promoter (e.g., glycerin mono- or di-octanoate), antioxidant, aromatic substance, analgesic, emulsifying agent, suspending agent, an agent for controlling side effects or enhancing the activity (e.g., absorption or excretion controlling agent, enzymatic decomposition preventing agent, $\beta$-lactamase inhibiting agent, other antibacterial) or the like. The pharmaceutical preparation can be prepared conventionally.

Preparation

This invention provides a method for producing compound (I). For example, the objective compounds can be prepared as follows from a known substance.

Amide Formation

The objective compound (I) or its derivatives can be prepared by reacting amine (II) or its reactive derivative with carboxylic acid (III) or its reactive derivative in a conventional manner as follows:

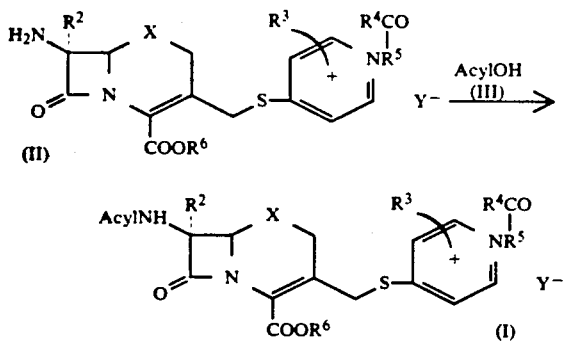

(Acyl is acyl of acylamino $R^1$)

The said reactive derivative of amine (II) is that in which the 7-amino is activated with C1 to C10 groups, for example, silyl (e.g., trimethylsilyl, methoxydimethylsilyl, t-butyldimethylsilyl), stannyl (e.g., trimethylstannyl), alkylene forming enamine of said amino (with e.g., alkanal, acetone, acetylacetone, acetoacetate, acetacetanilide, acetoacetonitrile, cyclopentanedione, acetylbutyrolactone), alkylidene (e.g., 1-haloalkylidene, 1-haloaralkylidene, 1-alkoxyalkylidene, 1-alkoxyaralkylidene, 1-alkoxy-1-phenoxyalkylidene, alkylidenne, aralkylidene), acid (as a salt with, e.g., a mineral acid, carboxylic acid, sulfonic acid), easily removable acyl (e.g., alkanoyl), or the like and that in which other functional group is protected.

Carboxylic acid (III) is reacted in the presence of a condensing reagent [carbodiimide (e.g., N,N'-diethylcarbodiimide, N,N'-dicyclohexylcarbodiimide), carbonyl compound (e.g., carbonyldiimidazole), isoxazolinium salt, acylamino compound (e.g., 2-ethoxy-1-ethoxycarbonyl-1,2-dihydroquinoline), or the like]. The reaction is preferably carried out in a solvent having no reactive hydrogen with 1 to 2 mole of carboxylic acid (III) and 1 to 2 mole of condensing reagent per mole of amine (II).

Typical reactive derivative (III) is acid anhydride symmetric acid anhydride, mixed acid anhydride [mineral acid (e.g., phosphoric acid, sulfuric acid, carbonic acid half ester), mixed acid anhydride with organic acid (e.g., alkanoic acid, aralkanoic acid, sulfonic acid), or the like], intramolecular anhydride (e.g., ketene, isocyanate), acid halide (i.e., mixed anhydride with hydrogen halide)], acid halide, reactive ester [enol ester (e.g., vinyl, isopropenyl ester), aryl ester (e.g., phenyl, halophenyl, nitrophenyl ester), hetero ring ester (e.g., pyridyl, benzotriazolyl ester), ester with an N-hydroxy compound (e.g., ester with diacylhydroxylamine, N-hydroxysuccinimidoyl ester, N-hydroxyphthalimidoyl ester), thiol ester (e.g., aralkylthiol, heteroringthiol ester) or the like], reactive amide [aromatic amide (e.g., amide with imidazole, triazole, 2-ethoxy-1,2-dihydroquinoline), diacylanilide, or the like], and other reactive derivatives. These reactive derivatives are used in the presence of an acid scavenger [inorganic base (e.g., oxide, hydroxide, carbonate, bicarbonate, etc., of, e.g., alkali metal, alkaline earthmetal), organic base (e.g., t-amine, aromatic base), oxirane (e.g., alkylene oxide, aralkylene oxide), pyridinium salt (e.g., tripyridiniotriazine trichloride), adsorbent (e.g., Celite), or the like]. This reaction is preferably carried out in a solvent having no reactive hydrogen with 1 to 2 mole of carboxylic acid (III) reactive derivative and 0 to 2 mole of acid scavenger per mole of amine (II). Acid halide, enzymatically reactive ester can be treated in an aqueous solvent.

Amide Cleavage

The amido compound (I) may be cleaved easily to give the corresponding 7-amino compound by reacting in a conventional aprotic solvent (e.g., halohydrocarbon) successively with phosphorus pentachloride at $-20°$ to $50°$ C. for 1 to 5 hours giving iminochloride, with alcohol (e.g., methanol, ethanol, propanol) at $-60°$ to $-20°$ C. for 10 to 90 minutes giving imino ether, and with acid giving the amine. The yield may be improved by adding side reaction-preventing agent (e.g., secondary amine).

Protection of Carboxy

A compound (I) having $R^6$ as ester-forming group can be produced by esterifying in an inert solvent at $0°$ C. to $50°$ C. the free acid or its reactive derivative (anhydried, salt, halide, reactive ester), for example, by a conventional method as follows:

a) A reaction of the alcohol of the ester-forming $R^6$ with the carboxylic acid or its reactive derivative in the presence of an acid scavenger or condensing reagent as above in the amide formation.

b) A reaction of the halide, sulfonate, or the like of the ester-forming $R^6$ with the carboxylic acid or its reactive derivative in the presence of an acid scavenger.

c) A reaction of a diazo compound of the ester-forming $R^6$ with the carboxylic acid at $0°$ C. to $50°$ C.

Deprotection of Protected Carboxy

A compound (I) having a carboxy-protective group can be deprotected conventionally in an inert solvent to give carboxylic acid (I). This deprotection includes, for example, as follows:

a) A highly reactive ester as carboxy-protective $R^6$ can be deprotected by contacting it with acid, base, buffer solution, ion-exchange resin, or the like in an inert solvent. Some insufficiently reactive ester-forming groups may be activated conventionally to easily be deprotected (for trichloroethyl ester with metal and acid; for p-nitrobenzyl ester by hydrogenation, dithionate, or metal and acid; and for phenacyl ester by irradiation);

b) An aralkyl as a carboxy-protective $R^6$ can be deprotected by a conventional hydrogenation in the presence of a catalyst (e.g., palladium, platinum, nickel);

c) A t-alkyl, cyclopropylmethyl, 2-alkenyl, aralkyl, sulfonylethyl, or the like as carboxy-protective $R^6$ may be deprotected by treating, for example, with a mineral acid, Lewis acid (e.g., aluminum chloride, tin tetrachloride, titanium tetrachloride), sulfonic acid (e.g., benzenesulfonic acid, methanesulfonic acid, trifluoromethanesulfonic acid), strong carboxylic acid (e.g., trifluoroacetic acid), or the like, if required in the presence of a cation scavenger (e.g., anisole, benzenethiol);

d) A 2-alkenyl as carboxy-protective $R^6$ can be deprotected by the action of triarylphosphine-palladium complex;

e) A phenacyl, 2-alkenyl, hydroxyaralkyl, or the like as carboxy-protective $R^6$ can be deprotected by the action of a base or nucleophilic reagent; or f) Other equivalent deprotections of carboxy-protective group.

Carboxylic Acid Salt

A free acid compound (I) is treated with a base or its salt with weak acid to give the corresponding salt (I). For example, by neutralizing the free acid with a base (e.g., light metal hydroxide, carbonate, hydrogen carbonate) or by treating with light metal lower carboxylate (e.g., sodium acetate, sodium lactate, sodium 2-ethylhexanoate) by exchange decomposition in a polar organic solvent (e.g., alcohol, ketone, ester) and then diluting with a sparingly dissolving solvent to separate the salt, or lyophilizing the salt solution. The reaction completes usually 1 to 10 minutes at lower than 50° C., but the mixture may be kept longer if no adverse side reaction occurs.

Pyridiniothio Introduction

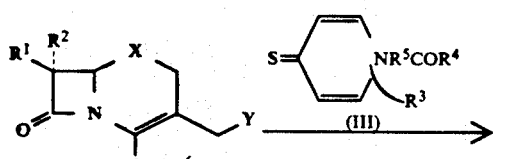

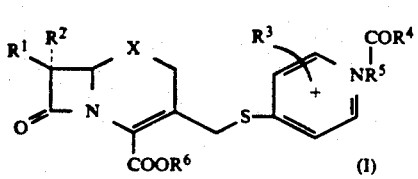

Compound (I) can be produced by treating 3-leaving group substituted methyl starting compound (II) with the corresponding thiopyridone (III) to give compound (I).

Preferable leaving group Y includes reactive group (e.g., halogen, sulfonyloxy, alkanoyloxy, dihaloacetoxy, trihaloacetoxy). The reaction proceeds in a dry or aqueous solvent at 0° to 60° C. satisfactorily.

Pyridinio Formation

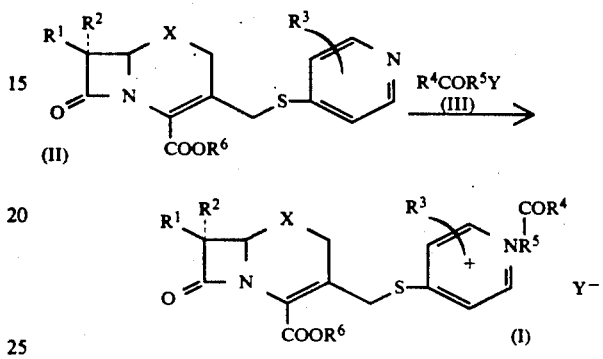

vic-Dihydroxyaroylalkylpyridiniothiomethyl compound (I) can be produced by treating 3-pyridylthiomethyl compound (II) conventionally with the corresponding vic-di(protected or free)-hydroxyaroylalkylating reagent (III) in high yield. The reaction completes at 0° to 50° C. for about 30 minutes to 5 hours.

Oxidation to Sulfoxide

Compound (I) having a sulfide in its molecule can be oxidized conventionally, for example, with the following oxidizing reagent to give the corresponding sulfoxide (I). Thus, compound (I) where X is sulfur atom is treated with following oxidizing reagent (e.g., hydrogen peroxide, ingorganic peracid, percarboxylic acid) preferably in an inert solvent (e.g., halohydrocarbon, ester, water) to give the corresponding sulfoxide (I):

a) Peracid (industrially available permineral acid, percarboxylic acid, persulfonic acid, or the like);

b) Ozon;

c) Hydrogen peroxide; or d) Peroxide (e.g., boron peroxide, nickel peroxide, sodium peroxide, urea peroxide).

Preferably, the starting compound (I) is oxidized with 1 to 2 molar equivalent of an oxidizing reagent at 0° to 35° C. for 1 to 20 hours to give the sulfoxide. The reaction can be carried out, if required, in the presence of a reaction promoting reagent (e.g., phosphoric acid, polyphosphoric acid, phoshoric acid monoester, alkanoic acid, a salt of acid of Group VII atom (wolfrum)) in the Periodical Table. When the starting compound has a double bond at position 2, it migrates to position 3.

Reduction of Sulfoxide

Compound (I) having sulfoxide in the molecule can be reduced conventionally to give the corresponding sulfide (I). Thus, compound (I) having sulfinyl as X is treated with 2 to 5 molar equivalents of a reducing reagent (e.g., trivalent phosphous or stannous compound, iodide) in an inert solvent (dimethylformammide, dichloromethane, dioxane) at −20° to 50° C. for 2 to 50 hours to give the corresponding sulfide (I).

Protection of Hydroxy

Hydroxy including phenolic hydroxy can be protected by introducing an acyl or ether type protective group, by the conventional action of protective reagent (e.g., halogenide, anhydride, reactive ester of the acyl or ether-type protective group), if required in the presence of an acid scavenger (e.g., aromatic base, alkali metal hydroxide, alkaline earth metal hydroxide, alkali metal carbonate, alkaline earth metal carbonate, alkali metal bicarbonate, alkaline earth metal bicarbonate).

Deprotection of the Protected Hydroxy

Hydroxy protective group can be deprotected by a method as above under the title of deprotection of carboxy-protective group. For example, by the action of a strong carboxylic acid, Lewis acid, if required in the presence of cation scaventer to cleave ether bond, by the action of acid or base to hydrolyze ester, or the like. A protective group of a phenolic hydroxy can easily be deprotected.

These groups and its introduction and elimination can be done by applying conventional methods.

Other Productions

The compounds having 1-(2-(dihydroxyphenyl)-2-hydroxyethyl)pyridiniothiomethyl at position 3 gives the corresponding compound (I) by oxidation.

When the 7-side chain is 2-aminothiazolyl-2-substituted oxyiminoacetoamido, the compound (I) can be prepared conventionally by the ring closure of the aminothiazole ring from the corresponding haloacetoacetoamido compound and thiourea, oxime formation from the corresponding 2-oxoacetoamido compound and hydroxylamine, or the like.

Protection of Amino

To amino of compound (I) can be introduced a conventional protective group under a condition as follows:

a) Alkoxycarbonyl, aralkoxycarbonyl, alkanoyl, or the like by the action of the halogenide, anhydride, etc. of the group (preferably 1 to 5 equivalents) in the presence of an acid scavenger at $-30°$ to $50°$ C.

b) Alkoxycarbonyl, aralkoxycarbonyl, alkanoyl, arylsulfenyl, aralkyl, trialkylsilyl, trialkylstannyl, or the like by the action of halide of the group (1 to 5 equivalents) in the presence of an acid scavenger (1 to 10 equivalents) in a solvent at $-30°$ to $100°$ C. for 1 to 10 hours.

c) Trialkylsilyl by the action of a reactive derivative, disilazane compounds, acetoamide compounds, halogenides (e.g., hexamethyldisilazane, bistrimethylsilylacetamide, trimethylsilyl chloride) in a conventional manner.

Deprotection of Protected Amino

Compound (I) having protected amino in the molecule can be deprotected, for example, as follows:

a) Alkoxycarbonyl (e.g., t-butoxycarbonyl), or the like amino protective group by the action of a strong acid (e.g., trifluoroacetic acid, trifluoromethanesulfonic acid), Lewis acid (e.g., aluminum chloride, stannic chloride, titanium chloride, zinc chloride), and other acids, if required in the presence of a cation scavenger (e.g., anisole, benzenethiol).

b) Aralkoxycarbonyl (e.g., carbobenzoxy, methylcarbobenzoxy, diphenylmethoxycarbonyl) or the like amino protective group by the action of the said Lewis acid and cathion scavenger or by hydrogen (e.g., catalytic hydrogenation using palladium or nickel catalyst).

c) Lower alkanoyl (e.g., formyl, acetyl, chloroacetyl), Schiff base forming group (a divalent carbon group, e.g., ethylidene, propylidene, benzylidene, substituted benzylidene), aralkyl (e.g., trityl, substituted trityl), arylthio (e.g., phenylsulfenyl), silyl or stannyl (e.g., trimethylstannyl, trimethylsilyl), or the like amino protective group by the action of acid (e.g., hydrochloric acid, sulfuric acid, methanesulfonic acid), or the like.

d) Methods specific for each protective group (for example, thiourea or N-alkyldithiocarbamate for haloacetyl; hydrazine for dibasic acid acyl; phosphorus pentachloride and alkanol for amide).

Reaction Conditions

The said syntheses each is usually carried out at $-30°$ C. to $100°$ C., especially $-20°$ C. to $50°$ C., for 10 minutes to 10 hours. If required, these are carried out under dry condition or inert gas atmosphere in a solvent with stirring, or the like conventional condition.

Reaction Solvent

The reaction solvent for this invention can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or the like industrial solvent or a mixture.

Work Up

The objective products can be recovered from the reaction mixture after removing contaminants (e.g., unreacted starting material, by-products, solvents) by a conventional method (e.g., evaporating, extracting, washing, concentrating, precipitating, filtrating, drying) and purified by a usual work up (e.g., adsorbing, eluting, distilling, precipitating, separating, chromatographying).

EXAMPLES

The following examples illustrate the present invention.

The physical constants of the products are summarized in tables. In the table, IR data shows the wave number in cm$^{-1}$, MNR data shows chemical shift $\delta$ in ppm and coupling constants J in Hz. In NMR data when a signal splitts and the ratio of the areas corresponds to the amount of the structure and the total corresponds to a group, each chemical shifts are shown with comma (,) and number of splitting is shown before signal type with the mark (x).

In the Examples, the part showing amount parts by weight of the starting $\beta$-lactam and equivalents shows that per mole of the starting $\beta$-lactam.

| Abbreviations | |
|---|---|
| (groups) | |
| Ac: acetyl. | BOC: tert-butoxycarbonyl. |
| tBu: tert-butyl. | BH: diphenylmethyl. |
| Me: methyl. | Ph: phenyl. |
| PMB: p-methoxybenzyl. | Tr: trityl. |
| MO (in column X): X: O, $R^2$: methoxy. | |
| (solvent) | |
| DCM: dichloromethane. | DMA: dimethylacetoamide. |
| DMF: dimethylformamide. | TFA: trifluoroacetic acid. |
| (Others) | |
| $ED_{50}$: 50% effective dose. | Eq.: equivalent. |
| MIC: minimal inhibitory concentration. | |
| min.: minute. | mMol.: millimole. |
| mol.: mole. | o.n.: overnight. |
| r.t.: room temperature. | temp.: temperature. |

Column $R^1$

G: phenylacetoamido.
FMOX: difluoromethylthioacetoamido.
CTX: 2-(2-amino-4-thiazolyl)-2-methoxyiminoacetoamido.
CAZ: 2-(2-amino-4-thiazolyl)-2-(1-carboxy-1-methylethoxyimino)acetamido
CETB: 2-(2-amino-4-thiazolyl)-4-carboxy-4-methyl-2-penteneamido.
BOCCTX: 2-(2-tert-butoxycarbonylamino-4-thiazolyl)-2-methoxyiminoacetoamido.
CAZtBu: 2-(2-amino-4-thiazolyl)-2-(1-tert-butoxycarbonyl-1-methylethoxyimino)acetoamido.
BOCCAZtBu: 2-(2-tert-butoxycarbonylamino-4-thiazolyl)-2-(1-tert-butoxycarbonyl-1-methylethoxyimino)acetoamido.
BOCCAZBH: 2-(2-tert-butoxycarbonylamino-4-thiazolyl)-2-(1-diphenylmethoxycarbonyl-1-methylethoxyimino)acetoamido.
BOCCETBBzl: 2-(2-tert-butoxycarbonylamino-4-thiazolyl)-4-benzyloxycarbonyl-4-methyl-2-pentenamido.

Column $R^4$ 2,3-OH: 2,3-dihydroxyphenyl.
3,4-OH: 3,4-dihydroxyphenyl.
3,4-OH-6-Me: 3,4-dihydroxy-6-methylphenyl.
3,4-OH-2-Cl: 3,4-dihydroxy-2-chlorophenyl.
3,4-OH-5-Cl: 3,4-dihydroxy-5-chlorophenyl.
3,4-OH-6-Cl: 3,4-dihydroxy-6-chlorophenyl.
3,4-OH-2,5-Cl: 3,4-dihydroxy-2,5-dichlorophenyl.
3,4-OHHR: 3,4-dihydroxyphenyl ($R^3$=2,3-trimethylene).
3,4-OH-α-Me: 3,4-dihydroxyphenyl ($R^5$=ethylidene).
3,4-OAc: 3,4-diacetoxyphenyl.
3,4-OAcHR: 3,4-diacetoxyphenyl ($R^3$=2,3-trimethylene).
3,4-OAc-α-Me: 3,4-diacetoxyphenyl ($R^5$=ethylidene).
2,3-PMB: 2,3-di-p-methoxybenzyloxyphenyl.
3,4-PMB: 3,4-di-p-methoxybenzyloxyphenyl.
3,4-PMB-6-Me: 3,4-di-p-methoxybenzyloxy-6-methylphenyl.
3,4-PMB-2-Cl: 3,4-di-p-methoxybenzyloxy-2-chlorophenyl.
3,4-PMB-5-Cl: 3,4-di-p-methoxybenzyloxy-5-chlorophenyl.
3,4-PMB-6-Cl: 3,4-di-p-methoxybenzyloxy-6-chorophenyl.

EXAMPLE 1

Amidation

According to above scheme, 7β-amino compound (2) (1 mole) is amidated with carboxylic acid of 7-side chain (3) or its reactive derivative in a following manner to give amide (1) as listed in Tables.

1) By stirring in a mixture of dichloromethane (10 Vol.), N,N-dicyclohexylcarbodiimide (1.1 Eq.), 2-ethoxy-1-ethoxycarbonyl-1,2-dihydroquinoline (1.1 Eq.), pyridine (1.5 Eq.) and carboxylic acid (3) (1.1 Eq.) at 0° C. to room temperature for 1 to 6 hours.

2) By stirring in a mixture of ethyl acetate (10 Vol.), di-2-pyridyl disulfide (1.1 Eq.), triphenylphosphine (1.1 Eq.), carboxylic acid (3) (1.1 Eq.) at 10° to 50° C. for 2 to 6 hours.

3) By stirring in a mixture of dichloromethane (3 Vol.), carboxylic acid (3) (1.1 Eq.), 1,3,5-tripyridiniotriazine trichloride (4 Eq.) at −10° to 10° C. for 1 to 5 hours.

4) By standing in a mixture of carbon tetrachloride (30 Vol.), N-methylmorpholine (1.5 Eq.), trisdiethylaminophosphine (1.1 Eq.), carboxylic acid (3) (1.1 Eq.) at −20° to 10° C. for 1 to 5 hours.

5) By stirring in a mixture of chloroform (10 Vol.), dimethoxyethane (10 Vol.), triethylamine (1.5 Eq.) and a mixed anhydride of carboxylic acid (3) and isobutoxyformic acid at −5° to 10° C. for 0.5 to 6 hours.

6) By heating in a refluxing mixture of ethyl acetate (10 Vol.), dichloroethane (10 Vol.), N-methylmorpholine (1.5 Eq.), symmetric anhydride of carboxylic acid (3) (1.1 Eq.) for 10 minutes to 2 hours.

7) By stirring in a mixture of dichloromethane (10 Vol.), pyridine (1.5 moles), and a mixed anhydride of carboxylic acid (3) and methanesulfonic acid warming from −70° C. to room temperature for 1 to 3 hours.

8) By stirring in a mixture of ethyl acetate (10 Vol.), a mixed anhydride of diethyl phosphate and carboxylic acid (3) (1.5 Eq.), and pyridine (1.5 Eq.) at 0° to 10° C. for 1 to 5 hours.

9) By stirring in a mixture of ethyl acetate (10 Vol.), dichloromethane (10 Vol.), N-methylmorpholine (1 Eq.), a mixed anhydride of carboxylic acid (3) and phosphoric acid dichloride at 0° C. to room temperature for 1 to 3 hours.

10) By stirring in a mixture of lutidine (1.5 Eq.), dichloromethane (10 Vol.), a mixed anhydride of phosphoric acid dimethylamide monochloride and carboxylic acid (3) (1.1 to 2 Eq.) at 0° to 30° C. for 1 to 4 hours.

11) By stirring in a mixture of dichloromethane (5 Vol.), trifluoroacetic acid anhydride (1.5 Eq.), pyridine (3 Eq.) and carboxylic acid (3) (1.5 Eq.) at 0° C. to room temperature for 1 to 5 hours.

12) By stirring in a mixture of dichloromethane (10 Vol.), diethyl phosphate bromide (1.2 Eq.), N-methylmorpholine (2.5 Eq.), and carboxylic acid (3) (1.2 Eq.) at 0° C. to room temperature for 1 to 3 hours.

13) When 4-carboxy of the compound (2) is free, this is dissolved in water (10 Vol.) containing aqueous sodium hydrogen carbonate (2.5 Eq.), mixed with carboxylic acid (3) chloride (1.1 Eq.) at −5° C. to room temperature for 30 minutes to 2 hours.

14) When 4-carboxy of the compound (2) is free, this is treated with trimethylsilyl chloride and triethylamine (1.2 Eq. each) to O-silylate, treated with pyridine (4 Eq.) and carboxylic acid (3) chloride (1.1 Eq.) at −30° C. for 30 minutes to 2 hours, and then hydrolized the silyl group with acid.

15) By stiiring in a solution of picoline (4 Eq.), carboxylic acid (3) chloride (1.2 Eq.), and dichloromethane (20 Vol.), 0° to −30° C. for 30 minutes to 2 hours.

16) By stirring in a mixture of dimethylformamide (2 Vol.), ethyl acetate (10 Vol.), triethylamine (1.1 Eq.) and carboxylic acid (3) chloride (1.1 Eq.) at 0° to 20° C. for 30 minutes to 3 hours.

17) By stirring in a mixture of dichloromethane (30 Vol.), cyanuric chloride (11 Eq.), pyridine (4 Eq.), and carboxylic acid (3) (1.1 Eq.), at −30° to 10° C. for 5 minutes to 2 hours.

18) By stirring in a mixture of dichloromethane (3 Vol.), phosphorus oxychloride (1.1 Eq.), and triethylamine (1.5 Eq.), carboxylic acid (3) (1.1 Eq.), −10° to 10° C. for 20 minutes to 2 hours.

19) Amine (1) is treated with trimethylsilyl chloride and an acid scavenger to give N-trimethylsilylated compound (2). By treating this with phosphorus oxychloride (1.5 Eq.), carboxylic acid (3) (1.2 Eq.), and dimethylaniline (4 Eq.) in dichloromethane (5 Vol.) at 0° C. to room temperature for 30 minutes to 2 hours.

20) By stirring in a mixture of dichloromethane (8 Vol.), thionyl chlolide (1.5 Eq.), pyridine (2.5 Eq.), and carboxylic acid (3) (1.1 Eq.) at −30° to 0° C. for 1 to 5 hours.

21) By stirring in a mixture of chloroform (3 Vol.), toluene (1 Vol.), carboxylic acid (3) (1.1 Eq.), picoline (2 Eq.), oxalyl chloride (1 Eq.) at −50° to 10° C. for 10 minutes to 2 hours.

22) By stirring in a mixture of dichloromethane (20 Vol.), pyridine (3 Eq.), carboxylic acid (3) 1-oxybenzotriazolyl ester (3 Eq.) at 10° to 50° C. for 5 to 30 hours.

23) By stirring in a mixture of dichloromethane (20 Vol.), 1-ethoxycarbonyl-2-ethoxy-1,2-dihydroquinonine (2.1 Eq.), N,N'-dicyclohexylcarbodiimide (2.5 Eq.) and carboxylic acid (3) (2 Eq.) at room temperature for 1 to 15 hours.

24) By stirring in a mixture of carboxylic acid (3) phthalimidoyl ester (2 Eq.) and dioxane (10 Vol.), at 10° to 50° C. for 2 to 8 hours.

25) By stirring in a mixture of carboxylic acid (3) succinimidoyl ester (1.5 Eq.) and methyl isobutyl ketone (10 Vol.) at 0° to 40° C. for 2 to 9 hours.

26) By stirring in a mixture of carbonyldiimidazole (1.1 Eq.), tetrahydrofuran (10 Vol.), dimethylacetamide (5 Vol.), and carboxylic acid (3) (1.1 Eq.) at 0° C. to room temperature for 1 to 5 hours.

27) By stirring in a mixture of dimethylformamide (5 Vol.), dimethylaniline (1.3 equivalents), carboxylic acid (3), the Vilsmeyer reagent of dimethylformamide (1.1 Eq.), and dimethylaniline (1.3 Eq.) at room temperature for 1 to 5 hours.

28) By heating in a mixture of dichloromethane (10 Vol.), dimethylformamide (5 Vol.), N,N-dicyclohexylcarbodiimide (1.1 Eq.), picoline (1.2 Eq.), carboxylic acid (3) (1.1 Eq.), for 2 to 24 hours.

29) To a solution of 7β-amino-3-[1-(3,4-dihydroxyphenacyl)-4-pyridiniothiomethyl-3-cephem-4-carboxylic acid p-methoxybenzyl ester hydrochloride (1.00 g; 1.5 mMol.) in dichloromethane (10 ml) at 0° C. are added N-methylmorpholine (0.16 ml; 1 Eq.) and 2-(2-t-butoxycarbonylamino-4-thiazolyl)-2-(1-t-butoxycarbonyl-1-methylmethoxyimino)acetic acid (0.84 g; 1.3 Eq.). The mixture is cooled to −40° C., mixed with phenyl phosphate dichloride (0.29 g; 1.3 Eq.) and N-methylmorpholine (0.49 ml; 3 Eq.) and stirred at −40° to −25° C. for 1 hour. The reaction mixture is diluted with water and the separating organic layer is taken, washed with hydrochloric acid and water, dried and concentrated under reduced pressure. The residue is washed with ether to give 7β-[2-(2-t-butoxycarbonylamino-4-thiazolyl)-2-(1-t-butoxycarbonyl-1-methylethoxyimino)acetamido]-3-[1-(3,4-dihydroxyphenacyl)-4-pyridinio]thiomethyl-3-cephem-4-carboxylic acid p-methoxybenzyl ester chloride (0.94 g; Yield 60%).

IR (CHCl$_3$): 3400, 1790, 1725, 1690sh cm$^{-1}$.

30) Similarly prepared are the amides listed on Tables 2 and 3 from the corresponding amine and acid.

EXAMPLE 2

Deacylation

1) To a solution of the corresponding amide in dichloromethane under nitrogen atmosphere and ice cooling are added pyridine (2.2 Eq.) and phosphorus pentachloride (2 Eq.), and the mixture is stirred at room temperature for 1.5 hours. The reaction mixture is cooled at −40° C., added methanol or isobutanol (40 parts), and stirred under ice cooling for 4 hours. The separating crystls are collected by filtration to obtain hydrochloride of the corresponding amino compound.

2) The said hydrochloride is suspended in ethyl acetate, neutralized under ice cooling with aqueous sodium hydrogen carbonate, and extracted with ethyl acetate. The extract solution is washed with water, dried, and concentrated under reduced pressure to give amino compound.

3) Amino compound can be produced by deacylating the corresponding amido compound under the condition as given above.

4) To a solution of 7β-phenylacetamido-3-[1-(3,4-dihydroxyphenacyl)-4-pyridiniothio]methyl-3-cephem-4-carboxylic acid p-methoxybenzyl ester iodide (2.52 g; 3.0 mMol.) in dichloromethane (25 ml) at −10° C. are added pyridine (0.53 ml; 2.2 Eq.) and trimethylsilyl chloride 0.84 ml (2.2 Eq.), and the mixture is stirred for 30 minutes. The reaction mixture at −20° C. is mixed with pyridine (0.36 ml; 1.5 Eq.) and phosphorus pentachloride (0.94 g; 1.3 Eq.), stirred for 30 minutes at the same temperature and at 0° C. for 30 minutes. This solution at −40° C. is diluted with methanol (10 ml), stirred at 0° C. for 1 hour, diluted with water, and concentrated under reduced pressure. The residue is washed with cold water and ether to give 7β-amino-3-[1-(3,4-dihydroxyphenacyl)-4-pyridiniothio]methyl-3-cephem-4-carboxylic acid p-methoxybenzyl ester hydrochloride chloride (1.04 g).

Yield: 52%.

IR (CHCl$_3$): 1785, 1720 cm$^{-1}$.

5) Similarly prepared are the amines from the corresponding amide listed on Tables 2 and 3.

EXAMPLE 3

Salt Formation

1) To a solution of the corresponding carboxylic acid in acetone (10 parts) is added a solution of sodium ethylhexanoate in isobutanol (1 to 2 Eq.), and the mixture is diluted with ethyl acetate and ether. The separating crystals are collected by filtration to give the sodium salt.

2) The corresponding carboxylic acid is suspended in water and adjusted to pH 6.5 with sodium carbonate. The solution is desalted and poured into vials, and lyophilized in a conventional manner to give sodium salt formulation.

3) The said sodium salt (1 g) prepared by neutralizing under sterile condition is dissolved in distilled water for injection (4 g) and administered to a patient suffering from sensitive pseudomonal bacteria twice a day intravenously to treat this infection. The free acid or sodium salt is dissolved in 0.01N-aqueous sodium hydrogen carbonate and tested for minimal inhibitory concentration against gram-negative bacteria according to a method of Japan Society of Chemotherapy on an agar plate by two-fold dilution method. The results shows that the activity was superior to that of closely related compounds against *Pseudomonas aeruginosa* SR24.

4) A solution of 7β-[2-(2-amino-4-thiazolyl)-2-(1-carboxy-1-methylethoxyimino)acetamido]-3-[1-(3,4-dihydroxyphenacyl)-4-pyridiniothiomethyl-3-cephem-4-carboxylate 1β-oxide (8.00 g; 10.7 mMol.) and sodium hydrogen carbonate (1.80 g: 2 Eq.) in water (80 ml) is passed through stylene-divinylbenzene copolymer adsorbent (300 ml). The column is washed with water and the objective product is eluted with aqueous 10 to 60% methanol. The eluate is concentrated in vacuum and lyophilized to give monosodium 7β-[2-(2-amino-4-thiazolyl)-2-(1-carboxy-1-methylethoxyimino)acetamido]-3-[1-(3,4-dihydroxyphenacyl)-4-pyridinio]thiomethyl-3-cephem-4-carboxylate 1β-oxide (4.0 g).

5) Similarly prepared are salts from the corresponding carboxylic acids listed on Table 3.

EXAMPLE 4

Esterification

1) Diphenylmethyl ester: To a mixed solution of the corresponding carboxylic acid in dichloromethane (10 parts) and methanol (10 parts) is added diphenyldiazomethane (1.2 Eq.). The mixture is stirred at room temperature for 1 hours. The reaction mixture is washed with hydrochloric acid and water, dried, and, concentrated under reduced pressure. The residue is recrystallized from ethyl acetate to give diphenylmethyl ester.

2) Similarly prepared are diphenylmethyl esters on Table 2 from the corresponding carboxylic acids.

EXAMPLE 5

Deesterification

1) [aluminum chloride] To the corresponding diphenylmethyl ester, t-butyl ester or p-methoxybenzyl ester is added anisole (12 parts) and aluminum chloride (9 Eq.), and the mixture is stirred at −40° to 0° C. for 4 hours. The reaction mixture is mixed with aqueous 5% sodium hydrogen carbonate, filtered to remove solid, diluted with ethyl acetate. The aqueous layer is separated, acidified with hydrochloric acid, washed with ethyl acetate, and poured onto a column of synthetic adsorbent. The objective product is eluted from the column with 80% methanol to give the carboxylic acid.

2) [trifluoroacetic acid] A solution of the corresponding diphenylmethyl ester, t-butyl ester or p-methoxybenzyl ester in dichloromethane (0.3 to 3 parts), trifluoroacetic acid (0.3 to 3 parts) and anisole (0.5 to 5 parts) is stirred at −10° to 40° C. for 10 minutes to 3 hours. The reaction mixture is concentrated under reduced pressure to remove the solvent and reagents. The residue is washed with benzene to give carboxylic acid. When the starting material has t-butoxycarbonylamino, this is deprotected to give the corresponding amine trifluoroacetate.

3) [tin tetrachloride] To a solution of the corresponding diphenylmethyl ester, t-butyl ester, or p-methoxybenzyl ester in anisole (10 volumes) is added tin tetrachloride (15 Eq.) and the mixture is stirred at 0° C. for 24 hours. The reaction mixture is taken into ice cold ethyl acetate and diluted hydrochloric acid. The separating aqueous layer is passed through a column of polymer adsorbent HP-20 (16.5 ml) to remove salt and the product is eluted with methanol. The eluate is lyophilized to give carboxylic acid.

4) [titanium tetrachloride] To a solution of the corresponding diphenylmethyl ester, t-butyl ester or p-methoxybenzyl ester in dichloromethane (5 to 9 parts) and anisole (2 to 8 parts) keeping at −10° to 10° C. is added titanium tetrachloride (3 to 12 Eq.), and the mixture is stirred for 1 to 24 hours. The reaction mixture is treated with aqueous 5% sodium hydrogen carbonate, filtered to remove solid, diluted with ethyl acetate. The formed aqueous layer is acidified with hydrochloric acid, washed with ethyl acetate, and passed through a synthetic adsorbent column. The objective product is eluted with 80% methanol to give carboxylic acid. When the starting material has t-butoxycarbonylamino, N-t-butoxycarbonyl-N-methoxyethoxymethylamino, benzyloxycarbonylamino, or the like protected amino this may be deprotected to give the corresponding amino trifluoroacetate.

5) [formic acid] To a solution of the corresponding diphenylmethyl ester in anisole (2 to 3 parts) is added 90% formic acid (5 to 6 parts), and the mixture is heated at 50° to 60° C. for 1 to 4 hours to give a carboxylic acid.

6) [p-nitrobenzyl ester:catalytic reduction] To a solution of the corresponding p-nitrobenzyl ester in methanol (10 to 35 parts) and tetrahydrofuran (20 parts) are added 10% palladium carbon (0.15 to 0.22 parts) and 2N-hydrochloric acid (1 part). The mixture is shaken under hydrogen for 2 to 5 hours. The reaction mixture is filtered to remove solid, washed with ethyl acetate, neutralized with aqueous sodium hydrogen carbonate, passed through a column of styrene-divinylbenzene copolymer adsorbent to be desalted, and lyophilized to give sodium carboxylate salt.

7) [p-nitrobenzyl ester:acid and zinc] To a solution of the corresponding p-nitrobenzyl ester in dichloromethane (60 parts) are added acetic acid (10 parts) and zinc powder (2 parts), and the mixture is stirred for 2 hours. The reaction mixture is filtered to remove solid, diluted with water, and washed with dichloromethane. The aqueous layer is acidified to pH 2 with hydrochloric acid and purified with a column of styrene-divinylbenzene copolymer to give a carboxylic acid.

8) To a stirred solution of aluminum chloride (1598 g:8 Eq.) in anisole (160 ml) keeping at −40° C. is added a solution of 7β-[2-(2-t-butoxycarbonylamino-4-thiazolyl)-2-(1-t-butoxycarbonyl-1-methylethoxyimino)acetamido]-3-[1-(3,4-dihydroxyphenacyl)-4-pyridinio]thiomethyl-3-cephem-4-carboxylic acid p-methoxybenzyl ester 1β-oxide (16.53 g; 15 mMol.) in dichloromethane (250 ml), and the mixture is stirred at −40° to −30° C. for 1 hours. The reaction mixture is added to a mixture of 1N-hydrochloric acid (150 ml) and cold methanol (150 ml). The aqueous layer is taken, washed with dichloromethane, and concentrated under reduced pressure. The remaining solution is passed through styrene-divinylbenzene copolymer (600 ml). The column is washed with water and aqueous 10% methanolic hydrochloric acid and the product is eluted with aqueous 50% methanol. The eluate is concentrated under reduced pressure and adjusted to pH 3. The separating precipitation is collected by filtration, and washed with water and acetone to give 7β-[2-(2-amino-4-thiazoyl)-2-(1-carboxy-1-methylethoxyimino)acetamido-3-[1-(3,4-dihydroxyphenacyl)-4-pyridinio]thiomethyl-3-cephem-4-carboxylate 1β-oxide (10.15 g).

Yield: 92%.

9) Under a condition similar to above, the carboxylic acids listed on Table 3 can be prepared from the corresponding esters/amides.

EXAMPLE 6

3-Pyridiniothio Introduction

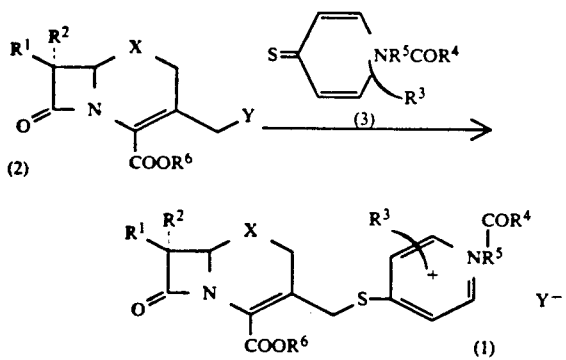

1) A solution of the corresponding bromomethylcephem compound (2) (1 part) and di-protected hydroxyphenacylthiopyridone (3) (1 Eq.) in N, N-dimethylformamide (18 volumes) is stirred at room temperature for 3 hours. The reaction mixture is diluted with ethyl acetate, washed with water, dried, and concentrated under reduced pressure to give pyridiniothio compound (1).

2) To a solution of the corresponding corresponding chloromethylcephem compound (2) (1 part) in N, N-dimethylformamide (13 volumes) keeping at 0° C. is added dihydroxythiopyridone (3) (2.5 Eq.) and stirred at room temperature for 5 hours. The reaction mixture is diluted with ethyl acetate, washed with water, dried, and concentrated under reduced pressure. The residue is washed with ether to give pyridiniothio compound (1).

3) A solution of the corresponding 3-chloromethylcephem compound (2) (1 parts), diprotected hydroxyphenacylthiopyridone (3) (1.2 Eq.) and tetrabutylammonium bromide (catalytic amount) in dichloromethane (10 to 20 parts) is stirred at room temperature for 30 minutes to 3 hours. The reaction mixture is washed with water, dried, and concentrated under reduced pressure to give pyridiniothio compound (1). 4) A solution of the corresponding 3-acetoxymethylcephem compound (2) (1 part) and diprotected hydroxyphenacylthiopyridone (3) (1.5 Eq.) in N,N-dimethylformamide (5 to 20 parts) is stirred at 0° C. to 10° C. for 30 minutes to 3 hours. The reaction mixture is poured into water and extracted with ethyl acetate. The extract solution is washed with water, dried, and concentrated under reduced pressure to give pyridiniothio compound (1).

5) A solution of the corresponding 3-dichloroacetoxymethylcephem compound (2) (1 parts) and diprotected hydroxyphenacylpyridiniothiol (3) (3.5 Eq.) in N,N-dimethylformamide (5 to 20 parts) is stirred at 0° to 10° C, for 30 minutes to 3 hours. The reaction mixture is diluted and extracted with ethyl acetate. The extract solution is washed with water, dried, and concentrated under reduced pressure to give pyridiniothio compound (1).

6) Similarly prepared are the pyridiniothio compounds listed on Tables 2 and 3.

EXAMPLE 7

Pyridinio Formation

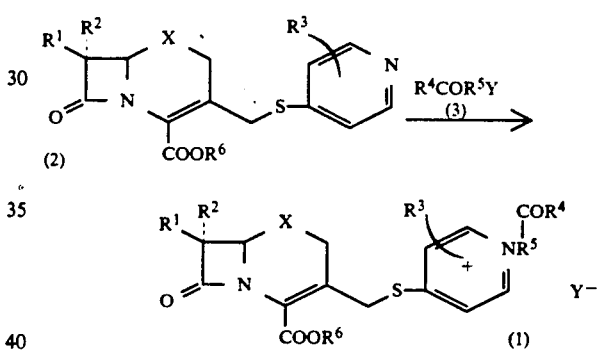

1) To a solution of pyridylthio compound (2) in dichloromethane (2 to 10 parts) is added bisprotected hydroxyphenacyl bromide (3) (1 to 3 Eq.), and kept at 10° to 30° C. for 10 hours to 1 weak. The reaction mixture is diluted with dichloromethane, washed with water, dried, and concentrated in vacuo to give the corresponding pyridinio compound (1).

2) To a solution of pyridylthio compound (2) and sodium iodide (1 to 2 Eq.) in dimethylformamide (2 to 10 parts) is added bisprotected hydroxyphenacyl chloride (3) (1 to 3 Eq.), and the mixture is stirred at room temperature overnight. The reaction mixture is diluted with dichloromethane, washed with water, dried, and concentrated under reduced pressure to give corresponding pyridinio compound (1).

3) To a solution of 7β-[2-(2-t-butoxycarbonylamino-4-thiazolyl)-2-(1-t-butoxycarbonyl-1-methylethoxyimino)acetamido]-3-(4-pyridylthio)methyl-3-cephem-4-carboxylic acid p-methoxybenzyl ester 1β-oxide (13.07 g; 15 mMol.) and α-chloro-3,4-dihydroxyacetophenone (4.20 g: 1.5 Eq.) in acetone (130 ml) is added sodium bromide (2.32 g: 1.5 Eq.) and the mixture is stirred for 24 hours at room temperature. The reaction mixture is concentrated under reduced pressure. The remaining solution is washed with water, diluted with dichloromethane washed with water, dried, and concentrated under reduced pressure. The residue is washed with ether to give 7β-[2-(2-t-butoxycarbonyl-amino-4-thiazolyl)-2-(1-t-butoxycarbonyl-1-methylethoxyimino)acet-amido]-3-[1-(3,4-dihydroxyphenacyl)-4-pyridinio]thiomethyl-3-cephem-4-carboxylic acid p-methoxybenzyl ester 1β-oxide bromide (16.4 g).
Yield: 99%.

4) To a solution of 7β-[2-(2-amino-4-thiazolyl)-2-(1-carboxy-1-methylethoxyimino)acetamido]-3-pyridylthiomethyl-3-cephem-4-carboxylic acid 1β-oxide (1.50 g; 2.54 mMol.) and α-chloro-3,4-dihydroxyacetophenone (0.71 g: 1.5 Eq.) in N,N-dimethylformamide (5 ml) is added sodium iodide (0.57 g: 1.5 Eq.), and the mixture is stirred overnight. The reaction mixture is diluted with water and passed through a column of styrene-divinylbenzene copolymer adsorbent. The product is eluted from the column with water to aqueous 60% methanol to give 7β-[2-(2-amino-4-thiazolyl)-2-(1-carboxy-1-methylethoxyimino)acetamido]-3-[1-(3,4-dihydroxyphenacyl)-4-pyridinio]thiomethyl-3-cephem-4-carboxylate 1β-oxide iodide (605 mg).
Yield: 32%.

5) Similarly prepared are the pyridinio compounds listed on Tables 2 and 3 from the corresponding pyridylthio compounds.

EXAMPLE 8

Sulfoxide Formation

1) [m-chloroperbenzoic acid] To a solution of the corresponding sulfide in a mixture of dichloromethane (10 parts) and methanol (6 parts) is added a solution of 80% m-chloroperbenzoic acid (1.2 Eq.) in a mixture of dichloromethane (17 parts) and methanol (4 parts), and the mixture is stirred for 10 minutes under ice cooling. The separating crystals are collected to give a sulfoxide.

2) [m-chloroperbenzoic acid] To a solution of the corresponding sulfide in chloroform (10 to 20 parts) is added m-chloroperbenzoic acid (1 Eq.) under ice cooling, and the mixture is stirred for 20 to 90 minutes. The reaction mixture is washed with aqueous sodium hydrogen carbonate, dried, and concentrated under reduced pressure to give a sulfoxide.

3) [hydrogen peroxide—polyphosphoric acid] To a solution of the corresponding sulfide in chloroform (10 to 20 parts) is added under ice cooling polyphosphoric acid (0.5 to 1 Eq.) and hydrogen peroxide (1.0 to 2 Eq.), and the mixture is stirred for 20 to 90 minutes. The reaction mixture is washed with aqueous sodium hydrogen carbonate, dried, and, concentrated under reduced pressure to give the sulfoxide.

4) [hydrogen peroxide—tungstic acid] To a solution of the corresponding sulfide in aqueous sodium hydrogen carbonate (10 to 20 parts) is added under ice cooling a catalytic amount of tungstic acid and hydrogen peroxide (1.1 Eq.), and the mixture is stirred for 20 to 90 minutes. The reaction mixture is extracted with chloroform, dried, and concentrated under reduced pressure to give the sulfoxide.

5) [m-chloroperbenzoic acid] To a solution of 7β-[2-(2-t-butoxycarbonylamino-4-thiazolyl)-2-(1-t-butoxycarbonyl-1-methylethoxyimino)acetamido]-3-[1-(3,4-dihydroxyphenacyl)-4-pyridinio]thiomethyl3-cephem-4-carboxylic acid p-methoxybenzyl ester (0.94 g: 0.9 mMol.) in dichloromethane (10 ml) is added 80% m-chloroperbenzoic acid (0.19 g: 1 Eq.) at −70° C., and the mixture is kept at 0° C. for 1 hour. The reaction mixture is concentrated under reduced pressure and resulting mass is washed with ether to give 7β-[2-(2-t-butoxycarbonylamino-4-thiazolyl)-2-(1-t-butoxycarbonyl-1-methylethoxyimino)acetamido]-3-[1(3,4-dihydroxyphenacyl)-4-pyridinio]thiomethyl-3-cephem-4-carboxylic acid p-methoxybenzyl ester 1β-oxide (0.9 g).
Yield: 95%.
IR(CHCl$_3$): 1798, 1721, 1675 cm$^{-1}$.

6) Similarly prepared are the sulfoxides listed on Tables 2 and 3 from the corresponding sulfides.

EXAMPLE 9

Reduction of Sulfoxide

1) [phosphorus tribromide] To a solution of the corresponding sulfoxide in dichloromethane (5 to 50 parts) is added phoshorus tribromide (1 to 3 Eq.) at −40° to −10° C. and the mixture is stirred for 30 minutes to 5 hours at the same temperature. The reaction mixture is diluted with dichloromethane, washed with aqueous sodium hydrogen carbonate and water, dried, and concentrated under reduced pressure to give the sulfide.

2) [phosphorus tribromide] To a solution of the corresponding sulfoxide in dichloromethane (50 parts) and dimethylacetamide (10 parts) cooling at −20° to −25° C. is added a solution of phosphorus tribromide (2.5 Eq.: 30 parts) in dichloromethane, and the mixture is stirred at the same temperature for 1 hour 25 minutes. The reaction mixture is diluted with dichloromethane, washed with aqueous sodium hydrogen carbonate and water, dried, and, concentrated under reduced pressure to give the sulfide.

3) [potassium iodide] To a stirred solution of the corresponding sulfoxide in acetone (11 parts) are added potassium iodide (6 Eq.) and acetyl chloride (7 Eq.) at −25° C., and the mixture is stirred for 35 minutes. The reaction mixture is diluted with ethyl acetate, washed with aqueous sodium hydrogen sulfite, diluted hydrochloric acid, aqueous sodium hydrogen carbonate, and water, dried, and concentrated under reduced pressure. The residue is purified by silica gel chromatography to give the sulfide.

4) [stannous chloride] To a solution of the corresponding sulfoxide in N,N-dimethylformamide (12 parts) under nitrogen gas is added under ice cooling stannous chloride (2.5 Eq.) and acetyl chloride (13 Eq.) and the mixture is stirred for 21 hours. The reaction mixture is poured onto ice water, extracted with ethyl acetate, washed with water and aqueous sodium hydrogen carbonate, dried, and concentrated under reduced pressure. The residue is crystallized from a mixture of dichloromethane, benzene, and ether to give the sulfide.

5) Similarly prepared are the sulfides listed on Tables 2 and 3 from the corresponding sulfoxides.

EXAMPLE 10

Protection of Hydroxy

1) [O-benzyloxycarbonyl] To a solution of the corresponding hydroxy compound in dichloromethane (5 to 20 parts) is added benzyl chloroformate (3 Eq.), and the mixture is stirred at −20° to 10° C. for 1 to 5 hours. The reaction mixture is diluted with dichloromethane washed with aqueous sodium hydrogen carbonate and water, dried, and, concentrated under reduced pressure. The residue is recrystallized to give O-benzyloxycarbonyl compound.

2) [silyl] To a solution of the corresponding hydroxy compound in N,N-dimethylformamide (5 parts) are added t-butyldimethylsilyl chloride (1 to 2 Eq.) and triethylamine (2 to 3 Eq.), and the mixture is stirred at 0°

C. for 1 to 2 hours. The reaction mixture is diluted with ethyl acetate, washed with diluted hydrochloric acid, aqueous sodium hydrogen carbonate, and water, dried, and concentrated under reduced pressure. The residue is purified by silica gel chromatography to give O-t-butyldimethylsilyl compound.

3) [p-methoxybenzyl] To a solution of the corresponding hydroxy compound in acetone (10 to 20 parts) are added p-methoxybenzyl bromide (1 to 3 Eq.) and potassium carbonate (1 to 3 Eq.), and the mixture is stirred at −20° to 10° C. for 1 to 5 hours. The reaction mixture is diluted with dichloromethane, washed with aqueous sodium hydrogen carbonate and water, dried and concentrated under reduced pressure. The residue is purified by silica gel chromatography and recrystallization to give p-methoxybenzyl ether.

4) Similarly protected are the hydroxy compounds on Tables 2 and 3.

EXAMPLE 11

Deprotection of Protected Hydroxy

1) [aluminum chloride] To a solution of the corresponding p-methoxybenzyl ether in anisole (12 parts) is added aluminum chloride (9 Eq.), and the mixture is stirred at 0° C. for 4 hours. The reaction mixture is washed with water and diluted hydrochloric acid, dried, and concentrated under reduced pressure to give the phenol.

2) [stannic tetrachloride] To a solution of the corresponding p-methoxybenzyl ether in anisole (10 volumes) is added stannic tetrachloride (15 Eq.), and the mixture is stirred at 0° C. for 24 hours. The reaction mixture is washed with water and hydrochloric acid, dried, and concentrated under reduced pressure to give phenol.

3) [titanium chloride] To a solution of the corresponding p-methoxybenzyl ether in a mixture of dichloromethane (5 to 9 parts) and anisole (2 to 8 parts) is added titanium tetrachloride (3 to 12 Eq.) at −10° to 10° C., and the mixture is stirred for 1 to 24 hours. The reaction mixture is washed with water and hydrochloric acid, dried, and concentrated under reduced pressure to give the phenol.

4) [sodium hydrogen carbonate] To a solution of the corresponding phenol acetate in water (8 ml) containing sodium hydrogen carbonate (9 Eq.), and the mixture is stirred at room temperature for 1 to 6 hours. The reaction mixture is neutralized with hydrochloric acid and extracted with dichloromethane. The extract solution is washed with water, dried, and concentrated under reduced pressure to give the phenol.

5) Similarly prepared are hydroxy compounds on Tables 2 and 3.

EXAMPLE 12

Deprotection of Protected Amino

1) [aluminum chloride] To a solution of the corresponding carbobenzoxyamine are added anisole (12 parts) and aluminum chlride (9 Eq.), and the mixture is stirred at 0° C. for 4 hours. The reaction mixture is washed with water and aqueous sodium carbonate, dried, and concentrated under reduced pressure to give the amine.

2) [stannic tetrachloride] To a solution of the corresponding t-butoxycarbonylamine in anisole (10 volumes) is added stannic tetrachloride (15 Eq.) and the mixture is stirred at 0° C. for 24 hours. The reaction mixture is washed with water and aqueous sodium carbonate, dried and concentrated under reduced pressure to give the amine.

3) [titanium tetrachloride] To a solution of the corresponding carbobenzoxyamine in a mixture of dichloromethane (5 to 9 parts) and anisole (2 to 8 parts) is added titanium tetrachloride (3 to 12 Eq.) at −10° to 10° C., and the mixture is stirred for 1 to 9 hours. The reaction mixture is washed with water and aqueous sodium carbonate, dried, and concentrated under reduced pressure to give the amine.

4) [thiourea] To a solution of the corresponding chloroacetamide in dichloromethane (5 to 9 parts) and methanol (10 parts) is added thiourea, and the mixture is stirred at 0° to 30° C. for 1 to 24 hours. The reaction mixture is washed with water and aqueous sodium carbonate dried, and concentrated under reduced pressure to give the amine.

5) Similarly prepared are the amino compounds listed on Table 3.

EXAMPLE 13

Ampoule Formulation

Sodium salt of compound (I) (1 g) where $R^1$ is 2-(2-amino-4-thiazolyl)-2-(1-carboxy-1-methylethoxyimino)acetamido, $R^2$ is hydrogen, $R^3$ is hydrogen, $R^4$ is 3,4-dihydroxyphenyl, $R^5$ is methylene, $R^6$ combined with Y is negative charge, and X is sulur; is dissolved in distilled water for injection (3 ml) and poured into 5 ml light proof amouple filled with nitrogen. This ampoule formulation is given 1 to 4 times per day intramuscularly to a patient suffering from sensitive pseudomonal infection to cure or improve symptom of the disease.

EXAMPLE 14

Vial Formulation

Sodium salt of compound (I) (1 g) where $R^1$ is 2-(2-amino-4-thiazolyl)-2-(1-carboxy-1-methylethoxyimino)acetamido, $R^2$ is hydrogen, $R^3$ is hydrogen, $R^4$ is 3,4-dihydroxyphenyl, $R^5$ is methylene, $R^6$ combined with Y− is negative charge, and X is sulfinyl, is dissolved in distilled water for inection and poured into a vial. This is freezed at −30° C. by conventional method and lyophilized at 0.01 millibar keeping the inner temperature at −20° C. This vial formulation is dissolved in distilled water for injection prior to use and administered 1 to 4 times per day intravenously to a patient suffering from sensitive Serratia infection to treat the disease.

EXAMPLE 15

Vial Formulation

Sodium salt of compound (I) (1 g) where $R^1$ is 2-(2-amino-4-thiazolyl)-2-(1-carboxy-1-methylethoxyimino)acetamido, $R^2$ is hydrogen, $R^3$ is hydrogen, $R^4$ is 3,4-dihydroxyphenyl, $R^5$ is ethylidene, $R^6$ combined with Y is negative charge, and X is sulfur is dissolved in distilled water for injection (5 ml) and filled in a vial. This is freezed conventionally using dry ice and lyophilized at 0.03 millibar keeping the inner temperature at −20° C. This vial formulation is dissolved in a nutrient carrier and dripped 1 to 4 times per day to a patient suffering from sensitive *Enterobacter cloacae* infection to treat the disease.

EXPERIMENT 1

Superior Antipseudomonal Activity

The minimal inhibitory concentration of Compound (I) where $R^1$ is 2-(2-amino-4-thiazolyl)-2-(1-carboxy-1-methylethoxyimino)acetamido, $R^2$ is hydrogen, $R^3$ is hydrogen, $R^4$ is 3,4-dihydroxyphenyl, $R^5$ is methylene, $R^6$ combined with $Y-$ is negative charge, and X is sulfur against Pseudomonas aeruginosa SR 24 is 0.2 µg/ml. By altering the groups with the following ones to vary the activities as listed below.

| 7β-side chain $R^1$ | |
|---|---|
| phenylacetyl | >100 |
| difluoromethylthioacetyl | >100 |
| 2-AT-2-methoxyiminoacetamido | 0.40 |
| 2-AT-3-carboxy-3-methylpentenamide | 0.10 |
| (AT = 2-amino-4-thiazolyl) | |
| Substituent for pyridyl $R^3$ | |
| 2,3-trimethylene | 0.05 |
| Cathecolyl group $R^4$ | |
| 2,3-dihydroxyphenyl | 0.39 |
| 6-methyl-3,4-dihydroxyphenyl | 0.05 |
| 5-chloro-3,4-dihydroxyphenyl | 0.025 |
| 6-chloro-3,4-dihydroxyphenyl | 0.025 |
| 3,4-diacetoxyphenyl | 0.025 |
| Alkylene $R^5$ | |
| ethylidene | 0.025 |
| Position 1 of cephem ring X | |
| sulfinyl | 0.10 |
| oxygen atom | 0.20 |

EXPERIMENT 2

Activity and Safety Tests

Compound (I) where $R^1$ is 2-(2-amino-4-thiazolyl)-2-(1-carboxy-1-methylethoxyimino)acetamido, $R^2$ is hydrogen, $R^3$ is hydrogen, $R^4$ is 3,4-dihydroxyphenyl, $R^5$ is methylene, $R^6$ combined with $Y-$ is negative charge, and X is sulfinyl shows 50% effective dose preventing lethal Pseudomonas aeruginosa SR 24 mouse infection is 1.35 mg/kg. The compound is highly safe in the case of intravenous injection to various animals. Namely, mice showed no death nor toxic effect as Antabuse-like activity at a dose up to 1 g/kg. Rabbits did not show renal toxicity at a dose up to 1 g/kg.

PREPARATION OF STARING MATERIALS

A: 7-Side Chain Acids

Preparation A [Protection of Amino]

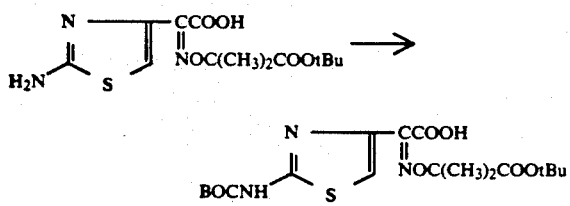

To a mixture of dichloromethane (1.1 liters), 2-(2-aminothiazol-4-yl)-2-(1-t-butoxycarbonyl-1-methylethoxyimino)acetic acid (142 g; 431 mMol.), and triethylamine (89.7 ml; 1.5 Eq.) are added di-t-butyl pyrocarbonate (122 g; 1.3 Eq.) and 4-DMAP (10.5 g; 0.2 Eq.), and the mixture is kept at room temperature for 23 hours. The reaction mixture is concentrated under reduced pressure and diluted with ether. The organic layer is extracted with water and aqueous 5% sodium hydrogen carbonate. The extract is washed with ether, acidified to pH 2 with concentrated hydrochloric acid, and extracted with dichloromethane. The extract is washed with water, dried, and concentrated under reduced pressure. The residue is solidified with isopropanol to give 2-(2-t-butoxycarbonylamino-4-thiazolyl)-2-(1-t-butoxycarbonyl-1-methylethoxyimino)acetic acid (76.93 g).

Yield: 42%.

PREPARATION OF STARING MATERIALS

B: 3-Substituents

Preparation B-1 (CH₂CO-2,3-substituent)

To a solution of 2,3-dihydroxybenzaldehyde (1) (6.91 g; 50 mMol.) in N, N-dimethylformamide (70 ml) cooling at 0° C. are added potassium carbonate power (17.97 g; 2.6 Eq.) and p-methoxybenzyl bromide (26.14 g; 2.6 Eq.), and the mixture is stirred at room temperature for 4 hours.

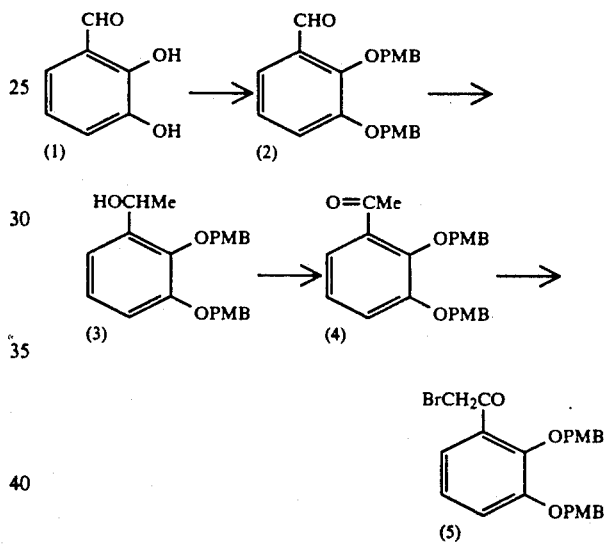

The reaction mixture is dilued with ethyl acetate and water. The organic layer is washed with water, dried, and concentrated under reduced pressure. The residue is crystallized from a mixture of ether and hexane to give 2,3-di(p-methoxybenzyloxy)benzaldehyde (2) (16.43 g).

Yield: 87%.

mp. 92°-93° C.

(2) NMR δ (CDCl₃) ppm: 3.79(s, 3H), 3.84(s, 3H), 5.11(s, 4H), 6.80~7.43(m, 11H), 10.22 (s, 1H).

To a solution of 2,3-di(p-methoxybenzyloxy)benzaldehyde (2) (9.46 g; 25 mMol.) in tetrahydrofuran (50 ml) keeping at −30° C. is added a solution of methyl magnesium bromide in ether (10.8 ml; 1.3 Eq.). After 30 minutes, the reaction mixture is diluted with saturated aqueous ammonium chloride and ethyl acetate, washed with water, dried, and concentrated under reduced pressure. The residue, 2,3-di(p-methoxybenzyloxy)-1-hydroxyethylbenzene (3), is dissolved in acetone (50 ml) and mixed with Jone's reagent (10 ml). After 1 hour, the excess oxidating reagent is decomposed with methanol. The reaction mixture is diluted with ethyl acetate, washed with water, dried, and concentrated under reduced pressure. The residue is purified by silica gel chromatography (toluene: ethyl acetate=9:1), and eluate is crystallized from n-hexane to give 2,3-di(p-methoxybenzyloxy)acetophenone (4) (8.25 g).

Yield: 84%.

mp. 87°-88° C.

(4) NMR δ (CDCl₃) ppm: 2.54(s, 3H), 3.80(s, 3H), 3.84(s, 3H), 4.99(s, 2H), 5.06(s, 2H), 6.75~7.43(m, 11H).

To a solution of 2,3-di(p-methoxybenzyloxy)acetophenone (4) (3.92 g: 10 mMol.) in tetrahydrofuran (20 ml) cooling at −78° C. is added a solution of lithium hexamethyldisilazane in tetrahydrofuran (10 ml: 1 Eq.), and the mixture is stirred for 10 mintues. To this reaction mixture is added a solution of bromine in carbon tetrachlor-ide (10 ml: 1 Eq.). After 10 minutes, the reaction mixture is washed with aqueous sodium bisulfite and water, dried, and concentrated under reduced pressure. The residue is purified by silica gel chromatography (n-hexane: ethyl acetate: dichloromethane=10:1:1) to give 2,3-di(p-methoxybenzyloxy)-ω-bromoacetophenone (5) (1.14 g).

Yield: 24%.

(5) NMR δ (CDCl₃) ppm: 3.81(s, 3H), 3.84(s, 3H), 4.47(s, 2H), 5.06(s, 2H), 5.10(s, 2H), 6.81~7.42(m, 1H).

Preparation B-2 (CH₂CO-3,4-PMB-Substituent)

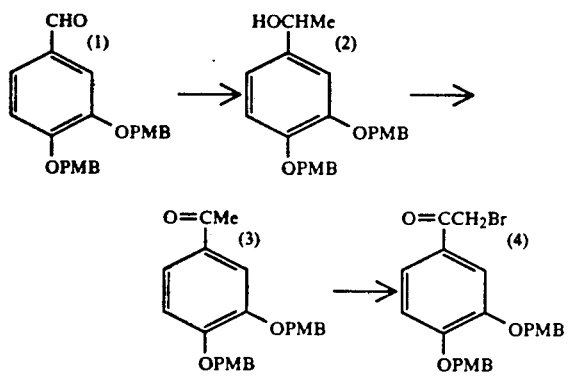

To a solution of 3,4-di(p-methoxybenzyloxy)benzaldehyde (1) (11.35 g: 30 mMol.) in tetrahydrofuran (114 ml) keeping at −30° C. is added a solution of methylmagnesium bromide in ether (12 ml: 1.2 Eq.). After 30 minutes, the reaction mixture is diluted with saturated aqueous ammonium chloride and extracted with ethyl acetate. The extract is washed with water, dried, and concentrated under reduced pressure. The residual 3,4-di(p-methoxybenzyloxy)benzyloxyphenylethanol (2) is dissolved in acetone (50 ml) treated at 0° C. excess Jones reagent, and let stand for 1 hour. After decomposing excess reagent with methanol, the reaction mixture is diluted with ethyl acetate, washed wtih water, dried, and concentrated under reduced pressure. The resulting crystals are collected by filtration and washed with ether to give 3,4-di(p-methoxybenzyloxy)acetophenone (3) (7.94 g).

Yield: 67%.

mp. 88°-89° C.

(3) NMR δ (CDCl₃) ppm: 2.48(s, 3H), 3.77(s, 6H), 5.07(s, 2H), 5.11(s, 2H), 6.81~7.58(m, 1H).

To a solution of 3,4-di(p-methoxybenzyloxy)acetophenone (3) (1.77 g: 3 mMol.) in tetrahydrofuran (4 ml) cooling at −40° C. is added a solution of lithium hexamethylsilazane in tetrahydrofuran (4 ml: 1.3 Eq.), and the mixture is stirred for 10 minutes. To the mixture at −78° C. is added a solution of bromine in carbon tetrachloride (3.3 ml: 1.1 Eq.). The reaction mixture is diluted with ethyl acetate, washed with water, dried and concentrated under reduced pressure. The residue is purified by silica gel chromatography to give 3,4-di(p-methoxybenzyloxy)-ω-bromacetophenone (4) (0.744 g).

Yield: 54%.

(4) NMR δ (CDCl₃) ppm: 3.76(s, 6H), 4.28(s, 2H), 5.06(s, 2H), 5.09(s, 2H), 6.8~7.6(m, 11H).

Preparation B-3 (CH₂CO-3,4-OAc-Substituent)

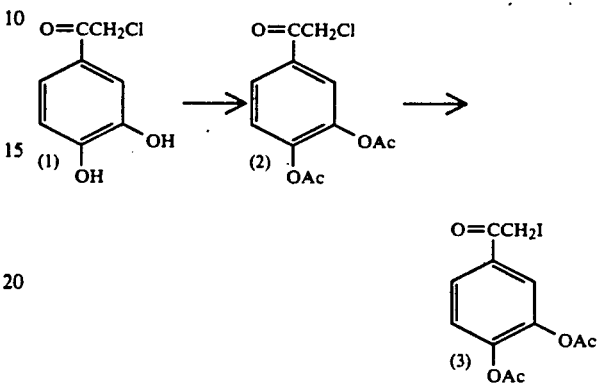

To a solution of 3,4-dihydroxy-ω-chloroacetophenone (1) (1.65 g: 8.84 mMol.) in dichloromethane (17 ml) keeping at 0° C. are added pyridine (1.64 ml: 2.3 Eq.) and acetyl chloride (1.45 ml: 2.3 Eq.), and the mixture is stirred at 0° C. for 30 minutes. The reaction mixture is diluted with ethyl acetate, washed with water, dried, and concentrated under reduced pressure to give 3,4-diacetoxy-ω-chloroacetophenone (2) (2.03 g).

Yield: 85%.

mp. 103°-105° C.

(2) NMR δ (CDCl₃) ppm: 2.327(s, 3H), 2.331(s, 3H), 4.66(s, 2H), 7.32(d, J=8.3 Hz, 1H), 7.82(d, J=2.1 Hz, 1H), 7.87(dd, J=2.1 Hz, J=8.3 Hz, 1H)

To a solution of 3,4-diacetoxy-ω-chloroacetophenone (2) (1.08 g: 4 mMol.) in acetone (11 ml) keeping at 0° C. is added sodium iodide (1.2 g: 2 Eq.), and the mixture is stirred at room temperature for 1 hour. The reaction mixture is diluted with ethyl acetate, washed with water, dried, and concentrated under reduced pressure to give 3,4-diacetoxy-ω-iodacetophenone (3) (1.38 g).

Yield: 95%.

mp. 106°-109° C.

(3) NMR δ (CDCl₃) ppm: 2.33(s, 6H), 4.32(s, 2H), 7.34(d, J=8.5 Hz, 1H), 7.84(d, J=2 Hz, 1H), 7.93(dd, J=2 Hz, J=8.5 Hz, 1H).

Preparation B-4 (Propiophenone Substituent)

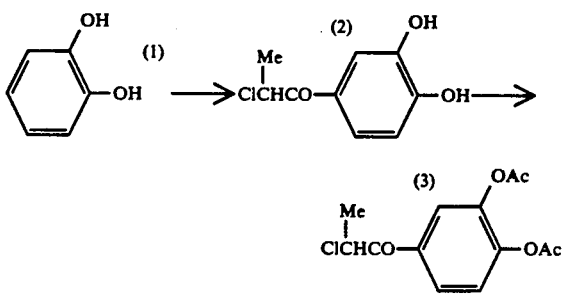

To a solution of cathecol (1) (2.75 g; 25 mMol). in carbon disulfide (20 ml) is added aluminum chloride (6.6 g; 2 Eq.) To this solution stirring at room temperature is added dropwise 2-chloropropionyl chloride (4.0 g; 1.26 Eq.). After 5 hours, the reaction mixture is diluted with ice water and concentrated under reduced pressure. The residual solution is passed through synthetic adsorbent HP-20, and the product is eluted with methanol to give α-chloro-3,4-dihydroxypropiophenone (2) (3.2 g).

Yield: 73.7%.

(2) NMR δ (CD₃SOCD₃) ppm: 1.55(t, J=6 Hz, 3H), 5.59(t, J=6.7 Hz, 1H), 6.2~7.5(m, 3H).

To an ice cold solution of α-chloro-3,4-dihydroxypropiophenone (2) (1.0 g; 4.98 mMol.) in pyridine (3 ml) is added acetic anhydride (1.2 ml) After 1.5 hours at room temperature, the reaction mixture is concentrated under reduced pressure. The residue is dissolved in chloroform, washed with water, dried, and concentrated under reduced pressure to give α-chloro-2,3-diacetoxypropiopheonen (3) (1.3 g).

Yield: 91.5%.

(3) NMR δ (CDCl₃) ppm: 1.74(d, J=6.6 Hz, 3H), 2.33(s, 6H), 5.17(dd, J=6.6 Hz, J=13 Hz, 1H), 7.35(d, J=8.4 Hz, 1H), 7.88(d, J=2 Hz, 1H), 7.95(dd, J=2 Hz, J=8.4 Hz, 1H).

Preparation B-5 (Cyclopentenopyridyl Substituent)

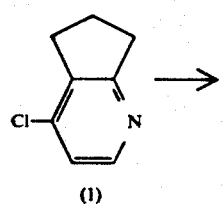

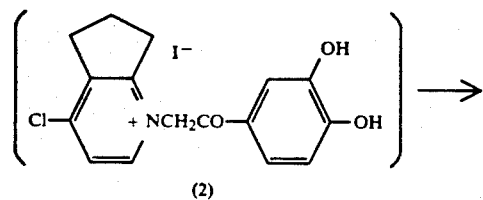

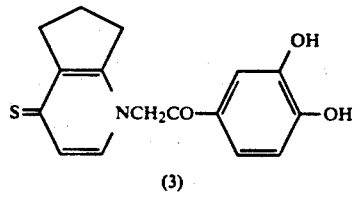

To a solution of 4-chloro-2,3-cyclopentenopyridine (768 mg; 5 mMol.) in acetonitrile (10 ml) are added α-chloro-3,4-dihydroxyacetophenone (933 mg; 1 Eq.) and sodium iodide (900 mg; 1.2 Eq.), and the mixture is stirred at room temperature for 6 hours. The reaction mixture is concentrated under reduced pressure. To a solution of the residual 1-(3,4-dihydroxybenzoyl)methyl-2,3-cyclopentano-4-chloropyridinum iodide (2) in a mixture of chloroform (30 ml) and methanol (30 ml) is added sodium hydrogen sulfite (1.2 g; 4.3 Eq.), and the mixture is stirred at room temperature for 30 minutes. The reaction mixture is washed with water, dried, and concentrated under reduced pressure. The residue is purified by silica gel chromatography (using chloroform:methanol) to give 1-(3,4-dihydroxybenzoylmethyl)-2,3-cyclopentanopyrido-4-thione (3) (1.30 g).

Yield: 86%.

(3) NMR δ (CD₃SOCD₃) ppm: 1.85~2.05(m, 2H), 2.67~2.85(m, 4H), 5.76(s, 1H), 6.89(d, J=8 Hz, 1H), 7.08(d, J=6.9 Hz, 1H), 7.38~7.55(m, 3H).

PREPARATION OF STARING MATERIALS

C: Cephalosporin Part

Preparation C-1

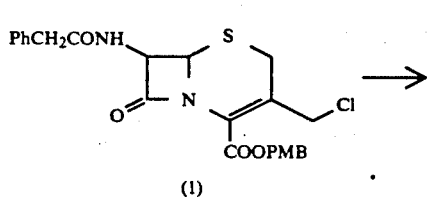

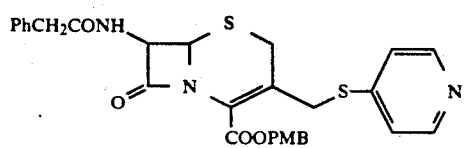

To a stirred and ice cold solution of 7β-phenylacetamido-3-chloromethyl-3-cephem-4-carboxylic acid p-methoxybenzyl ester (1) (4.87 g; 10 mMol.) and 4-mercaptopyridine (1.45 g; 1.3 Eq.) in N,N-dimethylformamide (15 ml) is added sodium hydrogen carbonate (1.09 g; 1.3 Eq.), and the mixture is stirred at room temperature for 1 hour. The reaction mixture is diluted with ice water and separating solidis collected by filtration, dissolved in ethyl acetate, washed with water, dried, and concentrated under reduced pressure. The residue is washed with ether to give p-methoxybenzyl 7β-phenylacetamido-3-(4-pyridyl)thiomethyl-3-cephem-4-carboxylate (2) (5.25 g).

mp. 142°-144° C.

Yield: 93.4%.

(2) NMR δ (CDCl₃) ppm: 3.39, 3.56(ABq, J=18 Hz, 2H), 3.62, 3.64(ABq, J=17 Hz, 2H), 3.79 (s, 3H), 3.99, 4.19(ABq, J=13.3 Hz, 2H), 4.89 (d, J=5 Hz, 1H), 5.19(s, 2H), 5.79(dd, J=5 Hz, J=9 Hz, 1H), 6.11(d, J=9 Hz, 1H), 6.86(d, J=9 Hz, 2H), 7.07(d, J=6 Hz, 2H), 7.20~7.43(m, 7H), 8.35(d, J=6 Hz, 2H).

IR ν (CHCl₃) cm⁻¹: 1786, 1720, 1683.

Preparation C-2

To a solution of 7β-difluoromethylthioacetamido-7α-methoxy-3-chloromethyl-1-dethia-1-oxa-3-cephem-4-carboxylic acid diphenylmethyl ester (1) (2.21 g; 4 mMol.) and 4-mercaptopyridine (0.56 g; 1.25 Eq.)

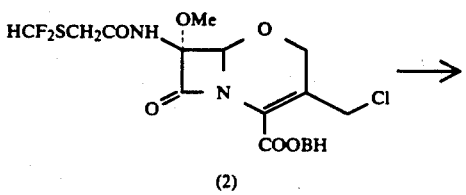

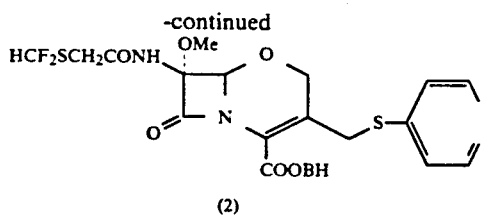

(2)

in N,N-dimethylformamide (11 ml) is added sodium hydrogen carbonate (0.42 g; 1.25 Eq.), and the mixture is stirred at room temperature for 30 minutes. The reaction mixture is diluted with water and the separating precipitate is collected by filtration, washed with water, and dried to give 7β-difluoromethylthioacetamido-7α-methoxy-3-(4-pyridyl)thiomethyl-1-dethia-1-oxa-3-cephem-4-carboxylic acid diphenylmethyl ester (2) (2.40 g).

Yield: 96%.

(2) NMR δ (CDCl₃) ppm: 3.57(s, 5H), 4.08, 4.22(ABq, J=13.6 Hz, 2H), 4.50(s, 2H), 5.07(s, 1H), 6.92(t, J=56 Hz, 1H), 6.94(s, 1H), 7.04(dd, J=1.6 Hz, J=4.6 Hz, 2H), 7.27~7.55(m, 11H), 8.32(dd, J=1.6 Hz, J=4.6 Hz, 2H).

Preparation C-3

1) To a suspension of 7β-amino-3-chloromethyl-3-cephem-4-carboxylic acid p-methoxybenzyl ester (1) p-toluenesulfonate (4.33 g; 8 mMol.) in dichloromethane (40 ml) is added at 0° C. N-methylmorpholine (0.88 g; 1 Eq.), pyridine (0.8 ml; 1.2 Eq.) and 2-(2-t-butoxycarbonylamino-4-thiazolyl)-2-methoxyiminoacetyl chloride (1.2 Eq.). After keeping at 0° C. for 30 minutes, the reaction mixture is diluted with water and ethyl acetate and ethyl acetate layer is taken. This is washed with Yield: 94%.

(2) NMR δ (CDCl₃) ppm: 1.54(s, 9H), 3.51, 3.68(ABq, J=18 Hz, 2H), 3.82(s, 3H), 4.08(s, 3H), 4.43, 4.58(ABq, J=12 Hz, 2H), 4.51(d, J=5 Hz, 1H), 5.20, 5.26(ABq, J=12 Hz, 2H), 6.02 (q, J=5 Hz, J=9 Hz, 1H), 6.91(d, J=9 Hz, 2H), 7.21(s, 1H), 7.35(d, J=9 Hz, 2H), 7.41(d, J=9 Hz, 1H), 8.50(brs, 1H).

IR ν (CHCl₃) cm⁻¹: 3490, 1780, 1716, 1680.

2) To a solution of 4-mercaptopyridine (222 mg; 2 Eq.) in N,N-dimethylformamide (10 ml) keeping at 0° C. is added a solution of sodium methoxide in methanol (1.5 Eq.). To this mixture is added 7β-[2-(2-t-butoxycarbonylamino-4-thiazolyl)-2-methoxyiminoacetamido]-3-chloromethyl-3-cephem-4-carboxylic acid p-methoxybenzyl ester (2) (652 mg; 1 mMol.), and the mixture is stirred for 10 minutes. The reaction mixture is diluted with ethyl acetate, washed with water, dried, and concentrated under reduced pressure. The residue is purified by silica gel chromatography (toluene:ethyl acetate) to give 7β-[2-(2-t-butoxycarbonylamino-4-thiazolyl)-2-methoxyiminoacetamido]-3-(4-pyridyl)thiomethyl-3-cephem-4-carboxylic acid p-methoxybenzyl ester (3) (708 mg).

Yield: 97%.

(3) NMR δ (CDCl₃) ppm: 1.54(s, 9H), 3.49, 3.62(ABq, J=18 Hz, 2H), 3.81(s, 1H), 4.05(s, 3H), 4.04, 4.26(ABq, J=14 Hz, 2H), 5.02(d, J=5 Hz, 1H), 5.18, 5.25(ABq, J=12 Hz, 2H), 5.99 (dd, J=5 Hz, J=9 Hz, 1H), 6.89(d, J=8.8 Hz, 2H), 7.08(d, J=6.1 Hz, 2H), 7.19(s, 1H), 7.35(d, J=8.8 Hz, 2H), 7.68(d, J=9 Hz, 1H), 8.35(d, J=6.1 Hz, 2H).

IR ν (CHCl₃) cm⁻¹: 3420, 1785, 1726, 1688.

3) To a solution of 7β-[2-(2-t-butoxycarbonylamino-4-thiazolyl)-2-methoxyiminoacetamido]-3-(4-pyridyl)-thiomethyl-3-cephem-4-carboxylic acid p-methoxybenzyl ester (3) (800 mg; 1.1 mMol.) in dichloromethane (5

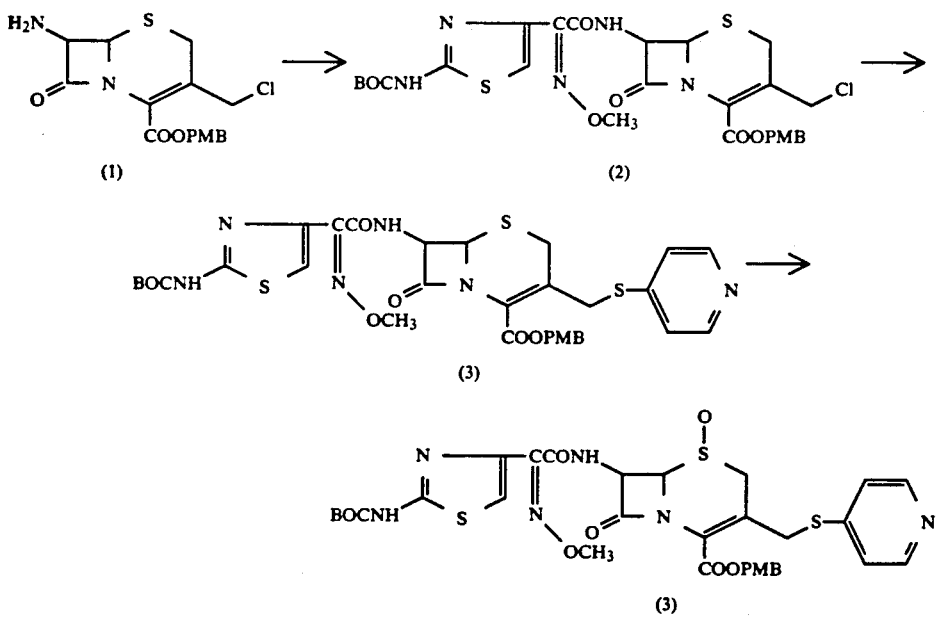

water, dried and concentrated under reduced pressure. The residue is purified by silica gel chromatography (using toluene:ethyl acetate) to give 7β-[2-(2-t-butoxycarbonylamino-4-thiazolyl)-2-methoxyiminoacetamido]-3-chloromethyl-3-cephem-4-carboxylic acid p-methoxybenzyl ester (2) (4.89 g).

ml) keeping at −78° C. is added m-chloroperbenzoic acid (261 mg; 1.1 Eq.), and the mixture is warmed slowly to 0° C. After 30 minutes, the reaction mixture is diluted with ethyl acetate, washed with aqueous sodium sulfite, aqueous sodium hydrogen carbonate and water, dried and concentrated under reduced pressure. The residue is purified by silica gel chromatography (toluene:ethyl acetate) to give 7β-[2-(2-t-butoxycarbonylamino-4-thiazolyl)-2-methoxyiminoacetamido]-3-(4-pyridyl)thiomethyl-3-cephem-4-carboxylic acid p-methoxybenzyl ester 1β-oxide (4) (470 mg).

Yield: 58%.

(4) NMR δ (CDCl₃) ppm: 1.52(s, 9H), 3.37, 3.85(ABq, J=18.5 Hz, 2H), 3.78(s, 3H), 3.62, 4.26(ABq, J=13.2 Hz, 2H), 3.99(s, 3H), 4.55 (d, J=4.8 Hz, 1H), 5.18, 5.28(ABq, J=11.6 Hz, 2H), 6.13(dd, J=4.6 Hz, J=9.6 Hz, 1H), 6.88(d, J=8.8 Hz, 2H), 7.04(dd, J=1.6 Hz, J=4.6 Hz, 2H), 7.23(s, 1H), 7.34(d, J=8.8 Hz, 2H), 7.97(d, J=9.6 Hz, 1H), 8.35(dd, J=1.6 Hz, J=4.6 Hz, 2H).

IR ν (CHCl₃) cm⁻¹: 3400, 1805, 1720, 1680.

Preparation C-4

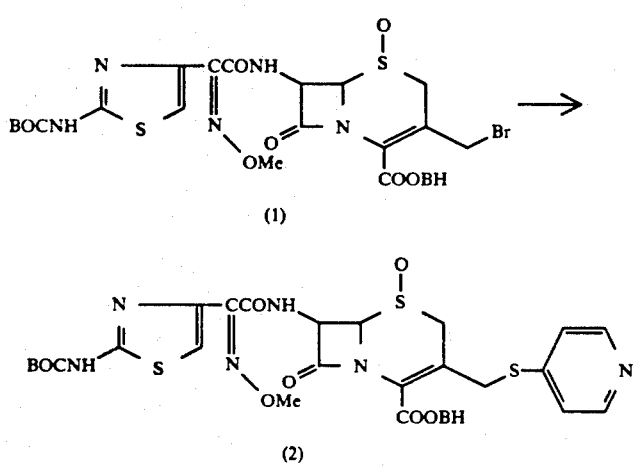

To a solution of 4-mercaptopyridine sodium salt prepared from 4-mercaptopyridine (135 mg; 1.3 Eq.) and sodium methoxide in N,N-dimethylformamide (5 ml) is added to a solution of 7β-[2-(2-t-butoxycarbonylamino-4-thiazolyl)-2-methoxyiminoacetamido]-3-bromomethyl-3-cephem-4-carboxylic acid diphenylmethyl ester 1β-oxide (1) (710 mg; 0.94 mMol.) in N,N-dimethylformamide (5 ml), and the mixture is stirred at −30° C. for 30 minutes. The reaction mixture is diluted with ethyl acetate, washed with water, dried, and concentrated in vacuum. The residue is purified by silica gel chromatography (ethyl acetate) to give 7β-[2-(2-t-butoxycarbonylamino-4-thiazolyl)-2-methoxyiminoacetamido]-3-(4-pyridyl)thiomethyl-3-cephem-4-carboxylic acid diphenylmethyl ester 1β-oxide (2) (640 mg).

Yield: 86%.

(2) NMR δ (CDCl₃) ppm: 1.54(s, 9H), 3.35, 3.86(ABq, J=18 Hz, 2H), 4.55 (d, J=5 Hz, 1H), 3.80, 4.59(ABq, J=12 Hz, 2H), 6.20(dd, J=5 Hz, J=10 Hz, 1H), 6.96(d, J=7 Hz, 2H), 7.01(s, 1H), 7.22∼7.50(m, 11H), 7.73(d, J=10 Hz, 1H), 8.29 (d, J=7 Hz, 2H).

IR ν (CHCl₃) cm⁻¹: 1802, 1722, 1680.

Preparation C-5

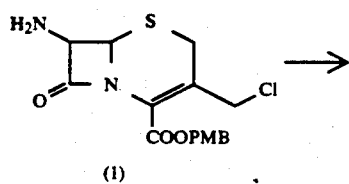

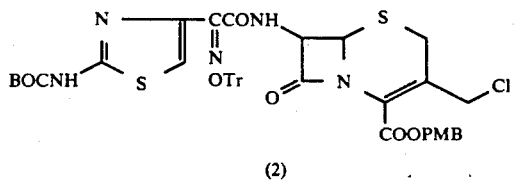

To a solution of N,N-dimethylformamide (0.321 ml; 1 Eq.) in dichloromethane (20 ml) keeping at −10° C. is added dropwise oxalyl chloride (0.354 ml; 1.64 Eq.), and the mixture is stirred at −10° to −5° C. for 15 minutes. To this mixture are added a solution of 2-(2-t-butoxycarbonylamino-4-thiazolyl)-2-triphenylmethoxyiminoacetic acid (2.0 g; 09 Eq.) in dichloromethane (10 ml) and N-methylmorpholine (0.502 ml; 1.1 Eq.), and the mixture is stirred at −10° to −5° C. for 30 minutes. To this solution is added a solution of 7β-amino-3-chloromethyl-3-cephem-4-carboxylic acid p-toluenesulfonate (2.4 g; 4.16 mMol.). To this mixture is added N-methylmorpholine (0.502 ml; 1 Eq.), and the mixture is stirred at −10° to −5° C. for 45 minutes. The reaction mixture is diluted with ice water and extracted with dichloromethane. The extract is washed with hydrochloric acid, aqueous sodium hydrogen carbonate, and water, dried, and concentrated in vacuum. The residue is purified by silica gel chromatography (toluene:ethyl acetate) to give 7β-[2-(2-t-butoxycarbonylamino-4-thiazolyl)-2-trityloxyimino-acetamido]-3-chloromethyl-3-cephem-4-carboxylic acid p-methoxybenzyl ester (2) (2.38 g).

Yield: 71.7%.

(2) NMR δ (CDCl₃) ppm: 1.50(s, 9H), 3.35, 3.58(ABq, J=18 Hz, 2H), 4.40, 4.54(ABq, J=12 Hz, 2H), 5.02(d, J=5 Hz, 1H), 5.21, 5.25(ABq, J=12 Hz, 2H), 5.99(dd, J=5 Hz, J=9 Hz, 1H), 6.91(d, J=9 Hz, 2H), 7.04(s, 1H), 7.13∼7.45 (m, 16H).

IR ν (CHCl₃) cm⁻¹: 3390, 1783, 1715, 1680.

Preparation C-6

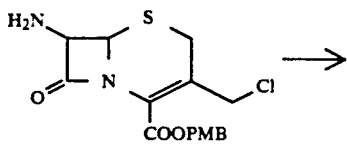

(1)

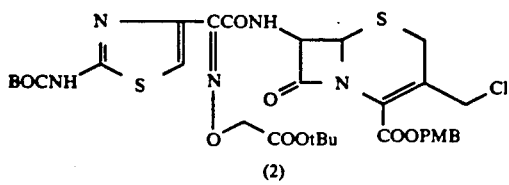

(2)

To a suspension of 7β-amino-3-chloromethyl-3-cephem-4-carboxylic acid p-methoxybenzyl ester (1) toluene-p-sulfonic acid salt (3.94 g; (7.28 mMol.) in dichloromethane (50 ml) keeping at 0° C. are added N-methylmorpholin (0.80 ml; 1 Eq.) and 2-(2-t-butoxycarbonylamino-4-thiazolyl)-2-t-butoxycarbonylmethoxyiminoacetic acid (3.80 g; 1.3 Eq.) and cooled at −40° C. To this mixture are added phenylphosphoric acid dichloride (1.41 ml; 1.3 Eq.) and N-methylmorpholin (2.41 ml; 3 Eq.), and the mixture is stirred at −40° to −15° C. for 1.5 hours. The reaction mixture is diluted with ethyl acetate, washed with water, diluted hydrochloric acid and water, dried, and concentrated under reduced pressure. The residue is purified by silica gel chromatography (toluene toluene: ethyl acetate) to give 7β-[2-(2-t-butoxycarbonylamino-4-thiazolyl)-2-t-butoxycarbonylmethoxyiminoacetamido]-3-chloromethyl-3-cephem-4-carboxylic acid p-methoxybenzyl ester (2) (5.20 g).

Yield: 95%.

(2) NMR δ (CDCl$_3$) ppm: 1.42(s, 9H), 1.53(s, 9H), 3.49, 3.59(ABq, J=18 Hz, 2H), 4.48(s, 2 H), 4.75(d, J=3 Hz, 2H), 5.06(d, J=5 Hz, 1H), 5.94 (dd, J=5 Hz, J=8 Hz, 1H), 6.90(d, J=9 Hz, 2H), 7.19(s, 1H), 7.35(d, J=9 Hz, 2H), 8.11(s, 1H), 8.76(d, J=8 Hz, 1H).

IR ν (CHCl$_3$) cm$^{-1}$: 3390, 1782, 1675.

Preparation C-7

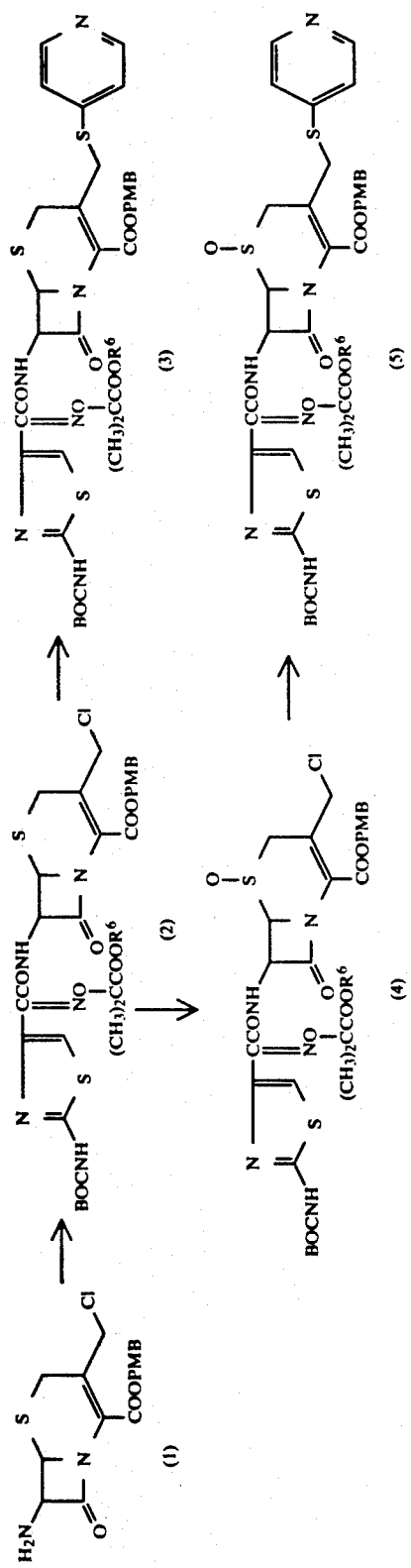

1) To a suspension of 7β-amino-3-chloromethyl-3-cephem-4-carboxylic acid p-methoxybenzyl ester (1) p-toluenesulfonate (2.705 g; 5 mMol.) in dichloromethane (50 ml) are added N-methylmorpholin (0.55 ml; 1 Eq.) and 2-(2-t-butoxycarbonylamino-4-thiazolyl)-2-(1-diphenylmethoxycarbonyl-1-methylethoxyimino)acetic acid (3.51 g; 1.3 Eq.) at 0° C. and then phenylphosphoric dichloride (0.97 ml; 1.3 Eq.) and N-methylmorpholin (1.65 ml; 3 Eq.) at −40° C., and the mixture is stirred at −40° to −10° C. for 1.5 hours. The reaction mixture is diluted with ethyl acetate, washed with water, diluted hydrochloric acid and water, dried, and concentrated under reduced pressure. The residue is purified by silica gel chromatography (toluene:ethyl acetate) to give 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester (2) (3.70 g).

Yield: 83%.

(2) NMR δ (CDCl$_3$) ppm: 1.55(s, 9H), 1.69(s, 6H), 3.32, 3.56(ABq, J=18 Hz, 2H), 3.87(s, 3H), 4.43, 4.55(ABq, J=12 Hz, 2H), 4.98(d, J=5 Hz, 1H), 5.25(d, J=5 Hz, 2H), 5.99(dd, J=5 Hz, J=9 Hz, 1H), 6.84~7.45(m, 16H).

IR ν (CHCl$_3$) cm$^{-1}$: 3490, 1783, 1715, 1680.

2) To a suspension of 7β-amino-3-chloromethyl-3-cephem-4-carboxylic acid p-methoxybenzyl ester (1) hydrochloride (72.1 g; 171 mMol.) in dichloromethane (1200 ml) are added N-methylmorpholin (18.8 ml; 1 Eq.) and 2-(2-t-butoxycarbonylamino-4-thiazolyl)-2-(1-diphenylmethoxycarbonyl-1-methylethoxyimino)acetic acid (95.5 g; 1.3 Eq.) at 0° C. and then phenylphosphoric acid dichloride (33.2 ml; 1.3 Eq.) and N-methylmorpholin (56.4 ml; 3 Eq.) at −40° C., and the mixture is stirred at −40° to −25° C. for 50 minutes. The reaction mixture is diluted with water. The formed dichloromethane layer is taken, washed with hydrochloric acid, water, aqueous sodium hydrogen carbonate, and water, dried, and concentrated under reduced pressure to give 7β-[2-(2-t-butoxycarbonylaminothiazol-4-yl)-2-(1-diphenylmethoxycarbonyl-1-methylethoxyimino)acetamido]-3-chloromethyl-3-cephem-4-carboxylic acid p-methoxybenzyl ester (2) (165 g).

Yield: 94%.

3) To a solution of 4-mercaptopyridine (178 mg; 2 Eq.) in N,N-di-methylformamide (10 ml) at 0° C. are added a solution of sodium methoxide in methanol (1.5 Eq.) and then 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester (2) (712 mg; 0.8 mMol.), and the mixture is stirred for 15 minutes. The reaction mixture is diluted with ethyl acetate, washed with water, dried and concentrated under reduced pressure. The residue is purified by silica gel chromatography (toluene: ethyl acetate) to give 7β-[2-(2-t-butoxycarbonylamino-4-thiazolyl)-2-(1-diphenylmethoxycarbonyl-1-methylethoxyimino)acetamido]-3-(4-pyridyl)thiomethyl-3-cephem-4-carboxylic acid p-methoxybenzyl ester (3) (497 mg).

Yield: 64%.

(3) NMR δ (CDCl$_3$) ppm: 1.52(s, 9H), 1.66(s, 6H), 3.29, 3.49(ABq, J=18 Hz, 2H), 3.96, 4.26 (ABq, J=15 Hz, 2H), 4.91(d, J=4.4 Hz, 1H), 5.21(s, 2H), 5.92(dd, J=4.4 Hz, J=8.4 Hz, 1H), 6.8~7.4(m, 13H), 8.39(d, J=7 Hz, 2H), 8.90 (brs, 1H).

4) To a solution of 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester (2) (6.43 g; 7.22 mMol.) in dichloromethane (64 ml) at −78° C. is added m-chloroperbenzoic acid (1.71 g; 1.1 Eq.), and the mixture is warmed to 0° C. The reaction mixture is diluted with ethyl acetate, washed with aqueous sodium sulfite, aqueous sodium hydrogen carbonate, and water, dried and concentrated under reduced pressure. The residue is purified by silica gel chromatography (toluene: ethyl acetate) to give 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1β-oxide (4) (5.68 g).

Yield: 87%.

(4) NMR δ (CDCl$_3$) ppm: 1.53(s, 9H), 1.65(s, 3H), 1.67(s, 3H), 3.34, 3.74(ABq, J=18.2 Hz, 2H), 3.82(s, 3H), 4.23, 5.01(ABq, J=14.4 Hz, 2H), 4.48(d, J=4.8 Hz, 1H), 5.27(s, 2H), 6.20(dd, J=4.8 Hz, J=10 Hz, 1H), ca. 6.9~7.4(m, 16H), 7.82(d, J=10 Hz, 1H), 8.30(brs, 1H).

IRν (CHCl$_3$) cm$^{-1}$: 3400, 1802, 1723, 1685.

5) To a solution of 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester (2) (165 g) in dichloromethane (1200 ml) at −70° C. is added 80% m-chloroperbenzoic acid (35.4 g), and the mixture is warmed up to −45° C. over 1 hour. The reaction mixture is diluted with 10% aqueous sodium sulfite (350 ml) and extracted with ethyl acetate. The extract is washed with 5% aqueous sodium hydrogen carbonate and water, dried and concentrated under reduced pressure. The residue is purified by silica gel chromatography to give 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1β-oxide (4) (127 g).

Yield: 93%.

6) To a solution of thiopyridone (489 mg; 2 Eq.) in N,N-dimethylformamide (20 ml) at 0° C. are added a solution of sodium methoxide in methanol (1.5 Eq.) and 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1β-oxide (4) (1.994 g; 2.2 mMol.), and the mixture is stirred for 10 minutes. Tthe reaction mixture is diluted with ethyl acetate, washed with water, dried and concentrated under reduced pressure. The residue is purified by silica gel chromatography (toluene:ethyl acetate) to give 7β-[2-(2-butoxycarbonylamino-4-thiazolyl)-2-(1-diphenylmethoxycarbonyl-1-methylethoxyimino)acetamido]-3-(4-pyridyl)thiomethyl-3-cephem-4-carboxylic acid p-methoxybenzyl ester 1β-oxide (5) (1.793 g).

Yield: 83%.

(5) NMRδ (CDCl$_3$) ppm: 1.55(s, 9H), 1.65(s, 3H), 1.68(s, 3H), 3.29, 3.81(ABq, J=18 Hz, 2H), 3.82(s, 3H), 3.81, 4.63(ABq, J=14.2 Hz, 2H), 4.42(d, J=4.8 Hz, 1H), 5.25, 5.29(ABq, J=12 Hz, 2H), 6.17(dd, J=4.8 Hz, J=9.8 Hz, 1H), 6.89~7.40(m, 17H), 7.77(d, J=9.8 Hz, 1H), 8.37(dd, J=1.6 Hz, J=7 Hz, 2H), 8.57(brs, 1H).

7) To a solution of 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1β-oxide (4) (50 g; 62.8 mMol.) and 4-mercaptopyridine (10.47 g; 1.5 Eq.) in N,N-dimethylformamide (250 ml) at 0° C. is added sodium hydrogen carbonate (7.9 g; 1.5 Eq.), and the mixture is stirred under ice cooling for 3.5 hours. The reaction mixture is diluted with ethyl acetate, washed with water, dried and concentrated under reduced pressure to give 7β-[2-(2-t-butoxycarbonylaminothiazol-4-yl)-2-(t-butoxycarbonyl-1-methylethoxyimino)acetamido]-3-(4-pyridyl)thiomethyl-3-cephem-4-carboxylic acid p-methoxybenzyl ester 1β-oxide (5) (41 g).

Yield: 75%.

B . $R^6$=t-butyl.

In a manner similar to above A, the following compounds can be prepared.

1) The treatment of 7β-amino-3-chloromethyl-3-cephem-4-carboxylic acid p-methoxybenzyl ester (1) p-toluenesulfonate in dichloromethane with triethylamine, N-methylmorpholine, phenylphosphoric dichloride, and 2-(2-t-butoxycarbonylamino-4-thiazolyl)-2-(1-t-butoxycarbonyl-1-methylethoxyimino)acetic acid gives 7β-[2-(2-t-butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester (2).

(2) NMR δ (CDCl$_3$) ppm: 1.53(s, 9H), 1.61(s, 3H), 1.64(s, 3H), 3.49, 3.64(ABq, J=17.6 Hz, 2H), 3.82(s, 3H), 4.46, 4.54(ABq, J=11.8 Hz, 2H), 5.05(d, J=5 Hz, 1H), 5.21, 5.27(ABq, J=11.2 Hz, 2H), 6.20(dd, J=5 Hz, J=10 Hz, 1H), 6.91(d, J=8 Hz, 2H), 7.19(s, 1H), 7.35(d, J=8 Hz, 2H), 8.20(d, J=10 Hz, 2H).

2) The oxidation of 7β-[2-(2-t-butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester (2) in dichloromethane at −78° C. with m-chloroperbenzoic acid gives 7β-[2-(2-t-butoxycarbonylamino-4-thiazolyl)-2-(1-t-butoxycarbonyl-1-methylethoxyimino)acetamido]-3-chloromethyl-3-cephem-4-carboxylic acid p-methoxybenzyl ester 1β-oxide (4).

(4) NMR δ (CDCl$_3$) ppm: 1.42(s, 9H), 1.53(s, 9H), 1.58(s, 3H), 1.60(s, 3H), 3.42, 3.82(ABq, J=18.9 Hz, 2H), 3.82(s, 3H), 4.23, 5.05(ABq, J=12.6 Hz, 2H), 4.58(d, J=5 Hz, 1H), 5.25, 5.29(ABq, J=11 Hz, 2H), 6.21(dd, J=5 Hz, J=10 Hz, 1H), 6.92(d, J=8 Hz, 2H), 7.29(s, 1H), 7.36(d, J=8 Hz, 2H), 7.90(d, J=10 Hz, 1H).

3) The reaction of 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1β-oxide (4) with 4-mercaptopyridine sodium salt gives 7β-[2-(2-t-butoxycarbonylamino-4-thiazolyl)-2-(1-diphenylmethoxycarbonyl-1-methylethoxyimino)acetamido]-3-(4-pyridyl)thiomethyl-3-cephem-4-carboxylic acid p-methoxybenzyl ester 1β-oxide (5).

Yield: 83%.

(5) NMR δ (CDCl$_3$) ppm: 1.41(s, 9H), 1.53(s, 9H), 1.57(s, 3H), 1.59(s, 3H), 3.37, 3.86(ABq, J=18 Hz, 2H), 3.80, 4.65(ABq, J=14 Hz, 2H), 4.52(d, J=5 Hz, 1H), 5.22, 5.27(ABq, J=11.8 Hz, 2H), 6.17(dd, J=5 Hz, J=10 Hz, 1H), 6.89(d, J=8.6 Hz, 2H), 7.06(d, J=6.5 Hz, 2H), 7.27(s, 1H), 7.36(d, J=8.6 Hz, 2H), 7.85(d, J=10 Hz, 1H), 8.35(d, J=6.5 Hz, 2H).

Preparation C-8

1) To a suspension of 7β-amino-3-chloromethyl-3-cephem-4-carboxylic acid p-methoxybenzyl ester (1) hydrochloride (4.05 g; 10 mMol.) in dichloromethane (100 ml) is washed with aqueous sodium hydrogen carbonate.

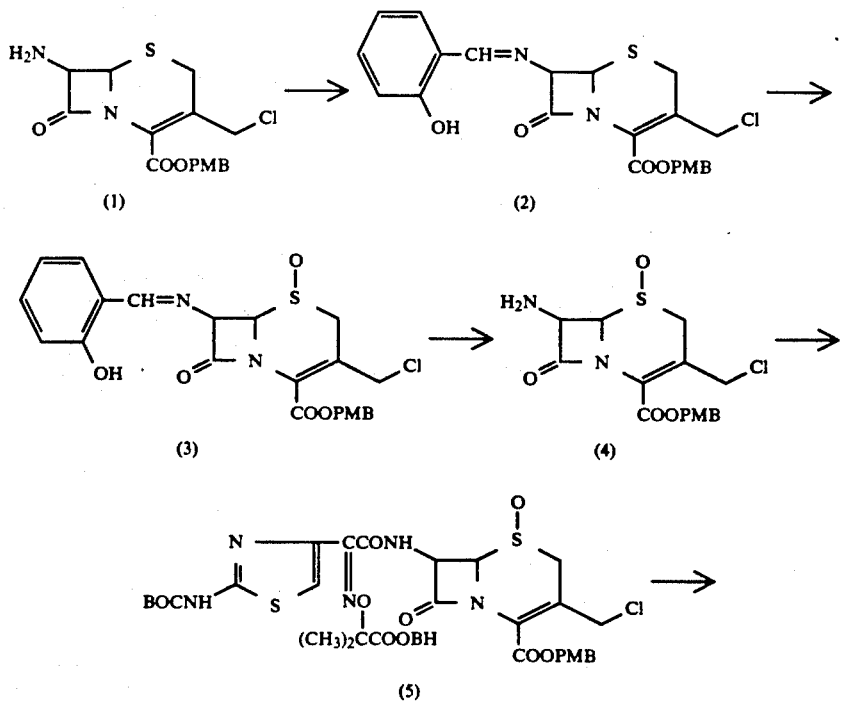

-continued

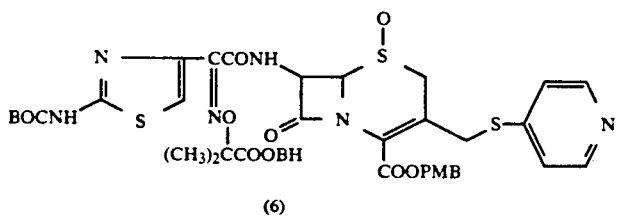

(6)

The resulting solution of 7β-amino-3-chloromethyl-3-cephem-4-carboxylic acid p-methoxybenzyl ester (1) in dichloromethane is dried and concentrated under reduced pressure. To a solution of the residue in a mixture of dichloromethane (40 ml) and methanol (90 ml) is added salicylaldehyde (1.29 ml; 1.2 Eq.), and the mixture is stirred at room temperature for 3 hours and concentrated. The separating crystals are collected by filtration, washed with methanol, and dried to give 7β-o-hydroxybenzalamino-3-chloromethyl-3-cephem-4-carboxylic acid p-methoxybenzyl ester (2) (4.29 g).

Yield: 91%.

(2) NMR δ (CDCl$_3$) ppm: 3.46, 3.71(ABq, J=18.4 Hz, 2H), 3.82(s, 3H), 4.38, 4.60(ABq, J=11.8 Hz, 2H), 5.14(d, J=5 Hz, 1H), 5.26(s, 2H), 5.35(d, J=5 Hz, 1H), 6.8~7.4(m, 8H), 8.63(d, J=1.2 Hz, 1H).

2) To a solution of 7β-o-hydroxybenzalamino-3-chloromethyl-3-cephem-4-carboxylic acid p-methoxybenzyl ester (2) (7.94 g; 16.8 mMol.) in dichloromethane (100 ml) is added m-chloroperbenzoic acid (3.99 g; 1.1 Eq.) under ice cooling, and the mixture is stirred at room temperature for 1 hour. The reaction mixture is washed with aqueous sodium thiosulfate, dried, and concentrated under reduced pressure. The residue is treated with ether and methanol. The resulting solid is collected by filtration to give 7β-o-hydroxybenzalamino-3-chloromethyl-3-cephem-4-carboxylic acid p-methoxybenzyl ester 1α-oxide (3) (5.3 g).

Yield: 65%.

(3) NMR δ (CDCl$_3$) ppm: 3.81(s, 3H), 3.70, 4.10(ABq, J=16.8 Hz, 2H), 4.39, 4.55(ABq, J=12 Hz, 2H), 4.83(d, J=4.6 Hz, 1H), 5.25(s, 2H), 5.41 (d, J=4.6 Hz, 1H), 6.85~7.45(m, 8H), 8.61(s, 1H).

3) To a solution of 7β-o-hydroxybenzalamino-3-chloromethyl-3-cephem-4-carboxylic acid p-methoxybenzyl ester 1α-oxide (3) (1 g; 2.05 mMol.) in dioxane (5 ml) under ice cooling is added concentrated hydrochloric acid (2 ml). The reaction mixture is diluted with ether and water, and the formed water layer is separated. The layer is neutralized with sodium hydrogen carbonate and extracted with dichloromethane. The extract is dried, and concentrated under reduced pressure. The residue is triturated with ether and forming solid is collected and washed with hexane to give 7β-amino-3-chloromethyl-3-cephem-4-carboxylic acid p-methoxybenzyl ester 1α-oxide (4) (0.587 g).

Yield: 74%.

(4) NMR δ (CDCl$_3$) ppm: 3.82(s, 3H), 3.63, 4.15(ABq, J=16.9 Hz, 2H), 4.37, 4.51(ABq, J=12.1 Hz, 2H), 4.56(d, J=4.6 Hz, 1H), 4.98(d, J=4.6 Hz, 1H), 5.24(s, 2H), 6.90(d, J=8.8 Hz, 2H), 7.34(d, J=8.8 Hz, 2H).

4) To a solution of 7β-amino-3-chloromethyl-3-cephem-4-carboxylic acid p-methoxybenzyl ester 1α-oxide (4) (1.45 g; 3.77 mMol.) in dichloromethane (10 ml) at −40° C. are added 2-(2-t-butoxycarbonylaminothiazol-4-yl)-2-(1-diphenylmethoxycarbonyl-1-methylethoxy)iminoacetic acid (2.65 g; 1.3 Eq.), N-methylmorpholine (1.25 ml; 3 Eq.), phenylphosphoric acid dichloride (0.73 ml; 1.3 Eq.), and the mixture is stirred at −30° to −20° C. for 2 hours. The reaction mixture is poured into 1N-hydrochloric acid and extracted with dichloromethane. The extract is washed with water, dried and concentrated under reduced pressure. The residue is purified by silica gel chromatography (toluene:ethyl acetate) to give 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1α-oxide (5) (1.39 g).

Yield: 41%.

(5) NMR δ (CDCl$_3$) ppm: 1.53(s, 9H), 1.66(s, 3H), 1.72(s, 3H), 3.01(s, 3H), 3.55, 4.12(AB q, J=16.6 Hz, 2H), 4.44, 4.53(ABq, J=12.3 Hz, 2H), 4.60(d, J=4.8 Hz, 1H), 5.20, 5.28(ABq, J=11.2 Hz, 2H), 5.56(dd, J=7.8 Hz, J=4.8 Hz, 1H), 6.83(s, 1H), 6.91(d, J=8.8 Hz, 2H), 7.4~7.1(m, 11H), 7.35(d, J=8.8 Hz, 2H), 7.61(d, J=7.8 Hz, 1H).

5) To a solution of 7β-[2-(2-t-butoxycarbonylamino-4-thiazolyl)-2-(1-diphenylmethoxycarbonyl-1-methylethoxyimino)acetamido]-3-chloromethyl-3-cephem-4-carboxylic acid p-methoxybenzyl ester 1α-oxide (5) (0.28 g; 0.31 mMol.) in N,N-dimethylformamide (1.7 ml) are added 4-mercaptopyridine (41.2 mg; 1.2 Eq.) and sodium hydrogen carbonate (31 mg; 1.2 Eq.), and the mixture is stirred at room temperature for 40 minutes. The reaction mixture is diluted with ice water. The separating solid is collected by filtration, dissolved in ethyl acetate, and purified by silica gel chromatography (toluene:acetonitrile) to give 7β-[2-(2-t-butoxycarbonylamino-4-thiazolyl)-2-(1-diphenylmethoxycarbonyl-1-methylethoxyimino)acetamido]-3-(4-pyridyl)thiomethyl-3-cephem-4-carboxylic acid p-methoxybenzyl ester 1α-oxide (6) (194 mg).

Yield: 64%.

(6) NMRδ (CDCl$_3$) ppm: 1.53(s, 9H), 1.65(s, 3H), 1.71(s. 3H), 3.56, 4.12(ABq, J=16.4 Hz, 2H), 4.10, 4.35(ABq, J=13.8 Hz, 2H), 4.47(d, J=4.8 Hz, 1H), 5.35~5.20(m, 3H), 6.83(s, 1H), 6.88(d, J=8.8 Hz, 2H), 7.10(d, J=7.8 Hz, 2H), 7.2~7.6(m, 12H), 8.35(d, J=7.8 Hz, 2H).

Preparation C-9

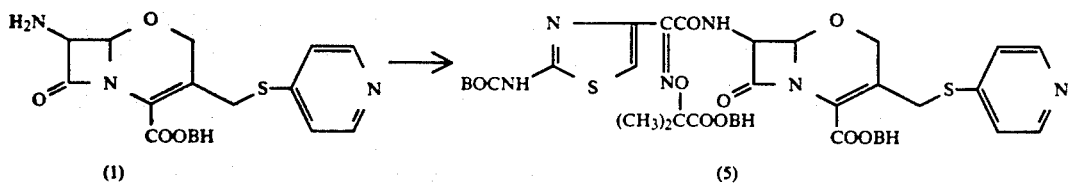

To a solution of 7β-amino-3-(4-pyridyl)thiomethyl-1-dethia-1-oxa-3-cephem-4-carboxylic acid diphenylmethyl ester (1) (947 mg; 2 mMol.) and 2-(2-t-butoxycarbonylamino-4-thiazolyl)-2-(1-diphenylmethoxycarbonyl-1-methylethoxyimino)acetic acid (1.619 g 1.5 Eq.) in dichloromethane (20 ml) cooling at −40° C. are added N-methylmorpholin (0.66 ml; 3 Eq.) and phenylphosphoric acid dichloride (0.45 ml; 1.5 Eq.), and the mixture is stirred at −40° to −10° C. for 1 hour. The reaction mixture is diluted with ethyl acetate, washed with water, dried, and concentrated under reduced pressure. The residue is purified by silica gel chromatography (toluene:ethyl acetate) to give 7β-[2-(2-t-butoxycarbonylamino-4-thiazolyl)-2-(1-diphenylmethoxycarbonyl-1-methylethoxyimino)acetamido]-3-(4-pyridyl)thiomethyl-1-dethia-1-oxa-3-cephem-4-carboxylic acid diphenylmethyl ester (2) (641 mg).

Yield: 32%.

(2) NMR δ (CDCl₃) ppm: 1.55(s, 9H), 1.63(s, 3H), 1.69(s, 3H), 3.77, 4.41(ABq, J=14.4 Hz, 2H), 4.07, 4.29(ABq, J=18 Hz, 2H), 4.92(d, J=4 Hz, 1H), 5.80(dd,J=4 Hz, J=8 Hz, 1H), 6.83~7.10(m, 30H), 8.34(d, J=5 Hz, 2H), 9.11(s, 1H).

IR ν (CHCl₃) cm⁻¹: 3400, 1797, 1724, 1685.

Preparation C-10 pressure. The residue is purified by silica gel chromatography (toluene:ethyl acetate=9:1 to 5:1) to give amide (2) (2.43 g).

Yield: 80%.

(2) NMR (CDCl₃) δ : 1.48(s, 3H), 1.50(s, 3H), 1.55(s, 9H), 3.45, 3.61 (ABq, J=18.5 Hz, 2H), 3.80(s, 3H), 4.45, 4.51(ABq, J=12.5 Hz, 2H), 4.96 (d, J=5 Hz, 1H), 5.14(s, 2H), 5.23, 5.26 (ABq, J=11.5 Hz, 2H), 5.83(dd, J=5 Hz, J=8.5 Hz, 1H), 6.46(s, 1H), 6.85(s, 1H), 6.89(d, J=9 Hz, 2H), 7.15~7.38(m, 7H), 7.99(brs, 1H), 8.22(d, J=8.5 Hz, 2H) ppm.

2) To a solution of 4-mercaptopyridine (400 mg; 1.2 Eq.) in ethanol (3 ml) is added 1N-sodium hydroxide (3.0 ml; 1 Eq.) at room temperature. After 10 minutes the mixture is concentrated in vacuum. To the solution of the residue in N,N-dimethylformamide (10 ml) at −30° to −35° C. is added chloromethyl compound (2) (2.4 g; 3 mMol.), and stirred at room temperature for 25 minutes. The reaction mixture is washed with 10% aqueous citric acid and ethyl aceate and then with water, dried, and concentrated in vacuum. The residue is purified by silica gel chromatography (toluene:ethyl acetate=2:1 to 1:1) to give pyridylthiomethyl compond (3) (2.35 g).

Yield: 90%.

(3) NMR (CDCl₃) δ : 1.47(s, 3H), 1.48(s, 3H), 1.54(s,

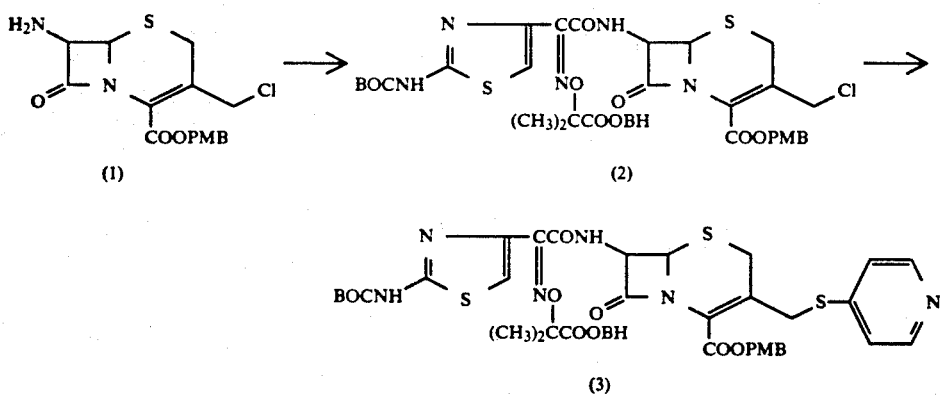

1) To a suspension of 3-chloromethylcephemamine (1) (1.4 g; 3.8 mMol.) and carboxylic acid (2) (1.7 g; 1 Eq.) in dichloromethane (30 ml) at −35° C. are added N-methylmorpholin (2.1 ml; 5 Eq.) and dichlorophosphoric acid monophenyl ester (0.63 ml; 1.1 Eq.), and the mixture is stirred for 1.5 hours. The reaction mixture is washed with aqueous 10% citric acid ethyl acetate and then with water, dried, and concentrated under reduced 9H), 3.44, 3.49 (ABq, J=19 Hz, 2H), 3.79(s, 3H), 3.99, 4.30(ABq, J=13 Hz, 2H), 4.91(d, J=5 Hz, 1H), 5.10, 5.14(ABq, J=12.5 Hz, 2H), 5.20, 5.25(ABq, J=11.5 Hz, 2H), 5.73 (dd, J=5 Hz, J=9 Hz, 1H), 6.42(s, 1H), 6.82(s, 1H), 6.87(d, J=8.8 Hz, 2H), 7.15~7.36(m, 9H), 8.38(d, J=6 Hz, 2H), 9.50(brs, 1H) ppm.

TABLE 1

Reaction condition (1)

Pyridinio formation:

TABLE 1-continued

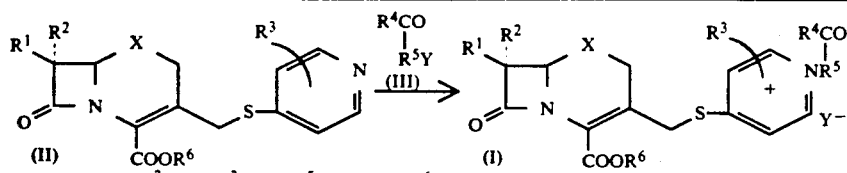

(II) → (I)

$R^2 = H$, $R^3 = H$, $R^5 = CH_2$, & $R^6 = PMB$ unless otherwise specified.

| No. | starting cephalosporin (II) R¹ | R⁴ | X | Y | mg | cathecol (III) mg/mol | DCM ml | temp. °C | time min | yield mg | crop % | additive mg |
|---|---|---|---|---|---|---|---|---|---|---|---|---|
| 1 | G | 3,4-OH | S | Cl | 56262 | 224/1.2 | DMF 4 | r.t. | o.n. | 840 | 100 | NaI 165 |
| 2 | FMOX | 3,4-OAc | MO | I | 62828 | 905/2.5 | 6 | r.t. | o.n. | 865 | 96 | — |
| 3 | BOCCTX | 2,3-PMB | βSO | Br | 89191 | 622/1.1 | 9 | r.t. | 1080 | 1392 | 96 | — |
| 4 | BOCCTX | 3,4-PMB | S | Br | 43636 | 340/1.2 | 2 | r.t. | 1140 | 675 | 94 | — |
| 5 | BOCCAZBH | 2,3-PMB | βSO | Br | 170000 | 1350/1.65 | 6 | r.t. | 1440 | 2300 | 97 | — |
| 6 | BOCCAZBH | 3,4-OAc | S | I | 122020 | 549/1.5 | 4 | r.t. | 1200 | 1440 | 86 | — |
| 7 | BOCCAZBH | 3,4-PMB | S | Br | 48383 | 353/1.5 | 2.5 | r.t. | 900 | 700 | 97 | — |
| 8 | BOCCAZBH | 3,4-PMB | βSO | Br | 117777 | 792/1.4 | 4 | r.t. | 1140 | 1590 | 97 | — |
| 9 | BOCCAZBH | 3,4-PMB | O | Br | 62020 | 460/1.5 | 3 | r.t. | o.n. | 800 | 88 | — |
| 10 | BOCCAZtBu | 3,4-OAc | S | Br | 45353 | 227/1.2 | An 2 | r.t. | 300 | 584 | 91 | — |
| 11 | BOCCAZtBu | 3,4-OAc | βSO | Br | 30808 | 158/1.3 | An 2 | r.t. | 60 | 399 | 92 | — |
| 12 | BOCCAZtBu | 3,4-PMB-6-Me | S | Br | 43636 | 495/1.0 | An 5 | r.t. | 360 | 594 | 87 | — |
| 13 | BOCCAZtBu | 3,4-PMB-6-Me | βSO | Br | 43636 | 485/1.0 | An 5 | r.t. | 300 | 601 | 89 | — |
| 14 | BOCCAZtBu | 3,4-PMB-2-Cl | βSO | Br | 87171 | 657/1.3 | An 10 | r.t. | 1440 | 1010 | 73 | — |
| 15 | BOCCAZtBu | 3,4-PMB-5-Cl | S | Br | 18888 | 101/1.3 | An 3 | r.t. | o.n. | 191 | 70 | — |
| 16 | BOCCAZtBu | 3,4-PMB-5-Cl | βSO | Br | 192 | 101/1.0 | An 3 | r.t. | o.n. | 201 | 73 | — |
| 17 | BOCCAZtBu | 3,4-PMB-6-Cl | S | Br | 256 | 201/1.3 | An 3 | r.t. | o.n. | 260 | 64 | — |
| 18 | BOCCAZtBu | 3,4-PMB-6-Cl | βSO | Br | 261 | 202/1.0 | An 3 | r.t. | o.n. | 394 | 95 | — |
| 19 | BOCCAZtBu | 3,4-OH-2,5-Cl | βSO | Cl | 2610 | 1000/1.2 | An 25 | r.t. | 2 days | 3330 | 95 | NaBr 620 |
| 20 | CAZtBu | 3,4-OAc(R⁵ = MeCH) | S | Cl | 1000 | 443/1.2 | 3 | r.t. | 480 | 1290 | 94 | NaI 584 |
| 21 | BOCCETBBzl | 3,4-PMB(R⁶ = BH) | S | Br | 280 | 150/1.0 | An 2 | 3° C. | 7 days | 376 | 87 | — |

Reaction conditions (2)
Carboxy deprotection:
(BOC in R¹ if present, is eliminated)

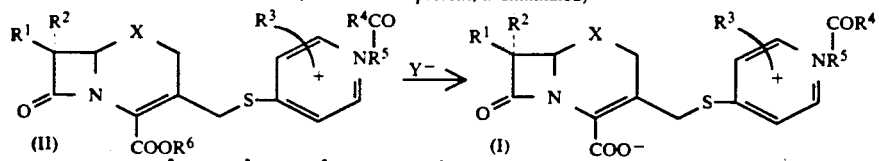

(II) → (I)

$R^2 = H$, $R^3 = H$, $R^5 = CH_2$, & $R^6 = PMB$ unless otherwise specified.

| No. | starting cephalosporin (II) R¹ | R⁴ | X | Y | mg | DCM ml | MeOPh ml | MeNO₂ ml | AlCl₃ mg | temp. °C | time min. | crop mg | yield % |
|---|---|---|---|---|---|---|---|---|---|---|---|---|---|
| 1 | G | 3,4-OH | S | I | 830 | — | 2.5 | — | TFA 5 ml | r.t. | 120 | 95 | 16 |
| 2 | FMOX | 3,4-OA | MO | I | 840 | 8 | 1 | — | TFA 2 ml | 0 | 30 | 165 | 26 |
| 3 | BOCCTX | 3,4-PM | S | Br | 670 | 7 | 1 | 5 | 890 | −40~−30 | 30 | 291 | 56 |
| 4 | BOCCTX | 2,3-PM | βSO | Br | 450 | — | 8 | — | 590 | −40 | 60 | 196 | 79 |
| 5 | BOCCTX | 2,3-PM | S | Br | 799 | 7 | 5 | — | 1070 | −40 | 60 | 275 | 63 |
| 6 | BOCCAZBH | 2,3-PMB | S | Br | 1220 | — | 12 | 3 | 1430 | −40~−30 | 45 | 289 | 47 |
| 7 | BOCCAZBH | 2,3-PMB | βSO | Br | 1000 | — | 11 | 3 | 1160 | −45~−30 | 40 | 392 | 61 |
| 8 | BOCCAZBH | 3,4-OAc | S | I | 1400 | — | 9 | 2 | 1400 | −40~−30 | 60 | 505 | 60 |
| 9 | BOCCAZBH | 3,4-PMB | S | Br | 700 | 10 | 1 | 5 | 1000 | −40~−30 | 30 | 298 | 84 |
| 10 | BOCCAZBH | 3,4-PMB | βSO | Br | 1590 | 10 | 10 | — | 2400 | −40 | 40 | 684 | 84 |
| 11 | BOCCAZBH | 3,4-PMB (R⁶ = BH) | O | Br | 880 | 10 | 1 | 5 | 1200 | −40~−30 | 30 | 397 | 93 |
| 12 | BOCCAZtBu | 3,4-OH (R³ =(CH₂)₃) | S | Cl | 468 | 5 | 1 | — | 690 | −40 | 60 | 30 | 9 |
| 13 | BOCCAZtBu | 3,4-OH (R³ =(CH₂)₃) | βSO | I | 221 | 4 | 1 | — | 320 | −40 | 60 | 65 | 41 |
| 14 | BOCCAZtBu | 3,4-OAc | βSO | Br | 390 | — | 1 | — | TFA 4 ml | r.t. | 40 | 229 | 77 |
| 15 | BOCCAZtBu | 3,4-OAc | S | Br | 575 | — | 1 | — | TFA 6 ml | r.t. | 60 | 367 | 84 |
| 16 | CAZtBu | 3,4-OAc (R⁵ = MeCH) | S | — | 1390 | — | 11 | 6 | 877 | −40 | 30 | 404 | 38 |
| 17 | BOCCAZtBu | 3,4-PMB-6-Me | S | Br | 570 | 6 | 12 | — | 600 | −35~−25 | 60 | 245 | 77 |
| 18 | BOCCAZtBu | 3,4-PMB-6-Me | βSO | Br | 593 | 6 | 12 | — | 600 | −35~−25 | 60 | 214 | 64 |
| 19 | BOCCAZtBu | 3,4-PMB-2-Cl | S | Br | 987 | — | 6 | — | 1400 | −50~−20 | 60 | 525 | 82 |
| 20 | BOCCAZtBu | 3,4-PMB-2-Cl | βSO | Br | 6620 | — | 60 | — | 9620 | −40~−20 | 60 | 2290 | 60 |
| 21 | BOCCAZtBu | 3,4-PMB-5-Cl | S | Br | 191 | — | 3.5 | — | 150 | −20~−5 | 180 | 76 | 70 |
| 22 | BOCCAZtBu | 3,4-PMB-5-Cl | βSO | Br | 201 | — | 3.7 | — | 290 | −20~−5 | 180 | 76 | 66 |
| 23 | BOCCAZtBu | 3,4-PMB-6-Cl | S | Br | 260 | — | 6 | — | 380 | −20~0 | 180 | 128 | 87 |
| 24 | BOCCAZtBu | 3,4-PMB-6-Cl | βSO | Br | 394 | — | 6 | — | 570 | −20~0 | 180 | 130 | 57 |
| 25 | BOCCAZtBu | 3,4-OH-2,5-Cl | βSO | Br | 1500 | 10 | 10 | — | 3800 | −40~−30 | 60 | 781 | 75 |

TABLE 1-continued

| 26 | BOCCETBBH | 3,4-PMB | S | Br | 376 | — | 4 | 4 | 560 | 0~r.t. | 180 | 142 | 71 |

Note) p-methoxybenzyl, diphenylmethyl and t-butyl are hydrolyzed but acetate remains intact.

Reaction condition (3)
Pyridylthio introduction

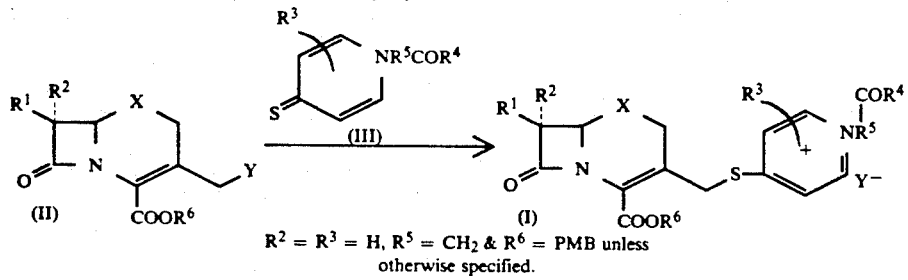

$R^2 = R^3 = H$, $R^5 = CH_2$ & $R^6 = PMB$ unless otherwise specified.

| No. | starting cephalosporin (II) | | | | | thiopyridone (III) mg | DMF ml | MeCN ml | temp. °C. | time min. | crop yield | |
|---|---|---|---|---|---|---|---|---|---|---|---|---|
| | $R^1$ | $R^4$ | X | Y | mg | | | | | | mg | % |
| 1 | BOCCAZtBu | 3,4-OHHR | S | Cl | 780 | 301 | 2 | 3 | r.t. | 150 | 468 | 43 |
| 2 | BOCCAZtBu | 3,4-OHHR | βSO | I | 796 | 301 | 1 | 3 | r.t. | 240 | 221 | 20 |

Reaction condition (4)
Hydrolysis of acetoxy

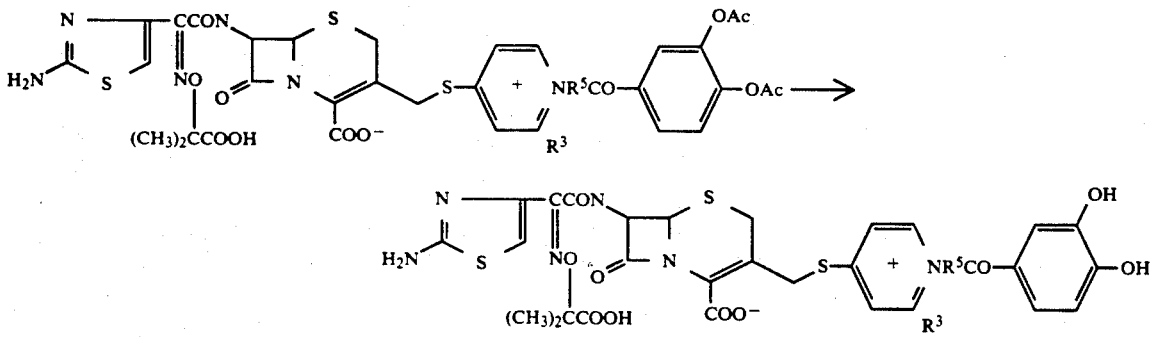

$R^3 = H$ & $R^5 = CH_2$ unless otherwise specified.

| No. | starting cephalosporin | | | | | NaHCO₃ mg/Eq. | water ml | temp. °C. | time min. | crop yield | |
|---|---|---|---|---|---|---|---|---|---|---|---|
| | $R^1$ | $R^4$ | X | Y | mg | | | | | mg | % |
| 1 | CAZ | 3,4-OAc | S | — | 400 | 380/9 | 8 | r.t. | 360 | 216 | 59 |
| 2 | CAZtBu | 3,4-OAc ($R^5$ = MeCH) | S | — | 240 | 244/9 | 5 | r.t. | 360 | 151 | 68 |

Reaction condition (5)
Reduction of sulfoxide

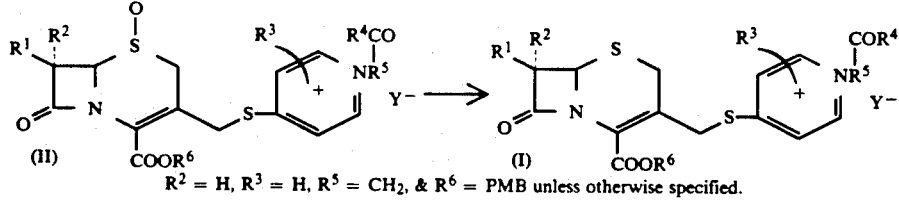

$R^2 = H$, $R^3 = H$, $R^5 = CH_2$, & $R^6 = PMB$ unless otherwise specified.

| No. | starting cephalosporin (II) | | | | PCl₃ Eq. | DMA ml | DCM ml | temp. °C. | time min. | crop yield | |
|---|---|---|---|---|---|---|---|---|---|---|---|
| | $R^1$ | $R^4$ | Y | mg | | | | | | mg | % |
| 1 | BOCCTX | 2,3-PMB | Br | 930 | 1.5 | 1.5 | 5 | −50 → −30 | 90 | 799 | 87 |
| 2 | BOCCAZBH | 2,3-PMB | Br | 1300 | 2 | 2 | 20 | −50 → −30 | 90 | 1220 | 95 |
| 3 | BOCCAZtBu | 3,4-PMB-2-Cl | Br | 987 | 2 | 1 | 10 | −50 → −20 | 120 | 525 | 82 |

TABLE 2

Physical constants of esters $R^2 = H, R^3 = H, R^5 = CH_2,$ & $R^6 = PMB$ unless otherwise specified.

| No. | R¹ | R⁴ | X | Y | IR (CHCl₃) | NMR: δ (CDCl₃) ppm |
|---|---|---|---|---|---|---|
| 1 | G | 3,4-OH | S | I | 1780, 1720, 1670. [Nujol] | 3.53(d, J=3.7Hz, 2H), 3.73(s, 3H), 3.58, 3.79(ABq, J=18Hz, 2H), 4.35(s, 2H), 5.17(d, J=5Hz, 1H), 5.23(s, 2H), 5.74 (dd, J=5Hz, J=8Hz, 1H), 6.16(s, 2H), 6.88(d, J=8.6Hz, 1H), 6.95(d, J=8.2Hz, 1H), 7.15–7.4(m, 9H), 8.03(d, J=7Hz, 2H), 8.64(d, J=7Hz, 2H), 9.15(d, J=8Hz, 1H). [CD₃SOCD₃] |
| 2 | FMOX R² = MeO, R⁶ = BH, X = O | 3,4-OAc | MO | I | 3380, 1780, 1730sh 1700. [Chf] | nd. |
| 3 | BOCCTX | 2,3-PMB | S | I | 3415, 1790, 1725, 1690. | nd. |
| 4 | BOCCTX | 2,3-PMB | SO | Br | 3390, 1800, 1724, 1686. | nd. |
| 5 | BOCCTX | 3,4-PMB | S | Br | 3400, 1790, 1728, 1692. | nd. |
| 6 | BOCCAZ BH | 2,3-PMB | S | Br | 1786, 1722, 1684. | 3.56(d, J=18Hz, 1H), 4.36(s, 2H), 5.10–5.25(m, 6H), 5.29 (d, J=5Hz, 1H), 5.95(dd, J=5Hz, J=8Hz, 1H), 6.07(s, 2H), 6.73–7.66(m, 24H), 8.02(d, J=8Hz, 2H), 8.67(d, J=8Hz, 2H), 9.66(d, J=8Hz, 1H). |
| 7 | BOCCAZ BH | 2,3-PMB | SO β | Br | 1800, 1720, 1682. | 1.47(s, 9H), 1.56(s, 3H), 1.57(s, 3H), 3.71(s, 3H), 3.73 (s, 3H), 3.79(s, 3H), 4.42(s, 2H), 5.10(d, J=5Hz, 1H), 5.17(s, 2H), 5.21(s, 2H), 5.27(s, 2H), 5.98–6.20(m, 3H), 6.78–7.53(m, 26H), 8.02(d, J=7Hz, 2H), 8.65(d, J=7Hz, 2H). |
| 8 | BOCCAZ tBu | 3,4-OH | S | Cl | 3400, 1790, 1725, 1690sh. | nd. |
| 9 | BOCCAZ tBu | 3,4-OH | SO β | Cl | 1798, 1721, 1675. | nd. |
| 10 | BOCCAZ tBu | 3,4-OH | SO β | Br | nd | 1.36(s, 6H), 1.45(s, 18H), 3.27(s, 3H), 3.85, 4.02(ABq, J=17.8Hz, 2H), 4.38, 4.44(ABq, J=15Hz, 2H), 5.08(d, J=4Hz, 1H), 5.23(s, 2H), 6.07(dd, J=4Hz, J=8.9Hz, 1H), 6.15(s, 2H), 6.87(d, J=8.6Hz, 2H), 6.94(d, J=8.2Hz, 1H), 7.28–7.53 (m, 5H), 8.00(d, J=7.1Hz, 2H), 8.50(d, J=8.9Hz, 1H), 8.62 (d, J=7.1Hz, 2H). |
| 11 | BOCCAZ tBu | 3,4-OAc | S | Br | nd | 1.39(s, 9H), 1.42(s, 3H), 1.43(s, 3H), 2.35(s, 6H), 3.59, 3.82(ABq, J=19Hz, 2H), 3.73(s, 3H), 4.32(brs, 2H), 5.23(s, 1H), 5.26(d, J=4.9Hz, 1H), 5.90(dd, J=4.9Hz, J=8Hz, 2H), 6.27(brs, 2H), 6.71(s, 1H), 6.88(d, J=8.6Hz, 2H), 7.28 (brs, 2H), 7.35(d, J=8.6Hz, 2H), 7.61(d, J=8.4Hz, 1H), 7.98–8.07(m, 4H), 8.65(d, J=6.8Hz, 2H), 9.45(d, J=8Hz, 1H). [CD₃SOCD₃] |
| 12 | BOCCAZ tBu | 3,4-OAc | SO β | Br | nd. | 1.38(s, 9H), 1.45(s, 3H), 1.46(s, 3H), 2.35(s, 6H), 3.74 (s, 3H), 3.87, 4.02(ABq, J=19Hz, 2H), 4.42(brs, 2H), 5.09 (d, J=4.5Hz, 1H), 5.27(s, 2H), 6.07(dd, J=4.5Hz, J=8.8Hz, 1H), 6.27(brs, 2H), 6.80(s, 1H), 6.89(d, J=8.4Hz, 2H), 7.27(brs, 2H), 7.37(d, J=8.4Hz, 2H), 7.61(d, J=8.3Hz, 1H), 7.98–8.07(m, 4H), 8.26(d, J=8.8Hz, 1H), 8.65(d, J=6.8Hz, 2H). [CD₃SOCD₃] |
| 13 | BOCCAZ tBu | 3,4-PMB | SO β | Br | 3390, 1803, 1725, 1688. | nd. |
| 14 | BOCCAZ BH | 3,4-OAc | S | I | 1782, 1722, 1690sh | 1.52(s, 9H), 1.65(s, 3H), 1.68(s, 3H), 2.29(s, 6H), 3.34, 3.61(ABq, J=18.5Hz, 2H), 3.75(s, 3H), 4.36(d, J=4Hz, 2H), 5.01(d, J=5Hz, 1H), 5.19, 5.29(ABq, J=12Hz, 2H), 5.92(dd, J=5Hz, J=9Hz, 1H), 6.55(s, 2H), 6.87(d, J=8.6Hz, 2H), 6.87(s, 1H), 7.20–7.50(m, 13H), 7.36(d, J=8.6Hz, 2H), 7.66 (d, J=6.5Hz, 2H), 7.97(s, 1H), 8.03(d, J=9Hz, 1H), 8.54(d, J=6.5Hz, 2H). |
| 15 | BOCCAZ BH | 3,4-PMB | S | Br | 3400, 1790, 1723, 1690. | nd. |
| 16 | BOCCAZ BH | 3,4-PMB | SO | Br | 3390, 1805, 1726, 1690. | nd. |
| 17 | BOCCAZ tBu | 3,4-PMB-6-Me | S | Br | nd. | 1.42(s, 9H), 1.53(s, 9H), 1.61(s, 3H), 1.64(s, 3H), 2.43 (s, 3H), 3.30, 3.56(ABq, J=20Hz, 2H), 3.74(s, 3H), 3.75 (s, 3H), 3.80(s, 3H), 4.21(brs, 2H), 4.99(d, J=5.2Hz, 1H), 5.07(s, 2H), 5.27(s, 2H), 5.18, 5.29(ABq, J=12.5Hz, 2H), 5.98(dd, J=5.2Hz, J=8.7Hz, 1H), 6.73–6.92(m, 9H), 7.31–7.52(m, 9H), 7.87(s, 1H), 8.20(d, J=8.7Hz, 1H), 8.67(d, J=6.7Hz, 2H). |
| 18 | BOCCAZ tBu | 3,4-PMB-2-Cl | SO β | — | 1800, 1719, 1670, 1620, | 1.43(s, 9H), 1.54(s, 9H), 1.58(s, 3H), 1.59(s, 3H), 2.88, 2.89(2×d, 2H), 3.76(s, 3H), 3.80(s, 3H), 3.85(s, 3H), |

TABLE 2-continued

Physical constants of esters

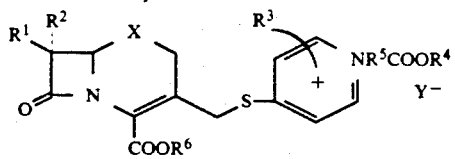

$R^2 = H$, $R^3 = H$, $R^5 = CH_2$, & $R^6 = PMB$ unless otherwise specified.

| No. | $R^1$ | $R^4$ | X | Y | IR (CHCl$_3$) | NMR: δ (CDCl$_3$) ppm |
|---|---|---|---|---|---|---|
|  |  |  |  |  | 1611. | 4.30, 4.66(ABq, J=18Hz, 2H), 4.94(d, J=5Hz, 1H), 4.96(s, 2H), 5.15(s, 2H), 5.23, 5.36(ABq, J=12Hz, 2H), 6.14(d, J=5Hz, 1H), 6.20(s, 2H), 6.80~6.97(m, 7H), 7.09(d, J=9Hz, 1H), 7.29~7.42(m, 7H), 7.69(d, J=7Hz, 2H), 7.88(d, J=9Hz, 1H), 8.33(d, J=7Hz, 2H) [CDCl$_3$+CD$_3$OD] |
| 19 | BOCCAZ tBu | 3,4-PMB-5-Cl | SO β | Br | 1804, 1722, 1688, 1631, 1612. | 1.42(s, 9H), 1.53(s, 9H), 1.56(s, 3H), 1.57(s, 3H), 3.73 (s, 3H), 3.79(s, 3H), 3.82(s, 3H), 4.27, 4.65(ABq, J=14Hz, 2H), 4.94(d, J=4Hz, 1H), 5.10(s, 2H), 5.18(s, 2H), 5.21, 5.36(ABq, J=13Hz, 2H), 6.13(d, J=4Hz, 1H), 6.35(brs, 2H), 6.8~7.75(m, 17H), 8.34(m, 2H). [CD$_3$SOCD$_3$] |
| 20 | BOCCAZ tBu | 3,4-PMB-6-Cl | SO β | Br | 1800, 1719, 1683, 1629, 1611. | 1.42(s, 9H), 1.43(s, 9H), 1.57(s, 3H), 1.58(s, 3H), 3.72 (s, 3H), 3.78(s, 3H), 3.82(s, 3H), 4.28, 4.68(ABq, J=13Hz, 2H), 4.97(d, J=5Hz, 1H), 5.11(s, 2H), 5.15(s, 2H), 5.22, 5.36(ABq, J=12Hz, 2H), 6.14(d, J=5Hz, 1H), 6.21(brs, 2H), 6.84~6.99, 7.26~7.42(m, 14H), 7.63(d, J=6Hz, 2H), 7.66(s, 1H), 8.27(d, J=6Hz, 2H). [CDCl$_3$—CD$_3$OD] |
| 21 | BOCCAZ tBu | 3,4-PMB-6-Cl | S | Br | 1790, 1717, 1686, 1629, 1611. | 1.42(s, 9H), 1.52(s, 9H), 1.60(s, 3H), 1.63(s, 3H), 3.36, 3.63(ABq, J=18Hz, 2H), 3.74(s, 3H), 3.76(s, 3H), 3.79(s, 3H), 4.31(brs, 2H), 5.01(s, 2H), 5.02(d, J=5Hz, 1H), 5.19, 5.29(ABq, J=12Hz, 2H), 5.21(s, 2H), 5.96, 6.00(dd, J=5Hz, J=8Hz, 1H), 6.72(brs, 2H), 6.80~7.43(m, 14H), 7.53 (d, J=6Hz, 2H), 7.86(s, 1H), 8.20(d, J=8Hz, 1H), 8.68(d, J=6Hz, 2H). |
| 22 | BOCCAZ tBu | 3,4-PMB-6-Cl | S | Br | 1791, 1720, 1690, 1631, 1612. | 1.45(s, 9H), 1.54(s, 9H), 1.58(brs, 6H), 3.47, 3.69(ABq, J=22Hz, 2H), 3.76(s, 3H), 3.79(s, 3H), 3.82(s, 3H), 4.34 (brs, 2H), 5.09(s, 4H), ca. 5.2(m, 3H), 5.97(d, J=3Hz, 1H), 6.50(brs, 2H), 6.7~7.8(m, 17H), 8.5(m, 2H). |
| 23 | BOCCAZ tBu | 3,4-OH-2,5-Cl | SO β | Br | nd. | 1.42(s, 9H), 1.53(s, 9H), 1.55(s, 3H), 1.57(s, 3H), 3.77 (s, 3H), 4.34, 4.49(ABq, J=12.5Hz, 2H), 4.95(d, J=5.0Hz, 1H), 5.25, 5.31(ABq, J=12.0Hz, 2H), 6.12(d, J=5.0Hz, 1H), 6.88(d, J=8Hz, 1H), 7.25(s, 1H), 7.37(d, J=8Hz, 2H), 7.44(d, J=7Hz, 2H), 7.55(s, 1H), 7.66(d, J=7Hz, 2H). |
| 24 | CAZtBu | 3,4-OAc-a-Me $R^5$=MeCH | S | — | 1760, 1660sh [Nujol] | nd. |
| 25 | BOCCET BBzl | 3,4-PMB | S | Br |  | nd. |

TABLE 3

Physical constants of betains

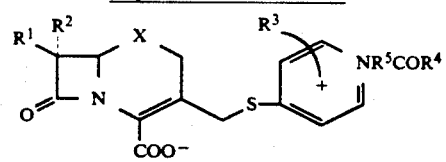

$R^2 = H$, $R^3 = H$, & $R^5 = CH_2$ unless otherwise specified.

| No. | $R^1$ | $R^4$ | X | IR (KBr) | NMR: δ (CD$_3$SOCD$_3$) ppm |
|---|---|---|---|---|---|
| 1 | G | 3,4-OH | S | 1766, 1672, 1630. | 3.36~3.60(m, 4H), 4.36, 4.69(ABq, J=13.4Hz, 2H), 4.98(d, J=5Hz, 1H), 5.49(dd, J=5Hz, J=8Hz, 1H), 6.11(s, 2H), 6.95(d, J=8Hz, 1H), 7.10~7.55(m, 7H), 8.38(d, J=7Hz, 2H), 8.57(d, J=7Hz, 2H), 9.06(d, J=8Hz, 1H). |
| 2 | FMOX $R^2$ = OMe, X = O | 3,4-OAc | MO | nd. | 3.37(s, 3H), 3.59, 3.69(ABq, J=15.2Hz, 2H), 4.30, 4.74(ABq, J=14Hz, 2H), 4.39(s, 2H), 5.02(s, 1H), 6.10(s, 2H), 6.90~7.12(m, 4H), 8.34(d, J=6Hz, 2H), 8.59(d, J=6Hz, 2H), 9.23(s, 1H). |
| 3 | CTX | 2,3-OH | S | 1767, 1660sh, 1630 | 3.43, 3.59(ABq, J=17.6Hz, 2H), 4.48, 4.58(ABq, J=13.6Hz, 2H), 5.06(d, J=4.6Hz, 1H), 5.61(dd, J=4.6Hz, J=7.8Hz, 1H), 6.05(s, 2H), 6.74(s, 1H), 6.74(t, J=7.4Hz, 1H), 7.11(d, J=7.4Hz, 1H), 7.22(s, 2H), 7.23(d, J=7.4Hz, 1H), 8.29(d, J=6.2Hz, 2H), 8.60(d, J=6.2Hz, 2H), 9.55(d, J=7.8Hz, 1H). |
| 4 | CTX | 2,3-OH | SO | 1777, 1665sh, 1630 | 3.89, 4.19(ABq, J=18.6Hz, 2H), 4.10(s, 3H), 4.46, 4.62(ABq, J=13.8Hz, 2H), 5.13(d, J=4.8Hz, 1H), 6.09(d, J=4.8Hz, 1H), 6.22(s, 2H), 6.99(t, J=8Hz, 1H), 7.19(s, 1H), 7.26(dd, |

TABLE 3-continued

Physical constants of betains

Structure: R¹, R² on β-lactam; X linker; R³ on pyridinium ring with NR⁵COR⁴ substituent; COO⁻ on cepham.

R² = H, R³ = H, & R⁵ = CH₂ unless otherwise specified.

| No. | R¹ | R⁴ | X | IR (KBr) | NMR: δ (CD₃SOCD₃) ppm |
|---|---|---|---|---|---|
| 5 | CTX | 3,4-OH | S | 1764, 1670, 1630. | J=1.4Hz, J=8Hz, 1H), 7.48(dd, J=1.4Hz, J=8Hz, 1H), 7.94(d, J=5.6Hz, 2H), 8.43(d, J=5.6Hz, 2H). [D₂O—DCl] 3.41, 3.55(ABq, J=17.6Hz, 2H), 4.43, 4.61(ABq, J=12.6Hz, 2H), 5.03(d, J=4.8Hz, 1H), 5.57(dd, J=4.8Hz, J=8.2Hz, 1H), 6.09(s, 2H), 6.73(s, 1H), 6.94(d, J=8.4Hz, 1H), 7.22(s, 2H), 7.35(d, J=8.4Hz, 1H), 7.51(s, 1H), 8.32(d, J=6.6Hz, 2H), 8.55(d, J=6.6Hz, 2H), 9.54(d, J=8.2Hz, 1H). |
| 6 | CAZ | 2,3-OH | SO | 1780, 1670sh, 1630 | 1.46(s, 6H), 3.63, 3.78(ABq, J=18Hz, 2H), 4.38, 4.79(ABq, J=15Hz, 2H), 4.89(d, J=4Hz, 1H), 5.80(dd, J=4Hz, 1H), 6.04(brs, 2H), 6.73(t, J=8Hz, 1H), 6.79(s, 1H), 7.09(d, J=8Hz, 1H), 7.24(d, J=8Hz, 1H), 7.28(brs, 2H), 8.13(d, J=6Hz, 2H), 8.59(d, J=6Hz, 2H). |
| 7 | CAZ | 2,3-OH | S | 1770, 1670sh 1630. | 1.44(s, 6H), 3.42, 3.61(ABq, J=15Hz, 2H), 4.52(brs, 2H), 5.09(s, 2H), 5.67(dd, J=5Hz, J=8Hz, 1H), 6.72(s, 1H), 6.72(t, J=8Hz, 1H), 7.10(d, J=8Hz, 1H), 7.23(d, J=8Hz, 1H), 7.28(brs, 2H), 8.25(d, J=7Hz, 2H), 8.60(d, J=7Hz, 2H), 9.50(d, J=8Hz, 1H). |
| 8 | CAZ | 3,4-OH | S | 1766, 1670, 1630. | 1.44(s, 3H), 1.48(s, 3H), 3.42, 3.58(ABq, J=17.2Hz, 2H), 4.45, 4.55(ABq, J=14Hz, 2H), 5.07(d, J=4.6Hz, 1H), 5.66(dd, J=4.6Hz, J=8.4Hz, 1H), 6.11(s, 2H), 6.71(s, 1H), 6.94(d, J=8.2Hz, 1H), 7.29(s, 2H), 7.38(d, J=8.2Hz, 1H), 7.48(s, 1H), 8.26(d, J=6.6Hz, 2H), 8.57(d, J=6.6Hz, 2H), 9.6(brs, 1H). |
| 9 | CAZ | 3,4-OH | SO | 1778, 1673, 1630. | 1.46(s, 3H), 1.47(s, 3H), 3.61, 3.75(ABq, J=17.4Hz, 2H), 4.43, 4.73(ABq, J=13.6Hz, 2H), 4.89(d, J=4Hz, 1H), 5.79(dd, J=4Hz, J=8.4Hz, 1H), 6.10(s, 2H), 6.80(s, 1H), 6.95(d, J=8.4Hz, 1H), 7.30(s, 2H), 7.39(d, J=8.4Hz, 1H), 7.47(s, 1H), 8.19(d, J=6.8Hz, 2H), 8.33(d, J=8.4Hz, 1H), 8.55(d, J=8.4Hz, 2H). |
| 10 | CAZ-Na | 3,4-OH | S | 1760, 1660sh 1630. | 1.40(s, 3H), 1.44(s, 3H), 3.37, 3.53(ABq, J=16.7Hz, 2H), 4.54(d, J=5Hz, 2H), 5.04(d, J=5Hz, 1H), 5.65(d, J=5Hz, 1H), 6.52(d, J=9Hz, 2H), 6.73(s, 1H), 7.22(s, 1H), 7.37(d, J=9Hz, 1H), 8.24(d, J=6Hz, 2H), 8.54(d, J=6Hz, 2H). [CD₃SOCD₃—CD₃OD] |
| 11 | CAZ | 3,4-OAc | S | 1765, 1660sh 1623 [Nujol] | 1.42(s, 3H), 1.44(s, 3H), 2.33(s, 6H), 3.40, 3.56(ABq, J=17.5Hz, 2H), 4.46, 4.55(ABq, J=14Hz, 2H), 5.06(d, J=5Hz, 1H), 5.64(dd, J=5Hz, J=9Hz, 1H), 6.25(brs, 2H), 6.72(s, 1H), 7.28(brs, 2H), 7.57(d, J=8.4Hz, 1H), 7.95(s, 1H), 8.01(d, J=8.4Hz, 1H), 8.35(d, J=7Hz, 2H), 8.59(d, J=7Hz, 2H). |
|  |  |  |  | 3400, 1770, 1675, 1630, 1260, 1200, 1109. | 1.44(s, 3H), 1.45(s, 3H), 2.34(s, 3H), 2.49(s, 3H), 3.42, 3.57(ABq, J=18Hz, 2H), 4.48, 4.56(ABq, J=13Hz, 2H), 5.07(d, J=5Hz, 1H), 5.65(d, J=5Hz, 1H), 6.73(s, 1H), 7.57(d, J=8Hz, 1H), 7.95~8.04(m, 2H), 8.34(d, J=7Hz, 2H), 8.58(d, J=7Hz, 2H). [CD₃SOCD₃ + CD₃OD] |
| 12 | CAZ | 3,4-OAc | SO β | 3400, 1775, 1675, 1630, 1260, 1200, 1108. | 1.47(s, 3H), 1.48(s, 3H), 2.33(s, 3H), 2.34(s, 3H), 4.46, 4.74(ABq, J=13.5Hz, 2H), 4.89(d, J=4.8Hz, 1H), 5.80(d, J=4.8Hz, 1H), 6.82(s, 1H), 7.58(d, J=8.4Hz, 1H), 7.95~8.04(m, 2H), 8.28(d, J=7Hz, 2H), 8.57(d, J=7Hz, 2H). [CD₃SOCD₃ + CD₃OD] |
| 13 | CAZ | 3,4-OAc | O | nd. | 1.41(s, 6H), 4.43, 4.49, 4.69(ABq, J=14Hz, 2H), 5.11(d, J=3.4Hz, 1H), 5.49(dd, J=3.4Hz, J=8.8Hz, 1H), 6.09(s, 2H), 6.76(s, 1H), 6.94(d, J=8.4Hz, 1H), 7.27(s, 2H), 7.38(d, J=8.4Hz, 1H), 7.49(s, 1H), 8.26(d, J=7Hz, 2H), 8.58(d, J=7Hz, 2H), 9.3(s, 1H). |
| 14 | CAZ | 3,4-OH-6-Me | S | 3330, 1770, 1670, 1630, 1585, 1360, 1109. | 1.42(s, 3H), 1.44(s, 3H), 2.32(s, 3H), 3.45, 3.59(ABq, J=16Hz, 2H), 4.34, 4.67(ABq, J=14Hz, 2H), 5.10(d, J=4.5Hz, 1H), 5.65(dd, J=4.5Hz, J=8Hz, 2H), 6.05(brs, 2H), 6.71(s, 2H), 7.30(brs, 2H), 7.77(brs, 1H), 8.30(d, J=6.8Hz, 2H), 8.53(d, J=6.8Hz, 2H), 9.53(d, J=8Hz, 1H). |
| 15 | CAZ | 3,4-OH-6-Me | SO β | 3350, 1782, 1675, 1630, 1600, 1525, 1360, 1190, 1110. | 1.46(s, 3H), 1.47(s, 3H), 2.32(s, 3H), 3.59, 3.76(ABq, J=18.5Hz, 2H), 4.52, 4.64(ABq, J=13Hz, 2H), 4.91(d, J=4.5Hz, 1H), 5.80(dd, J=4.5Hz, J=8Hz, 1H), 6.033(brs, 1H), 6.73(s, 1H), 6.80(s, 1H), 7.29(brs, 2H), 7.69(s, 1H), 8.19(d, J=6.4Hz, 2H), 8.33(d, J=8Hz, 1H), 8.51(d, J=6.4Hz, 2H). |
| 16 | CAZ TFA-salt | 3,4-OH-2-Cl | S | 1770, 1675, 1630. [KBr] | 1.50(2xs, 6H), 3.49, 3.73(ABq, J=17Hz, 2H), 4.22, 4.43(ABq, J=14Hz, 2H), 5.20(d, J=5Hz, 1H), 5.78(d, J=5Hz, 1H), 6.64(d, J=10Hz, 1H), 6.95(s, 1H), 7.43(d, J=10Hz, 1H), 7.86(m, 2H), 8.31(m, 2H). [D₂O—NaHCO₃] |
| 17 | CAZ | 3,4-OH-2-Cl | SO β | 1760, 1673, 1630. [KBr] | 1.48(s, 3H), 1.51(s, 3H), 3.71, 3.96(ABq, J=11Hz, 2H), 4.20, 4.57(ABq, J=13Hz, 2H), 4.99(d, J=5Hz, 1H), 6.01(d, J=5Hz, 1H), 6.66(d, J=9Hz, 1H), 6.96(s, 1H), 7.43(d, J=9Hz, 1H), 7.84(m, 2H), 8.33(m, 2H). [D₂O—NaHCO₃] |
| 18 | CAZ | 3,4-OH-5-Cl | S | 1770, 1675, 1630. | 1.43(s, 3H), 1.44(s, 3H), 3.44, 3.61(ABq, J=19.6Hz, 2H), 4.44, 4.56(ABq, J=13Hz, 2H), 5.11(d, J=5Hz, 1H), 5.68, 5.72(dd, |

TABLE 3-continued

Physical constants of betains

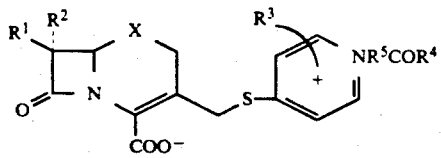

$R^2 = H$, $R^3 = H$, & $R^5 = CH_2$ unless otherwise specified.

| No. | $R^1$ | $R^4$ | X | IR (KBr) | NMR: δ ($CD_3SOCD_3$) ppm |
|---|---|---|---|---|---|
| | | | | | J=5Hz, J=8Hz, 1H), 6.09(brs, 2H), 6.71(s, 1H), 7.98(brs, 2H), 7.52(brs, 2H), 8.23(d, J=7Hz, 2H), 8.54(d, J=7Hz, 2H). |
| 19 | CAZ | 3,4-OH-5-Cl | SOβ | 1780, 1675, 1630. | 1.46(s, 3H), 1.47(s, 3H), 3.63, 3.78(ABq, J=18.6Hz, 2H), 4.45, 4.69(ABq, J=13Hz, 2H), 4.92(d, J=5Hz, 1H), 5.67, 5.82(dd, J=5Hz, J=8Hz, 1H), 6.10(brs, 2H), 6.80(s, 1H), 7.30(brs, 2H), 7.53(s, 2H), 8.18(d, J=6Hz, 2H), 8.32(d, J=8Hz, 1H), 8.54(d, J=6Hz, 2H). |
| 22 | CAZ | 3,4-OH-6-Cl | S | 1765, 1668, 1630. | 1.43(s, 3H), 1.44(s, 3H), 3.44, 3.59(ABq, J=18Hz, 2H), 4.36, 4.63(ABq, J=13Hz, 2H), 5.10(d, J=5Hz, 1H), 5.65, 5.69(dd, J=5Hz, J=8Hz, 1H), 6.07(brs, 2H), 6.71(s, 1H), 6.94(s, 1H), 7.29(brs, 2H), 7.82(s, 1H), 8.25(d, J=6Hz, 2H), 8.53(d, J=6Hz, 2H), 9.54(d, J=8Hz, 1H). |
| 21 | CAZ | 3,4-OH-6-Cl | SOβ | 1785, 1675, 1630. | 1.46(s, 3H), 1.47(s, 3H), 3.60, 3.77(ABq, J=18Hz, 2H), 4.50, 4.65(ABq, J=12Hz, 2H), 4.91(d, J=5Hz, 1H), 5.80, 5.83(dd, J=5Hz, J=8Hz, 1H), 6.06(brs, 2H), 6.80(s, 1H), 6.94(s, 1H), 7.29(brs, 2H), 7.75(s, 1H), 8.18(d, J=6Hz, 2H), 8.32(d, J=8Hz, 1H), 8.54(d, J=6Hz, 2H). |
| 22 | CAZ | 3,4-OAc-α-Me $R^5$ = MeCH | S | 1765, 1665. [Nujol] | 1.43(s, 6H), 1.90(d, J=8.4Hz, 3H), 2.34(s, 6H), 3.42, 3.57(ABq, J=18Hz, 2H), 4.474, 4.58(ABq, J=16Hz, 2H), 5.06(d, J=5Hz, 1H), 5.66(dd, J=5Hz, J=8Hz, 1H), 6.72(s, 1H), 6.75(brs, 1H), 7.28(brs, 2H), 7.57(d, J=8.6Hz, 1H), 7.99(d, J=2Hz, 1H), 8.04(dd, J=2Hz, J=8.6Hz, 1H), 8.32(d, J=6.7Hz, 2H), 8.77(d, J=6.7Hz, 2H). |
| 23 | CAZ | 3,4-OH-α-Me $R^5$ = MeCH | S | 1755, 1660sh | 1.48(s, 6H), 1.90(d, J=8Hz, 3H), 3.46, 3.70(ABq, J=18Hz, 2H), 4.24, 4.41(ABq, J=16Hz, 2H), 5.16(t, J=5Hz, 1H), 5.70~5.80(m, 1H), 6.42(brs, 1H), 6.90(d, J=7Hz, 1H), 6.91(s, 1H), 7.42(brs, 1H), 7.56(d, J=7Hz, 1H), 7.86(brs, 2H), 8.48(brs, 2H) [$D_2O$]. |
| 24 | CAZ | 3,4-OH-2,5-Cl | SOβ | nd. | 1.46(s, 3H), 1.47(s, 3H), 4.41, 4.57(ABq, J=13Hz, 2H), 5.01(d, J=5Hz, 1H), 5.97(d, J=5Hz, 1H), 6.80(s, 1H), 7.61(s, 1H), 8.07(d, J=6Hz, 2H), 8.60(d, J=6Hz, 2H). |
| 25 | CAZ | 3,4-OHHR $R^3$ = 2,3-$(CH_2)_3$ | S | nd. | 1.45(s, 6H), 2.05~2.30(m, 2H), 2.80~3.80(m, 8H), 5.21(d, J=4.8Hz, 1H), 5.83(dd, J=4.8Hz, J=8.2Hz, 1H), 6.14(s, 2H), 6.73(s, 1H), 6.95(d, J=7.2Hz, 1H), 7.30(brs, 2H), 7.40~7.55(m, 2H), 8.02(d, J=7Hz, 1H), 8.52(d, J=7Hz, 1H), 9.46(d, J=8.2Hz, 1H). |
| 26 | CAZ | 3,4-OHHR $R^3$ = 2,3-$(CH_2)_3$ | SOβ | nd. | 1.44(s, 3H), 1.47(s, 3H), 2.10~2.30(m, 2H), 2.8~3.2(m, 4H), 3.60~5.10(m, 6H), 5.95(d, J=4.5Hz, 1H), 6.4~6.6(m, 1H), 6.95(s, 1H), 7.2~7.4(m, 2H), 7.55(m, 1H), 8.2(m, 1H). [$D_2O$] |
| 27 | CETB | 3,4-OH | S | 3350, 1767, 1670, 1630, 1525, 1110. | 1.31(s, 6H), 3.46, 3.56(ABq, J=18.5Hz, 2H), 4.47, 4.58(ABq, J=13Hz, 2H), 5.06(d, J=4.8Hz, 1H), 5.61(dd, J=4.8Hz, J=8Hz, 1H), 6.10(brs, 2H), 6.21(s, 1H), 6.58(s, 1H), 6.95(d, J=8.5Hz, 1H), 7.09(brs, 2H), 7.38(brs, 2H), 7.50(brs, 1H), 8.30(d, J=6.7Hz, 2H), 8.57(d, J=6.7Hz, 2H), 9.35(d, J=8Hz, 1H). |

What we claim is:

1. A 3-pyridiniothiomethylcephalosporin derivative having vic-dihydroxyaryl group of the following formula (I):

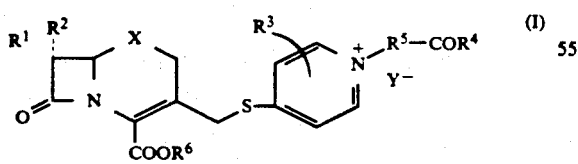

(wherein,
$R^1$ is a $C_1$ to $C_{20}$ alkanoylamino or $C_7$-$C_{20}$ aralkanoylamino,
$R^2$ is hydrogen or methoxy,
$R^3$ is hydrogen, halo, cyano, $C_2$ to $C_9$ divalent alkylene, $C_1$ to $C_8$ alkyl, $C_2$ to $C_6$ alkenyl, carboxy, $C_2$ to $C_9$ alkoxycarbonyl, $C_8$ to $C_{15}$ aralkoxycarbonyl, carbamoyl, nitro or a mono- or bicyclic heterocyclic having 1 to 4 heteroatoms selected from nitrogen, oxygen and sulfur,
$R^4$ is vic-dihydroxyaryl, wherein aryl is a monocyclic or dicyclic, five to six-membered carbocyclic aryl selected from the group consisting of phenyl, naphthyl, indenyl, indanyl, and tetralinyl or heterocyclic aryl having oxygen, nitrogen, or sulfur as heteroatoms selected from furyl, thienyl, pyrrolyl, oxazolyl, thiazolyl, imidazolyl, oxadiazolyl, thiadiazolyl, triazolyl, thiatriazolyl, tetrazolyl, pyridyl, pyranyl, indolyl, benzofuryl, benzothienyl, benzoimidazolyl, benzothiazolyl, benzopyrazinyl, quinolyl, and pyridopyridyl,
$R^5$ is straight or branched $C_1$ to $C_5$ alkylene,
$R^6$ is hydrogen, a carboxy protecting group, or combined with Y a negative charge,
X is —S— or sulfinyl,
Y is a counter-ion of pyridinio or combined with $R^6$ a negative charge, or a salt thereof.

2. A compound as claimed in claim 1 wherein $R^1$ is difluoromethylthioacetamido, phenylacetylamino, 2-(2-aminothiazol-4-yl)-2-(hydroxyimino)acetamido, 2-(2-aminothiazol-4-yl)-2-(C1 to C5-alkoxyimino)acetamido, 2-(2-aminothiazol-4-yl)-2-(carboxymethoxyimino)acetamido, or 2-(2-aminothiazol-4-yl)-2-(1-carboxy-1-methylethoxyimino)acetamido, 2-(2-aminothiazol-4-yl)-4-carboxy-2-butenamido, or 2-(2-aminothiazol-4-yl)-4-carboxy-3-methyl-2-butenamido.

3. A compound as claimed in claim 1 wherein $R^2$ is hydrogen.

4. A compound as claimed in claim 1 wherein $R^3$ is hydrogen or trimethylene.

5. A compound as claimed in claim 1 wherein $R^4$ is 2,3-dihydroxyphenyl or 3,4-dihydroxyphenyl.

6. A compound as claimed in claim 1 wherein $R^5$ is methylene or ethylidene.

7. A compound as claimed in claim 1 wherein $R^6$ is hydrogen, alkali metal, or combined with Y a negative charge.

8. A compound as claimed in claim 1 wherein X is sulfur.

9. A compound as claimed in claim 1 wherein Y is halogen ion or combined with $R^6$ a negative charge.

10. A compound as claimed in claim 1 that is one selected from the group consisting of:

7β-phenylacetamido-3-[1-(3,4-dihydroxyphenacyl)-4-pyridinio]thiomethyl-3-cephem-4-carboxylate, 7β-difluoromethylthioacetamido-3-[1-(3,4-diacetoxyphenacyl)-4-pyridinio]thiomethyl-7α-methoxy-1-oxa-1-dethia-3-cephem-4-carboxylate, 7β-[2-(2-amino-4-thiazolyl)-2-methoxyimino]acetamido-3-[1-(2,3-dihydroxyphenacyl)-4-pyridinio]thiomethyl-3-cephem-4-carboxylate, 7β-[2-(2-amino-4-thiazolyl)-2-methoxyimino]acetamido-3-[1-(3,4-dihydroxyphenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(2,3-dihydroxyphenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(3,4-dihydroxyphenacyl)-4-pyridinio]thiomethyl-3-cephem-4-carboxylate, 7β-[2-(2-amino-4-thiazolyl)-2-(1-sodiooxycarbonyl-1-methylethoxyimino)acetamido]-3-[1-(3,4-dihydroxyphenacyl)-4-pyridinio]thiomethyl-3-cephem-4-carboxylate, 7β-[2-(2-amino-4-thiazolyl)-2-(1-carboxy-1-methylethoxyimino)-acetamido]-3-[1-(3,4-diacetoxyphenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(3,4-diacetoxyphenacyl)-4-pyridinio]thiomethyl-1-oxa-1-dethia-3-cephem-4-carboxylate, 7β-[2-(2-amino-4-thiazolyl)-2-(1-carboxy-1-methylethoxyimino)acetamido]-3-[1-(3,4-dihydroxy-6 or α-methylphenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(3,4-dihydroxy-2, 5 or 6-chlorophenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(3,4-dihydroxy-2,5-dichlorophenacyl)-4-pyridinio]thiomethyl-3-cephem-4-carboxylate, 7β-[2-(2-amino-4-thiazolyl)-2-(1-carboxy-1-methylethoxyimino)acetamido]-3-[1-(3,4-dihydroxyphenacyl)-2,3-trimethylene-4-pyridinio]thiomethyl-3-cephem-4-carboxylate, and 7β-[2-(2-amino-4-thiazolyl)-4-carboxy-4-methyl-2-pentenamido]-3-[1-(3,4-dihydroxy-2-chlorophenacyl)-4-pyridinio]thiomethyl-3-cephem-4-carboxylate and 1β-oxides and alkali metal salts thereof.

11. An antibacterial composition comprising an effective amount of a compound as claimed in claim 1 as an effective ingredient and a pharmaceutically acceptable carrier.

12. A method for inhibiting the growth of sensitive bacteria which comprises contacting an effective amount of a compound as claimed in claim 1 with the bacteria.

13. A method for preventing or treating an infection caused by sensitive bacteria comprising administering an effective amount of a compound as claimed in claim 1.

* * * * *